US010159952B2

(12) United States Patent
Finski et al.

(10) Patent No.: US 10,159,952 B2
(45) Date of Patent: Dec. 25, 2018

(54) METHOD FOR LYSING A SINGLE CELL IN A SOLID TISSUE

(71) Applicant: PRESIDENT AND FELLOWS OF HARVARD COLLEGE, Cambridge, MA (US)

(72) Inventors: Alexei Finski, Somerville, MA (US); Gavin MacBeath, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/622,661

(22) Filed: Jun. 14, 2017

(65) Prior Publication Data

US 2018/0104663 A1 Apr. 19, 2018

Related U.S. Application Data

(62) Division of application No. 14/427,593, filed as application No. PCT/US2013/059485 on Sep. 12, 2013, now abandoned.

(60) Provisional application No. 61/729,127, filed on Nov. 21, 2012, provisional application No. 61/700,517, filed on Sep. 13, 2012.

(51) Int. Cl.
*G01N 33/53* (2006.01)
*B01J 19/00* (2006.01)
*G01N 33/50* (2006.01)
*G01N 33/68* (2006.01)

(52) U.S. Cl.
CPC ...... *B01J 19/0046* (2013.01); *G01N 33/5091* (2013.01); *G01N 33/6803* (2013.01); *G01N 33/6848* (2013.01); *B01J 2219/0061* (2013.01); *B01J 2219/00596* (2013.01); *B01J 2219/00626* (2013.01); *B01J 2219/00691* (2013.01); *B01J 2219/00695* (2013.01); *B01J 2219/00702* (2013.01); *B01J 2219/00725* (2013.01)

(58) Field of Classification Search
None
See application file for complete search history.

(56) References Cited

U.S. PATENT DOCUMENTS

| | | | |
|---|---|---|---|
| 6,846,668 B1 * | 1/2005 | Garman | C12M 35/00 435/285.1 |
| 7,670,768 B1 | 3/2010 | Heath | |
| 2005/0095639 A1 | 5/2005 | Schreiber | |
| 2013/0302884 A1 | 11/2013 | Fowler | |
| 2013/0303746 A1 * | 11/2013 | Ruegg | C12N 15/1003 536/25.42 |
| 2014/0154776 A1 | 6/2014 | Bendzko | |
| 2016/0168631 A1 | 6/2016 | Bengtsson | |

FOREIGN PATENT DOCUMENTS

| | | |
|---|---|---|
| JP | 2011120582 A | 6/2011 |
| WO | 2000/020554 A1 | 4/2000 |
| WO | 2014/043365 A1 | 3/2014 |

OTHER PUBLICATIONS

Bissell et al., "Putting tumours in context", Nat Rev Cancer 1(1) 46-54 (2001).
Brandtzaeg et al., "Evaluation of nine different fixatives. 2. Preservation of IgG, IgA and secretory component in an artificial immunohistochemical test substrate", Histochemistry 81(3) 213-219 (1984).
Brown et al., "Current techniques for single-cell lysis", J R Soc Interface 5(Suppl 2) S131-138 (2008).
Collaud et al., "Laser-capture microdissection impairs activity-based protein profiles for serine hydrolase in human lung adenocarcinoma.", J Biomol Tech 21(1) 25-28 (2010).
Dalerba et al., "Single-cell dissection of transcriptional heterogeneity in human colon tumors", Nat Biotechnol 29(12) 1120-1127 (2011).
Engelholm et al., "Disaggregation of human solid tumours by combined mechanical and enzymatic methods", Br J Cancer 51(1) 93-98 (1985).
Espina et al., "Laser-capture microdissection", Nat Protoc 1(2) 586-603 (2006).
Fischback et al., "Engineering tumors with 3D scaffolds", Nat Methods 4(10) 855-860 (2007).
Gutstein et al., "Laser capture sampling and analytical issues in proteomics", Expert Rev Proteomics 4(5) 627-637 (2007).
Hanahan et al., "The hallmarks of cancer", Cell 100(1) 57-70 (2000).
Holtfreter et al., "Fixation-associated quantitative variations of DNA fluorescence observed in flow cytometric analysis of hemopoietic cells from adult diploid frogs", Cytometry 11(6) 676-685 (1990).
Irimia et al., "Single-cell chemical lysis in picoliter-scale closed volumes using a microfabricated device", Anal Chem 16(20) 6137-6143 (2004).
Jen et al., "Single-cell chemical lysis on microfluidic chips with arrays of microwells", Sensors (Basel) 12(1) 347-358 (2012).
Landgraf et al., "Segregation of molecules at cell division reveals native protein localization", Nat Methods 9(5) 480-482 (2012).
Melan et al., "Redistribution and differential extraction of soluble proteins in permeabilized cultured cells. Implications for immunofluorescence microscopy", J Cell Sci 101(Pt 4) 731-743 (1992).
Micheva et al., "Array tomography: a new tool for imaging the molecular architecture and ultrastructure of neural circuits", Neuron 55(1) 25-36 (2007).
Morris et al., "Transcriptome analysis of single cells", J Vis Exp (50) e2634 (2011).

(Continued)

*Primary Examiner* — Ralph J Gitomer
(74) *Attorney, Agent, or Firm* — Nixon Peabody LLP; David S. Resnick; Teresa A. Ptashka

(57) ABSTRACT

The invention provides a method for lysing a single cell embedded in a tissue from the inside of the cell, and collecting the intracellular lysate for use in analytical methods. This method preserves the state of molecules of the cell, and therefore allows for transformation of a single target cell in live tissue into a format that can be evaluated using analytical methods.

16 Claims, 35 Drawing Sheets

(56) References Cited

OTHER PUBLICATIONS

Mouledous et al., "Lack of compatibility of histological staining methods with proteomic analysis of laser-capture microdissected brain samples", J Biomol Tech 13(4) 258-264 (2002).
Pallavicini, "Solid Tissue Dispersal for Cytokinetic Analyses", Techniques in Cell Cycle Analysis p. 139-162 (1987).
Schnell et al., "Immunolabeling artifacts and the need for live-cell imaging", Nat Methods 9(2) 152-158 (2012).
Sevecka et al., "State-based discovery: a multidimensional screen for small-molecule modulators of EGF signaling", Nat Methods 3(10) 825-831 (2006).
Sigal et al., "Dynamic proteomics in individual human cells uncovers widespread cell-cycle dependence of nuclear proteins", Nat Methods 3(7) 525-531 (2006).
Tanaka et al., "Membrane molecules mobile even after chemical fixation", Nat Methods 7(11) 865-866 (2010).
Waymouth, "To disaggregate or not to disaggregate injury and cell disaggregation, transient or permanent?", In Vitro 10; 97-111 (1974).
Yasuda et al., "Imaging calcium concentration dynamics in small neuronal compartments", Sci STKE 2004(219) p. 15 (2004).

* cited by examiner

PKCδ

PKCα

PAK1

FAK

GFP2

GFP1

AXL + MET + AKT +

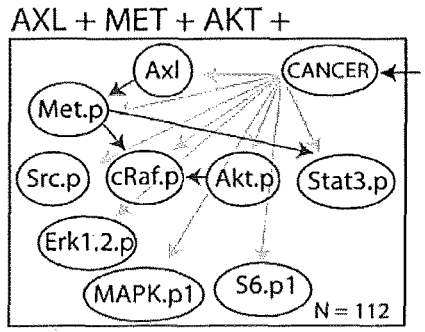

P(Cancer = T) = 0.5

$AXL + MET + AKT+:$ $P(Cancer, Axl, Met.p, Src.p, cRaf.p,$
$\quad Akt.p, Stat3.p, Erk1.2.p, MAPK.p1, S6.p1) =$
$P(Cancer)$
$P(Axl|Cancer)$
$P(Met.p|Axl, Cancer)$
$P(Src.p|Cancer)$
$P(cRaf.p|Akt.p, Met.p, Cancer)$
$P(Akt.p|Cancer)$
$P(Stat3.p|Met.p, Cancer)$
$P(Erk1.2.p|Cancer)$
$P(MAPKp|Cancer)$
$P(S6p|Cancer).$

AXL + MET + AKT ++

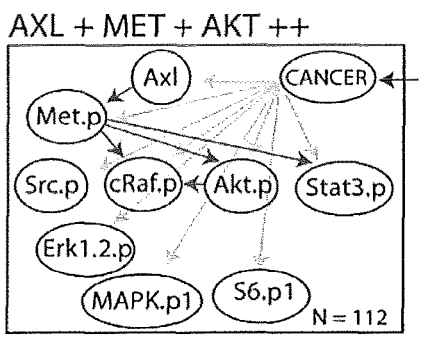

P(Cancer = T) = 0.5

$AXL + MET + AKT++:$ $P(Cancer, Axl, Met.p, Src.p, cRaf.p,$
$\quad Akt.p, Stat3.p, Erk1.2.p, MAPK.p1, S6.p1) =$
$P(Cancer)$
$P(Axl|Cancer)$
$P(Met.p|Axl, Cancer)$
$P(Src.p|Cancer)$
$P(cRaf.p|Akt.p, Met.p, Cancer)$
$P(Akt.p|Met.p, Cancer)$
$P(Stat3.p|Met.p, Cancer)$
$P(Erk1.2.p|Cancer)$
$P(MAPKp|Cancer)$
$P(S6p|Cancer).$

AXL + MET + AKT +++

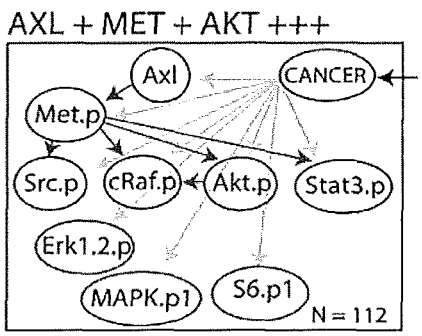

P(Cancer = T) = 0.5

$AXL + MET + AKT+++:$ $P(Cancer, Axl, Met.p, Src.p, cRaf.p,$
$\quad Akt.p, Stat3.p, Erk1.2.p, MAPK.p1, S6.p1) =$
$P(Cancer)$
$P(Axl|Cancer)$
$P(Met.p|Axl, Cancer)$
$P(Src.p|Met.p, Cancer)$
$P(cRaf.p|Akt.p, Met.p, Cancer)$
$P(Akt.p|Met.p, Cancer)$
$P(Stat3.p|Met.p, Cancer)$
$P(Erk1.2.p|Cancer)$
$P(MAPKp|Cancer)$
$P(S6p|Cancer).$

FULL PATHWAY

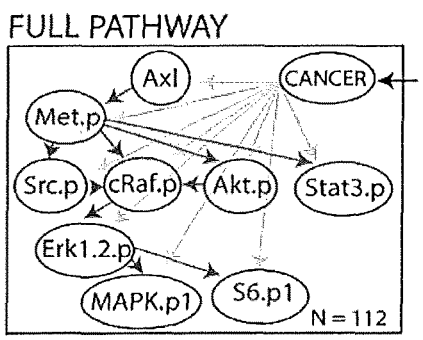

P(Cancer = T) = 0.5

$Full\ Pathway:$ $P(Cancer, Axl, Met.p, Src.p, cRaf.p,$
$\quad Akt.p, Stat3.p, Erk1.2.p, MAPK.p1, S6.p1) =$
$P(Cancer)$
$P(Axl|Cancer)$
$P(Met.p|Axl, Cancer)$
$P(Src.p|Met.p, Cancer)$
$P(cRaf.p|Src.p, Akt.p, Met.p, Cancer)$
$P(Akt.p|Met.p, Cancer)$
$P(Stat3.p|Met.p, Cancer)$
$P(Erk1.2.p|cRaf.p, Cancer)$
$P(MAPKp|Erk1.2.p, Cancer)$
$P(S6p|Erk1.2.p, Cancer).$

Figure 23, continued

METHOD FOR LYSING A SINGLE CELL IN A SOLID TISSUE

CROSS-REFERENCE TO RELATED APPLICATIONS

This application is a Divisional Application of U.S. application Ser. No. 14/427,593, filed on Mar. 11, 2015, now abandoned which is a 35 U.S.C. § 371 National Stage Application of International Application No. PCT/US2013/059485, filed on Sep. 12, 2013, which designates the United States, and which claims benefit under 35 U.S.C. § 119(e) of U.S. Provisional Application No. 61/729,127, filed on Nov. 21, 2012, and U.S. Provisional Application No. 61/700,517, filed on Sep. 13, 2012, the contents of each of which are incorporated herein by reference in their entireties.

STATEMENT REGARDING FEDERALLY SPONSORED RESEARCH OR DEVELOPMENT

This invention was made with government support under RC1HG005354 awarded by National Institutes of Health. The government has certain rights in the invention.

BACKGROUND OF THE INVENTION

For the past 50 years, biological research has primarily been performed on cell lines and dissociated cell cultures, because these experimental systems are easy to handle in laboratory settings and provide large amounts of material for study. This trend has led to the development of numerous analytical methods that require large amounts of biological material and are readily applicable to cell lines and dissociated cell cultures. For example, Western blot, mass spectrometry, and lysate microarrays all require relatively large amounts of biological material in order to take full advantage of the analytical power of these methods. Large amounts of biological material are usually obtained by simultaneously lysing a large number of dissociated cells in a culture dish. As a consequence of this continued trend, the development of methods for sampling and analyzing single cells in solid tissues has lagged far behind.

One way to potentially access the power of current analytical methods and apply them to single cells, is to reduce the solid-tissue sample to a dissociated culture or a cell suspension by tissue disaggregation. Tissue disaggregation can be achieved by applying collagenase, tripsin, pepsin, papain, elastase and/or pronase to the solid tissue sample for hours in solution, sometimes followed by the trituration of the disaggregated tissue sample (Waymouth, 1974 In Vitro. 10: 97-111; Engelholm et al., 1985 S. A., Spang-Thomsen, M., Brünner, N., Nøhr, I. and Vindeløv, L. L. (1985) Br J Cancer. 51(1): 93-98; Pallavicini, 1987 Techniques in cell cycle analysis. 139-162). In this way, human solid tumors can be reduced to cell suspensions for analysis by flow cytometry (Dalerba et al., 2011, Nat. Biotechnol. 29:1120-1127). Rodent brain tissue can be reduced to dissociated neuronal cultures, from which single neurons can be sampled for RT-qPCR analysis (Morris et al., 2011, J. Vis. Exp. 50: pii: 2634. doi: 10.3791/2634). However, the information about the location of cells is lost after tissue disaggregation. Also, disaggregation of solid tissue might not disperse all cells of the tissue sample. Disaggregation of solid tissue likely kills many native cells, and likely selects certain cell populations over the others. The cell yields of tissue disaggregation vary across tissue types. 1 g of tissue contains approx. $1*10^9$ cells, whereas the typical yields of tissue disaggregation procedures are below $1*10^8$ cells/g (Pallavicini, 1987 Techniques in cell cycle analysis. 139-162). Moreover, the cells that survive tissue disaggregation lose their cell-type-specific biochemistry and functionality due to the lack of the extracellular matrix and due to the changed cellular environment in the culture dish or in the cell suspension. For example, the cell division rates in cancerous tissues and in 3D models are different from the cell division rates observed in 2D cell lines (Fischbach et al., 2007 Nat Methods. 4(10): 855-860). The malignancy of tumors formed by cells cultured in 2D is lower than the malignancy of tumors formed by cells cultured in 3D (Fischbach et al., 2007 Nat Methods 4(10): 855-860). It is also well known that the extracellular matrix of solid tissue plays a critical role in cancer (Bissell et al., 2001 Nat Rev Cancer 1(1):46-54; Hanahan et al., 2000 Cell. 100(1): 57-70). Therefore, dissociated cell cultures and cell suspensions are not equivalent to the original solid tissue.

Most current solid-tissue study methods require fixation. Both laser-capture microdissection and all immunolabeling-based methods (immunofluorescence, FACS, FISH etc.) require fixation (Gutstein et al., 2007, Expert Rev. Proteomics 4:627-637; Espina et al., 2006, Nat. Protoc. 1:586-603; Mouledous et al., 2002, J. Biomol. Tech. 13:258-264; Brandtzaeg and Rognum, 1984, Histochem. Cell Biol. 81:213-219; Micheva and Smith, 2007, Neuron 55:25-36). The latter can provide useful information about the spatial distribution of substrates across the tissue structure and even within cells. The question however is not what can be done with fixed tissue but whether fixed tissue represents the original pre-fixed tissue. If fixed tissue does not represent the original tissue sample, then any study that is based on fixed tissue is not informative. Fixation processes were first documented more than 100 years ago (Fish, 1896, Transactions of the American Microscopical Society, 17:319-330). The process of aldehyde- and alcohol-based fixation is not well understood but is known to undermine the molecular preservation of the original sample, thereby obfuscating the true native differences between single cells (Schnell et al., 2012, Nat. Meth. 9:152-158; Mouledous et al., 2002, J. Biomol. Techniques 13:258-264; Melan and Sluder, 1992, J. Cell Sci. 101:731-743; Holtfreter and Cohen, 1990, Cytometry 11:676-685; Tanaka et al., 2010, Nat. Methods 7:865-866; Collaud et al., 2010, J. Biomol. Tech. 21:25-28). There exists no universal fixation protocol and each specific fixation protocol is exclusively tuned to certain cell types, certain molecular classes, and certain molecules within a molecular class (Schnell et al., 2012, Nat. Meth. 9:152-158; Mouledous et al., 2002, J. Biomol. Techniques 13:258-264; Melan and Sluder, 1992, J. Cell Sci. 101:731-743; Holtfreter and Cohen, 1990, Cytometry 11:676-685).

In order to study the effects of common fixation and permeabilization protocols on molecular preservation of biological samples, Schnell and colleagues expressed cytosol-soluble GFP in 293T and MDCK cells (Schnell et al., 2012, Nat. Meth. 9:152-158). As expected, aldehyde-based fixation led to protein cross-linking and to antigen masking. A large number of GFP molecules in the GFP-expressing cells could not be reached by the applied specific GFP antibodies, even after the extensive permeabilization of these GFP-expressing cells. The same aldehyde-based fixation protocol also led to the spatial redistribution of GFP proteins in fixed MDCK cells, as compared to the same set of MDCK cells imaged before applying aldehyde-based fixation. In contrast to MDCK cells, no spatial redistribution of GFP was observed after fixing 293T cells with the same aldehyde-based fixation protocol. These observations demonstrate that the effects of aldehyde-based fixation on molecular preservation are cell-type dependent. The permeabilization process that is required to access the intracellular proteins in each aldehyde-fixed single cell also led to the extensive extraction of GFP from all fixed single cells (Schnell et al., 2012, Nat. Meth. 9:152-158). Similarly, alcohol-based fixation extracted most GFP proteins from all single cells, as confirmed by fluorescence and electron microscopy (Schnell et al., 2012, Nat. Meth. 9:152-158). Importantly, in the study by Schnell et al., the true GFP quantity differences between single cells in a given set of single cells could not be reproduced by antibody staining of the same set of single cells after fixation and permeabilization, although the applied GFP antibody was specific and correctly detected GFP, when GFP was targeted to the endoplasmatic reticulum.

In another rigorous study by Melan and Sluder, the authors labeled several proteins of different size and charge with fluorescein-5-isothiocyanate (FITC) and then loaded these labeled proteins into HeLa, 3T3, PtK1 and CHO cells (Melan and Sluder, 1992, J. Cell Sci. 101:731-743). They observed that the extent of protein extraction, caused by aldehyde-based fixation and permeabilization, depended both on the particular protein species and on the particular cell type (Melan and Sluder, 1992, J. Cell Sci. 101:731-743). These observations prove that aldehyde- and alcohol-based fixation and permeabilization decrease the analytical availability of native molecules in an unpredictable cell-type and molecule-dependent manner. The results of additional studies examining the effects of fixation and permeabilization on molecular preservation demonstrate that aldehyde- and alcohol-based fixation and permeabilization undermine the molecular preservation of the original sample in an unpredictable cell-type- and molecule-dependent manner (Schnell et al., 2012, Nat. Meth. 9:152-158; Mouledous et al., 2002, J. Biomol. Techniques 13:258-264; Melan and Sluder, 1992, J. Cell Sci. 101:731-743; Holtfreter and Cohen, 1990, Cytometry 11:676-685).

The second major limitation of all fixation-based methods is the difficulty and often the inability of constructing standard curves. A standard curve maps recorded signals to quantities and can be constructed by a concurrent titration series. A standard curve is the basis for any analytical measurement in any discipline. Different affinity-based probes, such as antibodies, usually have different dissociation constants (KD) and thus also have different slopes of their respective standard curves. A large signal difference is meaningless without knowledge of the corresponding standard curve, as it can be the result of a small difference in quantity or the result of a large difference in quantity depending on the slope of the underlying standard curve (FIG. 1). Standard curves also enable absolute measurements, as signals can be mapped to the corresponding absolute counts of the targeted molecules, as well as the correction of non-linear behavior of affinity-based probes at low substrate concentrations in single cells. Standard curves are necessary for pooling data points from different experiments together because the evolution of technology and any variance of experimental procedures can be corrected by the corresponding standard curves.

It is important to note that standard curves have to be concurrent with the actual measurements and have to undergo the same experimental conditions as the measured quantities of interest in the unknown samples. In fixed samples, it is difficult or impossible to construct standard curves. For example, fixation-based solid tissue methods such as immunofluorescence and array tomography (Micheva and Smith, 2007, Neuron 55:25-36) do not allow the construction of concurrent standard curves. In fixed samples, only signals can be seen, but the underlying quantities and/or quantity differences generally cannot be determined.

All fixation-based methods usually suffer from the unpredictable molecular modification of the original sample and from the lack of standard curves. As a consequence of these two major limitations, and as a consequence of the fact that most solid-tissue methods are fixation-based, it has not been possible to date to measure the quantities of native proteins in single cells of solid tissues or to do so in a multiplex manner. It has also not been possible to measure the quantities of metabolites in single cells of solid tissues or to reliably multiplex transcripts in single cells of solid tissues. Multiplexing across molecular classes (proteins, transcripts, metabolites) in single cells of solid tissues has also not been possible.

Although it has been suggested that it is not necessary to measure true quantities or quantity differences to make informative qualitative observations in biology, in reality the correct quantities and quantity differences, as opposed to simply "signals", are integral to making correct qualitative observations. FIGS. 1 and 2 demonstrate the importance of having concurrent standard curves of affinity-based probes in order to make accurate qualitative observations about the presence or absence of sub-populations in any population measurement (single cells, tissue samples or patients). Given the same true hidden distribution of a quantity of interest across a population, a linear standard curve with a small slope will make this distribution look narrower. In contrast, a linear standard curve with a large slope will make this same true hidden distribution look broader. Given two different affinity-based probes (antibodies for example) with different KD values, and thus with different slopes of their standard curves and given the same true hidden distribution of a quantity, the above-described differences in the observed distributions solely due to the different KD values of the two probes are recorded, although the underlying true distribution of the quantity of interest is the same. Thus, qualitative observations, whether about how broad or how narrow different quantities are distributed in a population, are impossible without the knowledge of the corresponding standard curves.

At the single-cell level, many quantities of proteins, transcripts, or metabolites are present in small numbers, which can result in the non-linearity of the standard curves of the corresponding affinity-based probes. Fixation-induced differential extraction and modification of target molecules also likely result in the non-linearities of the standard curves. FIG. 2 shows how false qualitative observations about the presence or absence of a sub-population can be made in a population measurement if the underlying unknown standard curves are non-linear. Taken together, without knowing the concurrent standard curves of the applied affinity-based probes, it cannot be known if the observed qualitative observations are accurate. Arguably, the lack of concurrent standard curves is the main cause of the irreproducibility and the mutual incompatibility of many biological measurements.

Limited multiplexing is the main limitation of optical methods. The limited optical spectrum leads to the inability of separating tens of signals simultaneously and therefore makes it hard to measure the multivariate molecular mechanisms in single cells by live imaging methods. All live imaging methods are based on intracellular fluorescent probes that inherently perturb the native system of the imaged live cell. For example, one common approach to image proteins in live single cells requires the fusion of GFP derivatives to the protein of interest and the subsequent expression of the resulting fused protein. This procedure is not practical in mammal solid tissues at large scale. The fusion of GFP derivatives to the protein of interest can change both the function of the protein of interest and the native state of the cell (Sigal et al., 2006, Nat. Methods 3:525-531; Landgraf et al., 2012, Nat. Methods 9:480-482; Schnell et al., 2012, Nat. Methods, 3:825-831). The overexpression of such fused proteins and their dimerization are common. The diffusion coefficient and the kinetic parameters of GFP-fused proteins also likely change. Therefore, fused GFP does not directly report the abundances and activity of native proteins. Fluorescent intracellular ion sensors are another example of how intracellular fluorescent probes perturb the native system of the imaged cell (Yasuda et al., 2004, Sci STKE. 219: p 15). Fluorescent intracellular ion sensors are chelators and thus perturb the native system of the cell by changing the native concentrations of the respective ions (such as $Ca^{2+}$).

There is a need in the art for methods that examine single cell components derived from live solid tissues where the methods preserve the components of the single cell in analytically defined or natural state. The present invention addresses this unmet need in the art.

SUMMARY OF THE INVENTION

The present invention provides a method of lysing a single cell present in a tissue. In one embodiment, the method comprises: a) identifying a cell from a tissue; b) contacting a detergent-containing lysis buffer with the intracellular space of the identified cell; c) allowing the lysis buffer to spread within the intracellular space of the identified cell for a period of time, wherein the cell is lysed from the inside of the cell; and d) collecting the lysate, wherein the lysate comprises cellular components preserved in an analytically defined and analytically accessible state that maps to the natural state in a known way.

In one embodiment, the method occurs in the absence of tissue fixation and tissue disaggregation.

In one embodiment, the isolated cell is in an organotypic culture.

In one embodiment, the lysate is collected by suctioning the lysate using a suction channel.

In one embodiment, the suction channel is a bent suction micropipette.

In one embodiment, the collected lysate is further applied to a nitrocellulose pad.

In one embodiment, a standard is also applied the nitrocellulose pad.

In one embodiment, the lysate is evaluated using an analytical method.

In one embodiment, the analytical method is selected from the group consisting of mass spectrometry, protein microarray, RT-qPCR, RNA-Seq, and MALDI-MS.

In one embodiment, the cell is part of a live solid tissue.

In one embodiment, the detergent is sodium dodecyl sulfate.

The invention also provides a method of analyzing a cell present in a tissue. In one embodiment, the method comprises: a) identifying a cell from a tissue; b) contacting a detergent-containing lysis buffer to the intracellular space of the identified cell; c) allowing the lysis buffer to spread within the intracellular space of the identified cell for a period of time, wherein the cell is lysed from the inside of the cell; d) collecting the lysate, wherein the lysate comprises cellular components preserved in an analytically defined and analytically accessible state that maps to the natural state in a known way; e) applying the collected lysate to a solid support; and f) evaluating the collected lysate using an analytical method.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A is an illustration of the method of organotypic cultures. A dissected slice of tissue was cultured on a porous membrane. The tissue slice took up the nutrients from underneath the membrane by capillary action (from Stoppini et al., 1991, J Neurosci Methods. 37(2): 173-182). FIG. 4B is a photograph depicting an example of a successful organotypic culture of a mouse hippocampus (GAD67-GFP strain, postnatal day 6+14 days in vitro).

FIG. 13A is a series of images depicting the method of enriching the proteins of a single-cell lysate within a 20-60 µm spot on nitrocellulose. The frame on the right shows the extent of solvent spreading. However, the proteins of the single-cell lysate partition were enriched within a much smaller region right below the micropipette used for printing. The same micropipette was used for capillary-action-driven suction in Inside-Out Lysis. FIG. 13B is a series of images depicting spots of approximately 50 µm from the same single GFP-expressing somatostatin interneuron (organotypic hippocampal slice of a GIN mouse). Spots were printed on a nitrocellulose pad next to each other (10 depositions per spot). The corresponding baseline spots were also printed on the same nitrocellulose pad (10 depositions per spot). There was no signal before antibody incubation. As expected, there were signals only in the lysate spots after antibody incubation. The bar in low resolution frames is 42 µm.

FIG. 19A is a series of graphs depicting Single-Cell Lysate Microarray data. FIG. 19B is a series of graphs depicting Single-Cell Lysate Microarray data. FIG. 19C is a series of graphs depicting Single-Cell Lysate Microarray data. The obtained single-cell lysates and their baselines were printed on a nitrocellulose pad as described elsewhere herein, but without sub-partitioning. The integrated values are depicted in FIG. 20.

FIG. 22A is a series of graphs depicting the same titration series (the same 4 spots), printed by the high-precision Aushon Arrayer 2470, revealing two standard curves with different slopes for each GFP antibody. Both GFP antibodies were applied simultaneously in the total mixture of 8 antibodies. Because the lanthanide conjugation procedure was the same for each GFP antibody and because the concentration of either GFP antibody was the same during the incubation procedure, it is believed that this difference in slopes parameterizes the corresponding differences in the KD values of the two GFP antibodies. FIG. 22B is a series of graphs depicting almost perfect correlation between the in vivo GFP fluorescence and the measured GFP levels in Single-Cell Lysate Microarrays across all the sampled single cells of FIG. 19. The two dark CA3 neurons are represented by the two lowest data points. The four GFP-expressing somatostatin interneurons are represented by the other four data points. The GFP titration series in FIG. 22A was printed on the same nitrocellulose pad as single-cell lysates in FIG. 22B. Again, all titration series were printed by the high-precision Aushon Arrayer 2470. All single-cell lysates and the corresponding baselines were printed as described elsewhere herein but without sub-partitioning.

DETAILED DESCRIPTION

Figure 1:
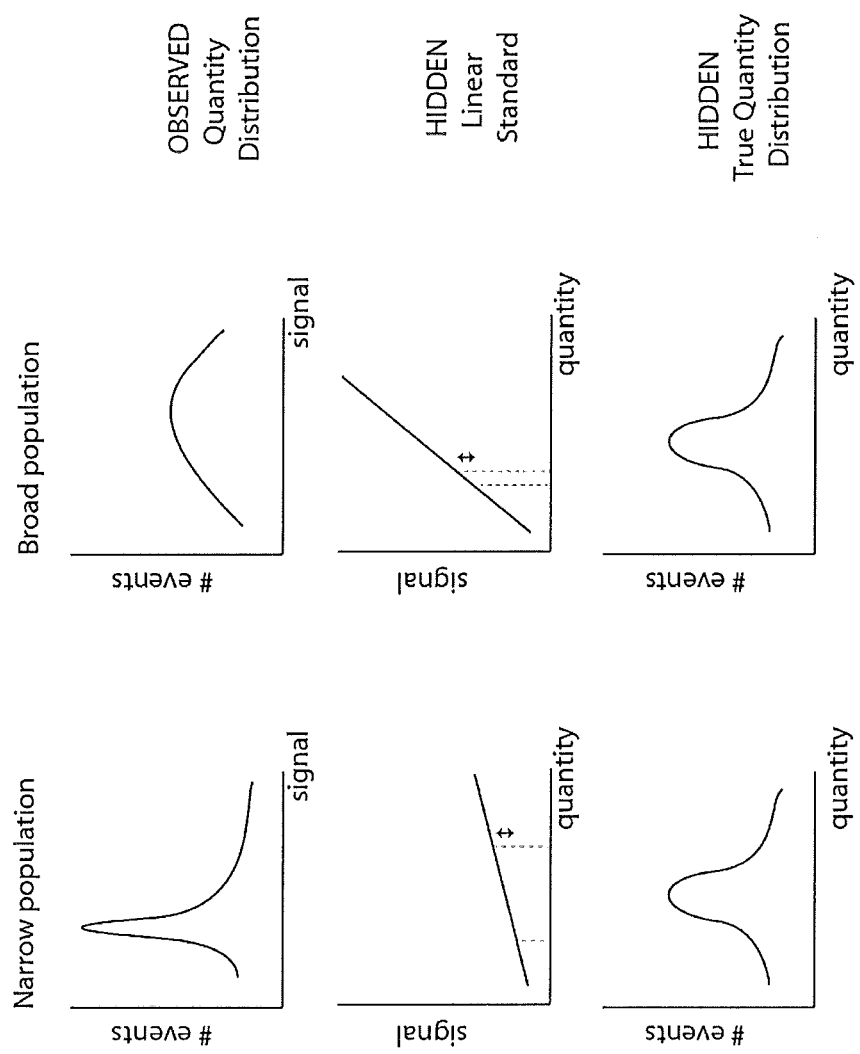
FIG. 1 is a series of graphs depicting the different slopes of linear standard curves. The true hidden distribution is shown in the bottom row. The distributions in the upper row were obtained by applying the standard curves in the middle row to the true hidden distributions in the bottom row. Different KD values of affinity based probes, such as antibodies, led to different slopes of their standard curves even at the same probe concentrations. The arrows next to the standard curves indicate that the same signal difference can be mapped to a large quantity difference or to a small quantity difference depending on the slope of the underlying standard curve.

The present invention relates to the development of a lysis technology and analytical technology as well as analytical strategies to provide the capability of sampling and evaluating single cell lysates from a solid tissue. In one embodiment, the invention comprises a sampling procedure that allows for obtaining a single cell lysate and analyzing the lysate by interfacing it with different analytical methods. Preferably, the analytical methods are based on a lysate format. For example, the analytical methods include but are not limited to solid support methods (e.g., microarrays, MALDI), non-solid support methods (e.g., qPCR or other Mass Spec modes with direct introduction of the sample), and the like.

One benefit of the invention is that the lysis protocol preserves all cellular molecules in an analytically defined and analytically accessible state that maps to the natural state in a known way thereby allowing for a more accurate and highly multiplex measurement of the cellular molecules as they existed in the cell. In one embodiment, the invention provides a method for analyzing cellular molecules from a single cell comprising: 1) lysing a single cell (e.g., lysing step), 2) applying the lysate onto a solid support (e.g., printing step), and 3) analyzing the lysate using a desired technology (e.g., analytical step).

The methods of the invention also allow for the isolation of lysate from a single cell embedded in a solid tissue while preserving the analytically defined and analytically accessible state of molecules that maps to the natural state within the cell in a known way, and therefore allow for transformation of a single target cell in a tissue sample into a format that can be evaluated using analytical methods including, but not limited to, mass spectrometry, lysate microarrays, protein microarrays, RT-qPCR, RNA-Seq, LA-ICP-MS, MALDI-MS, and the like.

In one embodiment, the invention provides an "inside-out lysis" platform comprising: 1) facilitating entry of a detergent-containing lysis buffer into the intracellular space of a target cell through a focal entry point in the cell membrane, 2) allowing the lysis buffer to spread throughout the intracellular space, 3) lysing the target cell from inside, thus providing the highest possible single-cell resolution for the lysis of target cells of any shape within the complex environment of a living tissue. This lysis technology highlights the unusual directionality of the lysis process that enables a superior spatial resolution when compared to prior art methods. The "inside-out lysis" method of the invention preserves the natural state of the single cell within the lysate in a known way, which can then be examined using a variety of analytical methods. The method of the invention also preserves RNA transcripts, proteins and metabolites by incorporating the technical advantages of detergent-based lysis.

Thus, the invention described herein relates to a new method for lysing a single cell that is derived from a solid tissue while preserving the molecules within the cell in analytically defined and analytically accessible state that maps to their natural state in the cell in a known way. The method comprises a lysis step, wherein the target cell is lysed from inside, thus providing the highest possible single-cell resolution for the lysis of target cells of any shape within the complex environment of living tissue, and collecting the lysate. In one embodiment, the target cell is encompassed in an organotypic culture. In one embodiment, the lysate is collected by suctioning the lysate out of the system with a suction channel. In one embodiment, the method comprises a printing method comprising applying the lysate to a solid support (e.g., glass-mounted nitrocellulose pad). In one embodiment, the method comprises evaluating the printed lysate using analytical measurements.

The invention described herein also relates to new analytical methods for a multiplex analysis platform where the products of the lysis method disclosed herein are analyzed. In one embodiment, the method comprises an analytical method for multiplexing analytical measurements of native proteins. In one embodiment, the method comprises applying a mixture of antibodies to the lysate printed or otherwise spotted on the solid support (e.g., nitrocellulose). In another embodiment, the antibodies are conjugated to lanthanide metals. In another embodiment, the method comprises a set of compatible analytical strategies for multiplex measurements of transcripts and metabolites in single cell lysate.

The invention also provides methods for measuring proteins, transcripts and/or metabolites at one time. Concurrent standard curves can be determined in all measurements and signals can be mapped to the corresponding quantities of the proteins, transcripts and/or metabolites being assessed.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "analyte," as used herein refers to any substance or chemical constituent that is undergoing analysis. For example, an "analyte" can refer to any atom and/or molecule; including their complexes and fragment ions. The term may refer to a single component or a set of components. In the case of biological molecules/macromolecules, such analytes include but are not limited to: polypeptides, polynucleotides, proteins, peptides, antibodies, DNA, RNA, carbohydrates, steroids, and lipids, and any detectable moiety thereof, e.g., immunologically detectable fragments.

"Assay," "assaying" or like terms refers to an analysis to determine, for example, the presence, absence, quantity, extent, kinetics, dynamics, or type of a cell's response upon stimulation with an exogenous stimuli, such as a ligand candidate compound or a viral particle or a pathogen.

"Biosensor" or like terms refer to a device for the detection of an analyte that combines a biological component with a physicochemical detector component. The biosensor typically consists of three parts: a biological component or element (such as tissue, microorganism, pathogen, cells, or combinations thereof), a detector element (works in a physicochemical way such as optical, piezoelectric, electrochemical, thermometric, or magnetic), and a transducer associated with both components. The biological component or element can be, for example, a living cell, a pathogen, or combinations thereof. In embodiments, an optical biosensor can comprise an optical transducer for converting a molecular recognition or molecular stimulation event in a living cell, a pathogen, or combinations thereof into a quantifiable signal.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of more than one type of cells (or differentiated forms of a single type of cell), which interact with each other, thus performing a biological or physiological or pathophysiological function. Such cell system includes an organ, a tissue, a stem cell, a differentiated cell, or the like.

As used herein, the term "cellular constituent" comprises individual genes, proteins, mRNA, RNA, and/or any other variable cellular component or protein activity, degree of protein modification (e.g., phosphorylation), for example, that is typically measured in a biological experiment by those skilled in the art.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

One of the greatest challenges in the post-genomic era is the development of methods that can reliably analyze the transcripts, metabolites, proteins as well as posttranslational modification states of different proteins in a single cell lysate obtained with high spatial and temporal resolution from complex, living tissue and from complex tissue in general.

The present invention relates to the development of a microlysis technology and analytical technology as well as analytical strategies to provide the capability of sampling and evaluating single cell lysates from a live solid tissue while preserving all cellular molecules in an analytically defined and analytically accessible state that maps to the natural state in a known way. In one embodiment, the invention provides a method for analyzing cellular molecules from a single cell comprising: 1) lysing a single cell (e.g., sampling), 2) applying the lysate on a solid support (e.g., printing), and 3) analyzing the lysate using a desired technology.

Accordingly, the invention provides compositions and methods that enable proteomic studies on single cell lysates derived from physiologically relevant, complex, living tissue. However, the invention should not be construed to be limited solely to proteomic studies. Rather, the single cell lysate can be used in any assay to evaluate nucleic acids, polypeptides and any metabolites. That is, after the single cell lysate is obtained and printed on a solid support according to the invention by way of multiplexing proteins in one single spot without sample subdivision by using a 'labeling—label detection method' pair for example the 'lanthanide labeling—LA-ICP-MS detection' pair. In some instances, the methods of the invention include the use of cell-based assays, protein-based assays, and DNA-based assays. In one embodiment, when such technologies are applied to analyzing the lysate of the invention, the results obtained therefrom depict the natural state of the cellular components as represented in the single cell.

In one embodiment, the invention comprises an "Inside-Out Lysis" methodology providing for a single cell in a live solid tissue to be lysed to provide a lysate that comprises cellular molecules of all classes of molecules that are preserved in analytically defined and analytically accessible state that maps to the natural state in a known way. The "Inside-Out Lysis" methodology of the invention is contrary to the common practice in the art where cells or tissues have been submerged in a solubilizing/dissociation solution and thus the directionality of solubilization/dissociation process of methodologies in the art is from the outside. A more detailed discussion of the Inside-Out Lysis method of the invention is discussed elsewhere herein.

In another embodiment, the invention provides an analytical method for multiplexing analytical measurements of native proteins present in a single cell lysate. This method is referred herein as a "Single-Cell Lysate Microarray." A more detailed discussion of the Single-Cell Lysate Microarray method of the invention is discussed elsewhere herein. In one embodiment, this method provides a set of compatible analytical strategies for multiplex measurements of transcripts and metabolites in a single cell lysate.

Lysis Step

The invention provides a method for obtaining lysate from a single cell which is referred herein as a single cell lysate. In one embodiment, the single cell lysate is of small volume (e.g., about 10 nl). The lysate format of the single cell can be exploited by interfacing it with different analytical methods that are based on the lysate format.

In one embodiment, the invention provides a method of lysing a single cell that is embedded in a tissue, preferably a solid tissue, more preferably a live solid tissue. In one embodiment, the invention provides an "Inside-Out Lysis" platform for lysing a single cell from a tissue sample wherein the lysate can be further analyzed using any desired analytical method. For example, a single cell is lysed according to the "inside-out lysis" method of the invention, followed by printing or otherwise spotting the lysate on a solid support, and the printed lysate is analyzed using a desired protocol.

In one embodiment, the lysis method of the invention employs detergent-based single-cell lysis buffer. An advantage of using a detergent-based lysis buffer over a fixation method is that the state of the proteins in the lysate is analytically defined. For example, an SDS lysis buffer denatures proteins and kills their activity whereas NP40 does not denature proteins. In both cases, the state of the proteins is known because the effects of the lysis buffer on the molecules are known and therefore the state is analytically defined (unlike fixation methods). Also all molecules can be accessed analytically (unlike fixation methods) using the lysis protocol of the invention.

Detergents are amphipathic molecules, meaning they contain both a nonpolar "tail" having aliphatic or aromatic character and a polar "head." Ionic character of the polar head group forms the basis for broad classification of detergents; they may be ionic (charged, either anionic or cationic), nonionic (uncharged) or zwitterionic (having both positively and negatively charged groups but with a net charge of zero). In any event, detergent molecules allow the dispersion (miscibility) of water-insoluble, hydrophobic compounds into aqueous media, including the extraction and solubilization of membrane proteins. Both the number of detergent monomers per micelle (aggregation number) and the range of detergent concentration above which micelles form (called the critical micelle concentration, CMC) are properties specific to each particular detergent.

In one embodiment, the lysis method involves the following sequence of events: 1) detergent-containing lysis buffer enters the intracellular space of the target cell through a focal entry point in the cell membrane, 2) lysis buffer spreads throughout the intracellular space, 3) and the target cell is lysed from the inside, thus allowing the highest possible single-cell resolution for the lysis of target cells of any shape within the complex environment of living tissue.

Thus, the invention described herein relates to a new method for lysing a single cell that is derived from a solid tissue while preserving all cellular molecules in an analytically defined and analytically accessible state that maps to the natural state in a known way. The method comprises a lysis step comprising adding detergent-containing lysis buffer to the intracellular space of the target cell in a system through a focal entry point in the cell membrane, allowing the lysis buffer to spread throughout the intracellular space of the target cell over a period of time, wherein the target cell is lysed from inside, thus providing the highest possible single-cell resolution for the lysis of target cells of any shape within the complex environment of living tissue, and collecting the lysate. In one embodiment, the target cell is encompassed in an organotypic culture.

In one embodiment, a focally directed flow of the detergent-containing lysis buffer is applied to the cell body of the target cell in a live tissue. Preferably, the concentration of the detergent used is above its critical micellar concentration (CMC) value. This property enables the applied lysis buffer to enter the intracellular space without spilling to the adjacent cells in the tissue. Inside the cell, the detergent is diluted to a concentration value that is below its CMC value, allowing the lysis buffer to accumulate in the intact intracellular space and to diffuse and/or to flow throughout the complex shape of the target cell without affecting its complex tissue surroundings. Once enough lysis buffer has accumulated inside the target cell and the detergent concentration re-approaches its critical value, the cell membrane is lysed from inside and the lysate can be immediately diluted and up-taken in a nearby suction channel. In one embodiment, it is preferred that the lysate be immediately diluted so that it does not affect other cells once the membrane barrier of the target cell is broken. Thus the Inside-Out Lysis method is able to convert a single live cell of any shape in a complex solid tissue into a mixed lysate solution where all classes of molecules are preserved. In one embodiment, the volume of the obtained single-cell lysate is approximately 1-500 nL, preferably 2-250 nL, more preferably 3-100 nL, more preferably 4-50 nL, and most preferably 5-10 nL.

In one embodiment, the detergent-based single-cell lysis buffer comprises one or more non-ionic detergents, including, but not limited to, N-octyl-β-D-glucopyranside, N-octyl-β-D-maltoside, ZWITTERGENT 3.14, deoxycholate; n-Dodecanoyl sucrose; n-Dodecyl-β-D-glucopyranoside; n-Dodecyl-β-D-maltoside; n-Octyl-β-D-glucopyranoside; n-Octyl-β-D-maltopyranoside; n-Octyl-β-D-thioglucopyranoside; n-Decanoylsucrose; n-Decyl-β-D-maltopyranoside; n-Decyl-β-D-thiomaltoside; n-Heptyl-β-D-glucopyranoside; n-Heptyl-β-D-thioglucopyranoside; n-Hexyl-β-D-glucopyranoside; n-Nonyl-β-D-glucopyranoside; n-Octanoylsucrose; n-Octyl-β-D-glucopyranoside; n-Undecyl-β-D-maltoside; APO-10; APO-12; Big CHAP; Big CHAP, Deoxy; BRIJ® 35; $C_{12}E_5$; $C_{12}E_6$; $C_{12}E_8$; $C_{12}E_9$; Cyclohexyl-n-ethyl-β-D-maltoside; Cyclohexyl-n-hexyl-β-D-maltoside; Cyclohexyl-n-methyl-β-D-maltoside; Digitonin; ELUGENT™; GENAPOL® C-100; GENAPOL® X-080; GENAPOL® X-100; HECAMEG; MEGA-10; MEGA-8; MEGA-9; NOGA; NP-40; PLURONIC® F-127; TRITON® X-100; TRITON® X-114; TWEEN® 20; or TWEEN® 80. Additionally, an ionic detergent can be used with the methods of the invention, including, but not limited to BATC, Cetyltrimethylammonium Bromide, Chenodeoxycholic Acid, Cholic Acid, Deoxycholic Acid, Glycocholic Acid, Glycodeoxycholic Acid, Glycolithocholic Acid, Lauroylsarcosine, Taurochenodeoxycholic Acid, Taurocholic Acid, Taurodehydrocholic Acid, Taurolithocholic Acid, Taurursodeoxycholic Acid, and TOPPA. Zwitterionic detergents can also be used with the compositions and methods of the invention, including, but not limited to, amidosulfobetaines, CHAPS, CHAPSO, carboxybetaines, and methylbetaines. Anionic detergents can also be used with the compositions and methods of the invention, including, but not limited to, e.g. SDS, N-lauryl sarcosine, sodium deoxycholate, alkylaryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, and sucrose esters.

Generally any suitable liquid may be used as a solvent in the lysis buffer of the present invention. The liquid may be organic or inorganic and may be a pure liquid, a mixture of liquids or a solution of substances in the liquid and may contain additional substances to enhance the properties of the solvent. Any liquid that is suitable for solubilizing the cellular components of body samples in total or in parts may be regarded as a lysis buffer as used herein.

In one embodiment, the solvent is designed, so that cells, cell debris, nucleic acids, polypeptides, lipids and other biomolecules potentially present in the sample are dissolved. In further embodiments of the present invention, the solvent may be designed to assure differential lysis of specific components of the body sample, leaving other components undissolved.

In some instances, the lysis buffer of the invention comprises one or more agents that prevent the degradation of components within the sample. Such components may for example comprise enzyme inhibitors such as proteinase inhibitors, RNAse inhibitors, DNAse inhibitors, nuclease (e.g. endonucleases and exonucleases) inhibitors, etc. Proteinase inhibitors may e.g. comprise inhibitors of serine proteinases, inhibitors of cysteine proteinases, inhibitors of aspartic proteinases, inhibitors of acidic proteinases, inhibitors of alkaline proteinases or inhibitors of neutral proteinases. Preferably, the lysis buffer comprises a cocktail of irreversible and reversible protease, phosphatase and RNAse inhibitors.

In addition one or more enzymes such as zymolyase, lyticase, lysozyme or lysostaphin; one or more inorganic salts such as sodium chloride, potassium chloride, or lithium chloride; one or more acids and/or bases or buffering agents (e.g., to increase or reduce pH); or any other compound or enzyme which may assist in the disruption of the integrity of (i.e., lyses or causes the formation of pores in) the cell membrane and/or cell walls (e.g., polymixin B) can be used.

The lysis method of the invention can be applied to any single cell type or a mixture of cell types. The invention is suitable for use with any cell type, including primary cells, biopsy tissue, normal and transformed cell lines, transduced cells and cultured cells, each of which can be single cell types or cell lines; or combinations thereof.

Preferably, the single cell is isolated from a tissue. The tissue may be derived from all sources, particularly mammalian, and with respect to species, e.g., human, simian, rodent, etc. The tissue origin can be from heart, lung, liver, brain, vascular, lymph node, spleen, pancreas, thyroid, esophageal, intestine, stomach, thymus, etc. The invention should not be limited to the cell type or tissue type. Rather, the invention should be construed as being applicable to any cell and any tissue. Also, artificially constructed 3-D tissue-like structures designed and constructed by tissue engineering are applicable.

For example, the invention is useful to examine cell types that include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and genetically modified cells thereof.

The Inside-Out Lysis method of the invention has advantages over prior art methods in that the method does not require tissue fixation/permeabilization and tissue disaggregation.

In one embodiment, Inside-Out Lysis is completely automated, as described elsewhere herein. In another embodiment, Inside-Out Lysis is user-driven with partial automation. In another embodiment, Inside-Out Lysis is completely user-driven.

Printing Step

After the lysing step, the lysate can be collected by suctioning the lysate using a suctioning channel and the lysate can then be applied (i.e. printed or spotted) onto a solid support whereby the lysate can be evaluated using the desired technology. Prior art methods for printing (e.g., piezo-driven printing and contact printing) are not appropriate for use with the dilute lysates of the invention because the solvent area in prior art methods is almost the same as the analyte area, and therefore resulting in less solvent evaporation per unit time. Prior art methods are also not appropriate for use with small volumes because the prior art drop delivery process is not a continuous delivery process. A drop delivery process results in less solvent evaporation per unit time and therefore a longer time to print the entire sample by repeating depositions onto the same spot, which results in a large part of the small sample volume evaporating before contacting solid support. That is, the prior art printing methods are not appropriate for printing diluted single cell lysates of small volumes (e.g., about 5-15 nl, preferably about 10 nl).

Accordingly, the invention provides a novel printing for use with small volumes. In one embodiment, the capillary component of the printing method of the invention does not have to necessarily contact the solid support but has to be close enough to ensure continuous delivery. This method is appropriate for dilute lysates of the invention because for example, solvent area is 10-100 times larger than the analyte area, which results in more solvent being removed by evaporation per unit time during continuous delivery of the lysate onto a solid support. Preferably the solid support is porous having a higher affinity to the analyte compared to the solvent. In another embodiment, the capillary component of the printing method of the invention is appropriate for small volumes because the continuous delivery within each deposition results in more diluted sample being deposited within each deposition, thereby fewer depositions are necessary which allows for only a small part of the small sample volume evaporating before contacting the solid support. Accordingly, the printing method of the invention is appropriate for printing dilute single cell lysate of small volumes (e.g., 5-15 nl, preferably about 10 nl).

In one embodiment, the printing method of the invention is appropriate for use with the diluted single cell lysates of small volume that contained limited analyte of the invention. In one embodiment, the printing method allows for the enrichment of the analyte on a porous solid support (e.g., nitrocellulose). Preferably, the enrichment/printing method includes using any porous solid support that has a higher affinity for an analyte and a smaller affinity to the solvent or to a non-analyte.

In one embodiment, the present invention provides a method of releasing the intracellular contents of at least one cell of a cell-containing fluid sample for analysis. For example, the lysate generated from using the Inside-Out Lysis of the invention can be spotted on a substrate for analysis. In one embodiment, the invention provides a microfluidic system for transport and lysis of at least one cell of a cell-containing fluid sample.

In one embodiment, a customary bent glass micropipette having about 10 µm aperture is used to take up the single-cell lysate. In some instances, the aperture is about 9 µm about 8 µm about 7 µm about 6 µm about 5 µm about 4 µm about 3 about 2 µm about 1 µm. In one embodiment, the aperture is 1.5 µm or smaller.

In order to analyze the protein content of each single cell, each single-cell lysate so taken up is printed on a solid support. In some instances, the solid support is a mobilizable material (such as a metal sol or beads made of latex or glass) or an immobile substrate (such as glass fibers, cellulose strips or nitrocellulose membranes). Preferably, the solid support is a glass-mounted nitrocellulose pad.

In one embodiment, the invention provides one or more reservoirs for delivery or collection of a test sample, diluent, reagent or the like. The microfluidic devices and systems used in practicing this invention can be made using a variety of substrate materials, including glass, fused silica and various polymeric materials, such as PDMS or combinations of such materials.

The invention includes any surface to which the cell lysate of the subject invention is attached, where the cell lysate or fractions thereof are attached in a pre-determined spatial array of arbitrary shape.

A variety of solid supports or substrates are suitable for the purposes of the invention, including both flexible and rigid substrates. By flexible is meant that the support is capable of being bent, folded or similarly manipulated without breakage. Examples of flexible solid supports include acrylamide, nylon, nitrocellulose, polypropylene, polyester films, such as polyethylene terephthalate, etc. Also included are gels, e.g. collagen gels, matrigels, and ECM gels. Rigid supports do not readily bend, and include glass, fused silica, quartz, plastics, e.g. polytetrafluoroethylene, polypropylene, polystyrene, polycarbonate, and blends thereof, and the like; metals, e.g. gold, platinum, silver, and the like; etc.

The substrates can be formed in a variety of configurations, including filters, fibers, membranes, beads, particles, dipsticks, sheets, rods, etc. Usually, a planar or planar three-dimensional geometry is preferred. The materials from which the substrate is fabricated should ideally exhibit a low level of non-specific binding during binding events, except for specific cases in which some non-specific binding is preferred.

In some embodiments, the solid support, is porous and can be, for example, nitrocellulose (including pure nitrocellulose and modified nitrocellulose). The nitrocellulose can be the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support.

In one embodiment, the properties of porous solid support materials enable fast-binding of analyte molecules. In some instances, this fast binding of analyte molecules by the porous solid support material is used for enrichment of analyte molecules (e.g. proteins) within the geometric confinements of a small (e.g., about 5-100 micron) dense spot on porous solid support. Prior art methods do not enable single cell lysate printing on porous solid support in dense spots (e.g., signals derived from this spot are significantly above the noise and background levels of the solid support material). In one embodiment of the invention, the diluted lysate is repeatedly spotted on the same spot of solid support such that the solvent radially spreads to an area many times larger than the area where analyte is retained by fast binding to porous solid support material. The solvent then evaporates while the analyte is retained within the small dense spot of porous solid support. After solvent evaporation, the deposition of diluted lysate is repeated onto the same spot in the above manner. Such enrichment enables the reconcentration of the dilute single cell lysate on porous solid support, as described elsewhere herein. The reconcentration of the analytes in the small dense spot makes the contributions of solid support substance to the overall recorded signal in the analytical step negligible. This enrichment process and thus the ability to print single cell lysate in a dense spot on porous solid support, allows for the analysis of analytes from a single cell lysate (e.g., the Single-Cell Microarray format).

In one embodiment, the invention includes the use of a standard curve. Without wishing to be bound by any particular theory, when choosing a target, it is useful to look for a protein that is most up-regulated or down-regulated relatively to all other proteins in a given pathological sample. Because the slopes of standard curves vary across different affinity-based probes (such as antibodies), measured 'signals' lead to false choices of protein targets. Measured quantities, determined by applying the corresponding standard curves to signals, lead to correct choices of protein targets. Thus, qualitative observations, whether the up-regulation or down-regulation of one molecule is more significant than the up-regulation or down-regulation of another molecule, are impossible without the knowledge of the corresponding standard curves.

In one embodiment, the lysates and standard curves are printed on a solid support (e.g., nitrocellulose pad), as described elsewhere herein.

The standard curves of purified recombinant proteins and/or control lysates can be printed next to the printed spots of single cell lysates on the same nitrocellulose pad or on another solid support. This strategy enables the construction of standard curves for each dimension of the multiplex measurement. This strategy enables the construction of several identical standard curves on the same solid support in order to estimate the noise levels and to determine the limit of detection. This strategy enables the mapping of signals recorded from single cell lysates onto the concurrent standard curves. In one embodiment, the standard curve is printed with conventional Arrayer because standard curves can be constructed from large amounts of material. Therefore in some instances, the diluted single cell lysate is printed according to the novel printing method of the invention and standard curves are printed in a conventional way on the same solid support. In this aspect, the overall printing procedure includes two printing methods and is different from the printing method used in conventional lysate microarrays.

In one embodiment, the method of the invention enables the determination of the noise levels of single cell for each dimension of a multiplex single cell measurement. This strategy enables the determination the signals of any measured dimension of the multiplex measurement are above the limit of detection.

If combined with the appropriate 'labeling—detection method' pair (for example lanthanide labeling and LA-ICP-MS are 'labeling—detection method' pair, as discussed elsewhere herein), this strategy eliminates the disadvantages of prior art methods in that the present invention does not require the sub-fractioning of the limited single-cell material for the purpose of multiplexing. For example, lanthanide labeling combined with LA-ICP MS eliminates the need for subfractioning of the limited sample. This is because in the Single-cell Lysate microarray of the invention, many antibody labels from one spot with the precious sample deposited in this one spot can be read out by LA-ICP-MS. This strategy also eliminates the disadvantages of prior art methods in that the present invention does not require tissue fixation/permeabilization and tissue disaggregation.

At the same time, this strategy incorporates the advantages. Namely, this strategy enables the printing of concurrent standard curves, the rigorous validation of antibody probes and other affinity-based probes as in a microarray, as discussed elsewhere herein. This strategy can be combined any label-label detection method pair applied to solid supports. For example, the pair of lanthanide-labeling of antibodies and LA-ICP-MS detection can be applied, as described elsewhere herein.

In one embodiment, the solid support can be pre-printed with the matrix for MALDI analysis.

In one embodiment, the solid support (e.g., glass) is prepared by covalently linking other molecular entities to it before the application of the lysate. Such molecules include but are not limited to: antibodies, enzymes, protein domains.

The lysate can also be released into a fluid for further analysis. The lysate can then be analyzed after being released into a fluid by analytical methods. Lysates can be pooled together into one fluid volume. For example, the lysates from cells of a cell type can be combined in one fluid volume (e.g., another buffer) in order to increase the total analyte content. By pooling many lysates together into one fluid volume, the analysis by analytical methods with higher sample requirements can be achieved. The fluid volume with pooled lysates can also be concentrated by evaporation.

The lysate can be applied to an analytical device (e.g., the mass spectrometer) without prior printing on solid support or prior releasing it into a fluid.

Analytical Step

The Inside-Out Lysis method of the invention facilitates the sampling of a single-cell lysate obtained from a live solid tissue with high temporal and spatial resolution. The Inside-Out Lysis enables analysis of the "complete molecular state" in each sampled single cell, because the lysate format enables the analysis within and across any classes of molecules. The mixed lysate can be subdivided into parts, such that each part is analyzed with a different method. The entire lysate can also be analyzed with just one analytical method. Alternatively, the entire lysate can be analyzed with one method and then analyzed with another method sequentially. More than two analytical methods can be applied sequentially to the same lysate.

In one embodiment, the native proteins of the entire single cell lysate are enriched within a dense spot on porous solid support (as described in the Printing Step) and are analyzed with Single-Cell Lysate microarrays, as described elsewhere herein. More than one single cell lysate, each derived from one cell, can be analyzed on the same microarray. Unlike any prior art methods, Single-Cell Lysate Microarrays enable multiplex measurements of native proteins in single cells with concurrent standard curves.

In the context of single cell lysates, the lysate is kept in a single spot for the purpose of multiplexing proteins. Accordingly, the invention is partly based on the development of a way to multiplex proteins in one single spot without sample subdivision by using the 'lanthanide labeling—LA-ICP-MS detection' pair as the 'labeling—label detection method' pair.

In one embodiment, other 'labeling—label detection method' pairs (other than lanthanide-LA-ICP-MS) can be used in the format of Single-Cell Lysate Microarrays for detection of proteins or other molecules of other molecular classes. For example, nucleotide sequences can be conjugated to antibodies instead of lanthanide chelators and multiplexing could be achieved with RT-qPCR reaction instead of LA-ICP-MS.

In another example, mRNA is also bound to nitrocellulose and can be enriched in the same manner as proteins within a small dense spot on nitrocellulose. qPCR reaction could be run to detect abundances of mRNA.

In one embodiment, the native proteins of a partition of the single cell lysate are analyzed with Single-Cell Lysate microarrays. The other partition of the single cell lysate is analyzed with another method (e.g. RT-qPCR for transcript analysis, or MALDI for metabolite analysis) or is further subdivided into subpartitions. This process can be continued until the required number of subpartitions is prepared. Each subpartition can then be analyzed with a different analytical method. Subpartition of the lysate can be analyzed with the same analytical method in order to establish that each subpartition reliably represents the overall lysate. As analytical methods become more sensitive and as the limit of detection of analytical methods improves, more subpartitions can be generated from one single cell lysate and analyzed with different analytical methods.

In one embodiment, the invention allows for multiplexing across molecule classes. For example, the lysate of the invention can be subdivided. In this situation, subdividing for the purpose of using different analytical methods on sub-fractions is preferred in contrast to subdividing for the sole purpose of multiplexing within a molecule class.

In other embodiments, any other analytical methods compatible with the lysate format can be used for analysis of the lysate. In addition, the lysates of single cells of a cell type can be pooled in a volume of liquid and then applied to analytical methods. In other embodiments, the lysate of single cells of a cell type can be pooled in a volume of solvent (e.g., buffer) and the concentration of analyte can be increase by solvent evaporation before applying to an analytical method. Analytical methods compatible with the lysate format include but are not limited to: mass spectrometry methods, PCR based methods, sequencing based methods etc.

The methods and compositions of the invention provide, but are not limited to one or more of the following attributes: (1) small sample and antibody requirements and (2) scalable and amenable to robotic automation and multiplexing. Expression and post-translational modifications of signaling proteins can be probed on a single support yielding quantitative expressional data on distinct proteins and the phosphorylation levels of unique modification sites.

Methods and kits are provided for a multiplexed protein microarray platform, which is utilized for simultaneous monitoring of cellular components. Of particular interest are components affected by post-translational modification, and more particularly signaling pathway components. The microarray comprises single cell lysates, where the cells are from a live tissue.

The invention permits the rapid and large-scale diagnostic screening of altered protein post translational modification (PTM) and PTM alteration states. The methods involve, in part, applying concentrated cell extracts or biological fluid samples from a single cell to different analytical tests and appropriately supplementing them to carry out one or more specific PTM or PTM alteration reactions. Specifically, one or more PTM or PTM alterations are then detected by labeling the modified proteins and scanning the array.

Covalently modified proteins, such as polyubiquitinated, ubiquitinated, phosphorylated, glycosylated, sumoylated, acetylated, S-nitrosylated or nitrosylated, citrullinated or deiminated, neddylated, OClcNAc-added, ADP-ribosylated, methylated, hydroxymethylated, fattenylated, ufmylated, prenylated, myristoylated, S-palmitoylated, tyrosine sulfated, formylated, and carboxylated proteins are hard to identify by the standard biochemical technique of gel electrophoresis, because the modified protein bands spread throughout the gel. Identifying the converse alteration of a PTM, such as, for example, deubiquitination (DUB), dephosphorylation, deglycosylation, desumoylation, deacetylation, deS-nitrosylation or denitrosylation, decitrullination or dedeimination, deneddylation, removal of OClcNAc, de-ADP-ribosylation, demethylation, de-hydroxylation, defattenylation, deufmylation, deprenylation, demyristoylation, de-S-palmitoylation, tyrosine desulfation, deformylation, decarboxylation, and deamidation is similarly difficult to detect using such standard biochemical methods. In contrast, with the present methods described herein, a PTM or PTM alteration reaction is performed directly on a solid state array or the use of multiplex formats, such as lysate microarrays, also makes possible the simultaneous analysis of thousands of proteins. Thus, the present invention overcomes previous obstacles for identifying altered PTM or PTM alteration states.

A variety of mass spectrometry systems can be employed in the methods of the invention for identifying and/or quantifying the single cell lysate. Mass analyzers with high mass accuracy, high sensitivity and high resolution include, but are not limited to, ion trap, triple quadrupole, and time-of-flight, quadrupole time-of-flight mass spectrometers and Fourier transform ion cyclotron mass analyzers (FT-ICR-MS). Mass spectrometers are typically equipped with matrix-assisted laser desorption (MALDI) and electrospray ionization (ESI) ion sources, although other methods of peptide ionization can also be used. In ion trap MS, analytes are ionized by ESI or MALDI and then put into an ion trap. Trapped ions can then be separately analyzed by MS upon selective release from the ion trap. Proteins can be analyzed, for example, by single stage mass spectrometry with a MALDI-TOF or ESI-TOF system. Methods of mass spectrometry analysis are well known to those skilled in the art (see, for example, Yates, J., 1998 Mass Spect 33:1-19; Kinter and Sherman, 2000 Protein Sequencing and Identification Using Tandem Mass Spectrometry, John Wiley & Sons, New York; Aebersold and Goodlett, 2001 Chem. Rev. 101:269-295; Banez et al, 2005 Curr Opin Urol 15:151-156). For high resolution protein separation, liquid chromatography ESI-MS/MS or automated LC-MS/MS, which utilizes capillary reverse phase chromatography as the separation method, can be used (Yates et al., 1999 Methods Mol. Biol. 112:553-569).

In one embodiment, the assay method is mass spectroscopy. Mass spectroscopy can include but is not limited to GC/MS, LC/MS, LC/MS/MS, MALDI-TOF, LC-ESI-MS/MS, MALDI-MS, tandem MS, TOF/TOF, TOF-MS, TOF-MS/MS, triple-quad MS, and triple-quad MS/MS.

In another embodiment, the single cell lysate may be analyzed using immunoaffinity based assays such as ELISAs, Western blots, and radioimmunoassays. Other methods useful in this context include isotope-coded affinity tag (ICAT) followed by multidimensional chromatography and MS/MS.

In one embodiment, the assay component of the analytical stage of the invention may be an immunoassay such as ELISA, EIA, RIA, lateral flow and flow-through formats.

In one embodiment, the single cell lysate can be assayed by applying it to RT-qPCR, RNA-Seq, MALDI-MS, among others.

The methods of the invention include detection and analysis of PTMs and as well as the expression level of the protein using any composition or agent that can be detected by spectroscopic, photochemical, biochemical, immunochemical, electrical, optical or chemical means, thus providing a detectable signal to identify the PTM protein level. A PTM and protein expression level can be detected using the methods described herein, for example, if there is a change in the average number of a given chemical group attached per protein molecule, if there is a change in the type of chemical group or groups attached per protein molecule, or if there is a different mixture of protein molecules having distinct modification patterns in a patient sample with respect to a control sample. Alteration of a PTM state of a protein includes going from an unmodified protein to a modified one and vice-versa, as well as changes in the number or type of chemical moieties added to the protein. A control sample or level is used herein to describe a control patient, control or reference data, or data obtained from the same patient at an earlier time. For example, in some embodiments, a control sample is a functional cell extract obtained from a biological sample obtained from a subject not suffering from the disease being examined in the test sample.

Accordingly, in some embodiments, an increase in the signal from a solid-state array compared to a background or the reaction with a control is indicative of increased PTM or protein expression level. The terms "increased," "increase," or "enhance" are all used herein to generally mean an increase by a statically significant amount; for the avoidance of any doubt, the terms "increased," "increase," or "enhance" mean an increase, as compared to a reference level, of at least about 10%, of at least about 15%, of at least about 20%, of at least about 25%, of at least about 30%, of at least about 35%, of at least about 40%, of at least about 45%, of at least about 50%, of at least about 55%, of at least about 60 %, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, or at least about a 10-fold increase, or any increase of 10-fold or greater, as compared to a control sample or level.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Single-Cell Sampling in Solid Tissues

The results presented herein demonstrate the successful development of a novel sampling method that allows for obtaining single-cell lysates from a live complex solid tissue having high temporal and spatial resolution.

Figure 7:
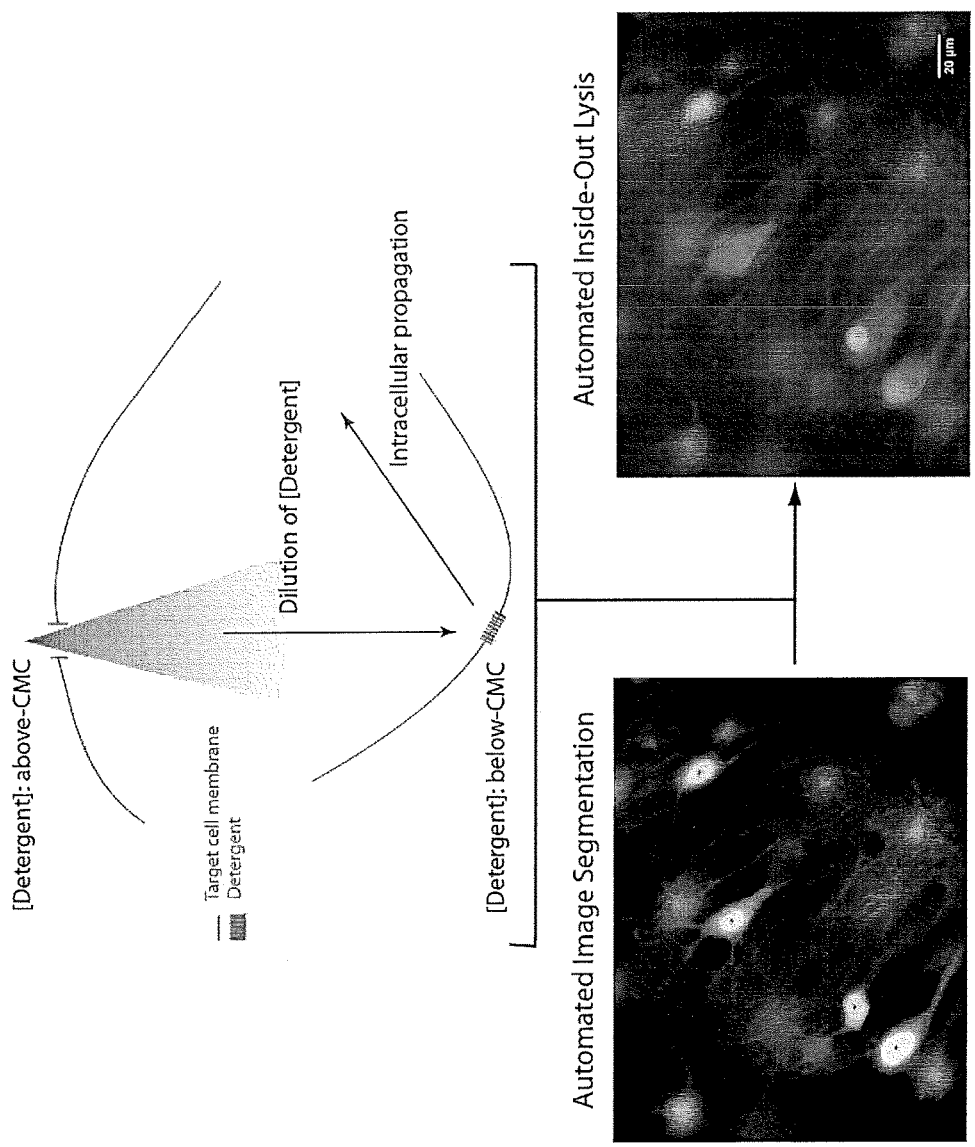
FIG. 7 is an illustration depicting the Inside-Out Lysis of single cells in a live solid tissue. The upper diagram summarizes the concept of Inside-Out Lysis. In the bottom frames, SDS-containing lysis buffer was mixed with SR101. No suction was applied. The organotypic culture of mouse hippocampus is displayed (GAD67-GFP strain, postnatal day 6+7 days in vitro). In all instances, the delivery of lysis buffer was accomplished robotically without any human input. It was observed that the second cell from the bottom had a small surface area and the applied lysis buffer entered the adjacent dark cell by flowing into it. The single-cell resolution of delivery was accurate in all other instances (also see FIG. 32). The frame on the bottom right also shows the initiation of the lysis buffer delivery to the upper cell (fourth cell).
Figure 26:
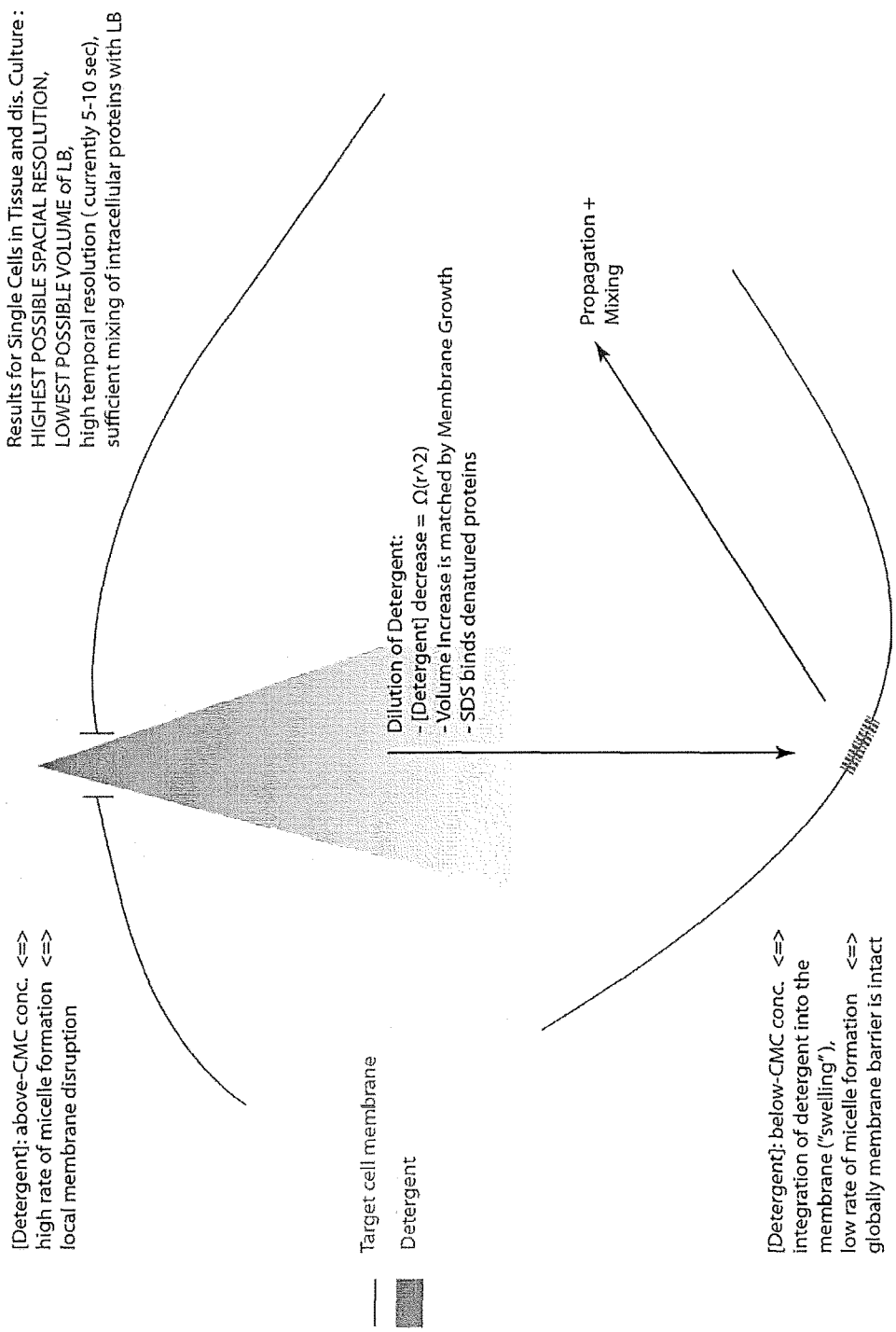
FIG. 26 is an illustration depicting a framework for Inside-Out Lysis and relations between detergent concentrations. Relations between head-group charge and hydrocarbon chain length of detergents and CMC and micelle size have been established in other biophysical studies and provide the basis for parameterization of our Inside-Out Lysis model.
Figure 27:
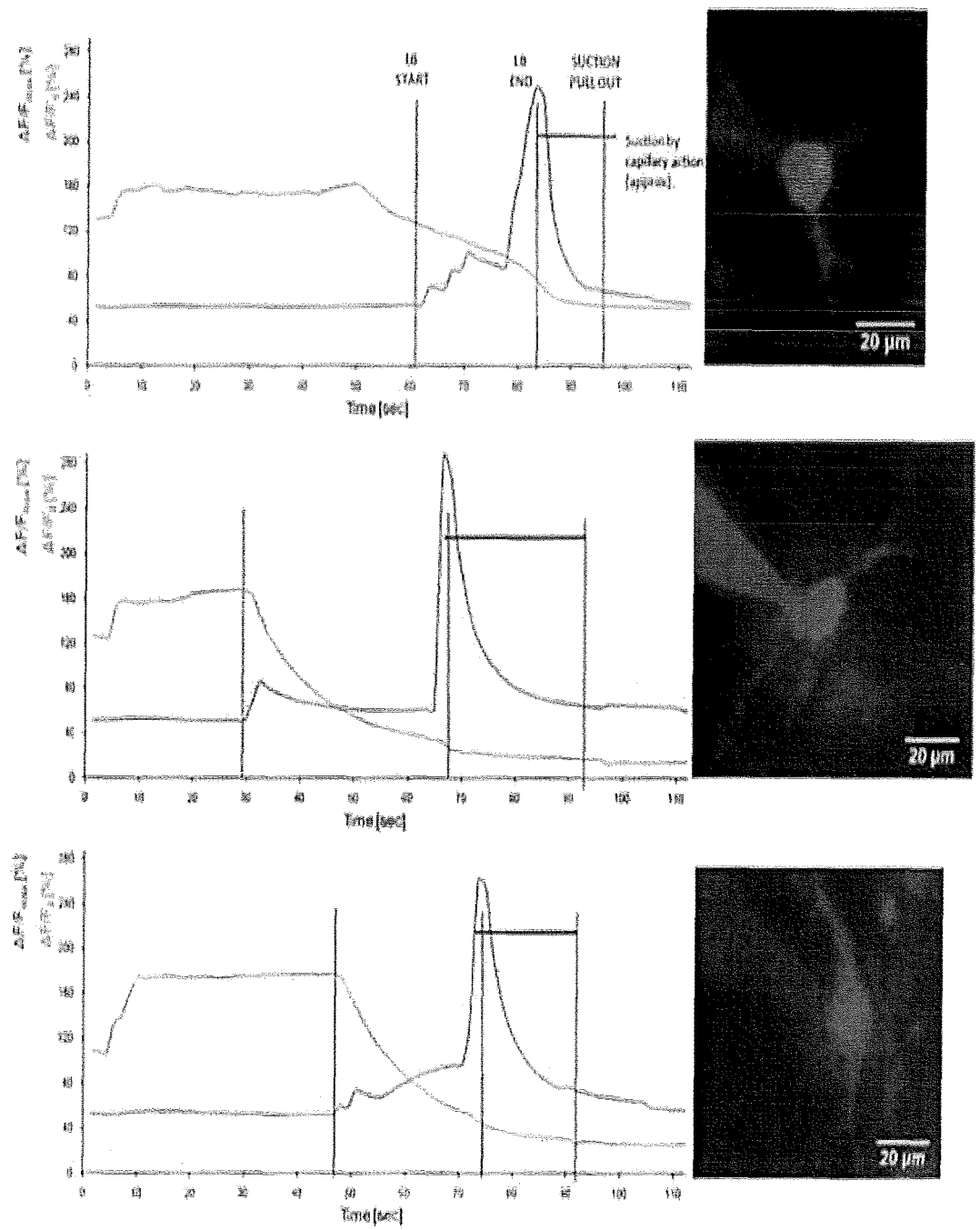
FIG. 27 is a series of graphs depicting time course of protein denaturation/cell homogenization and the breaking of the membrane barrier with subsequent lysate uptake
Figure 28:
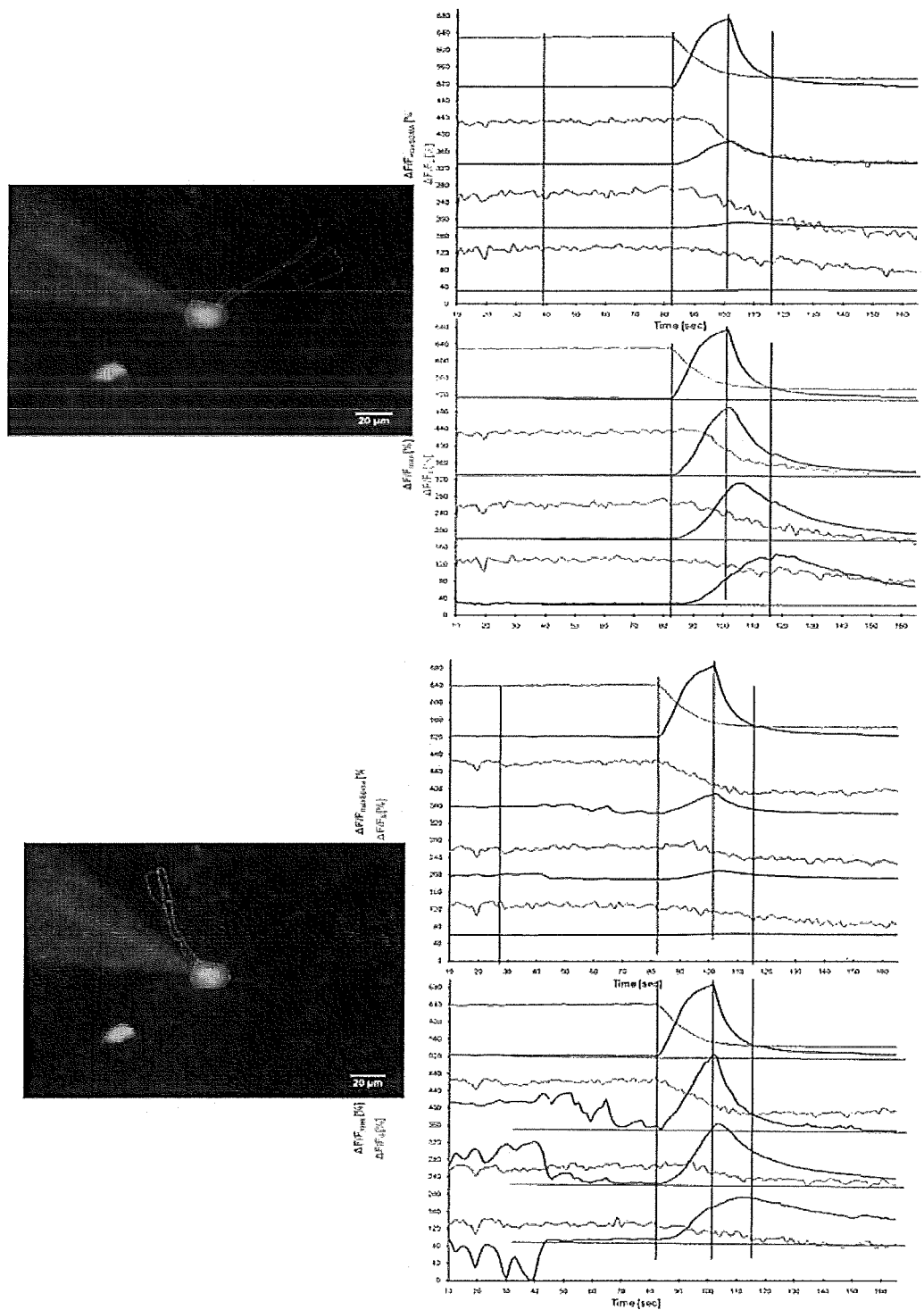
FIG. 28 is a series of graphs depicting lysate uptake from soma and proximal dendrites.
Figure 31:
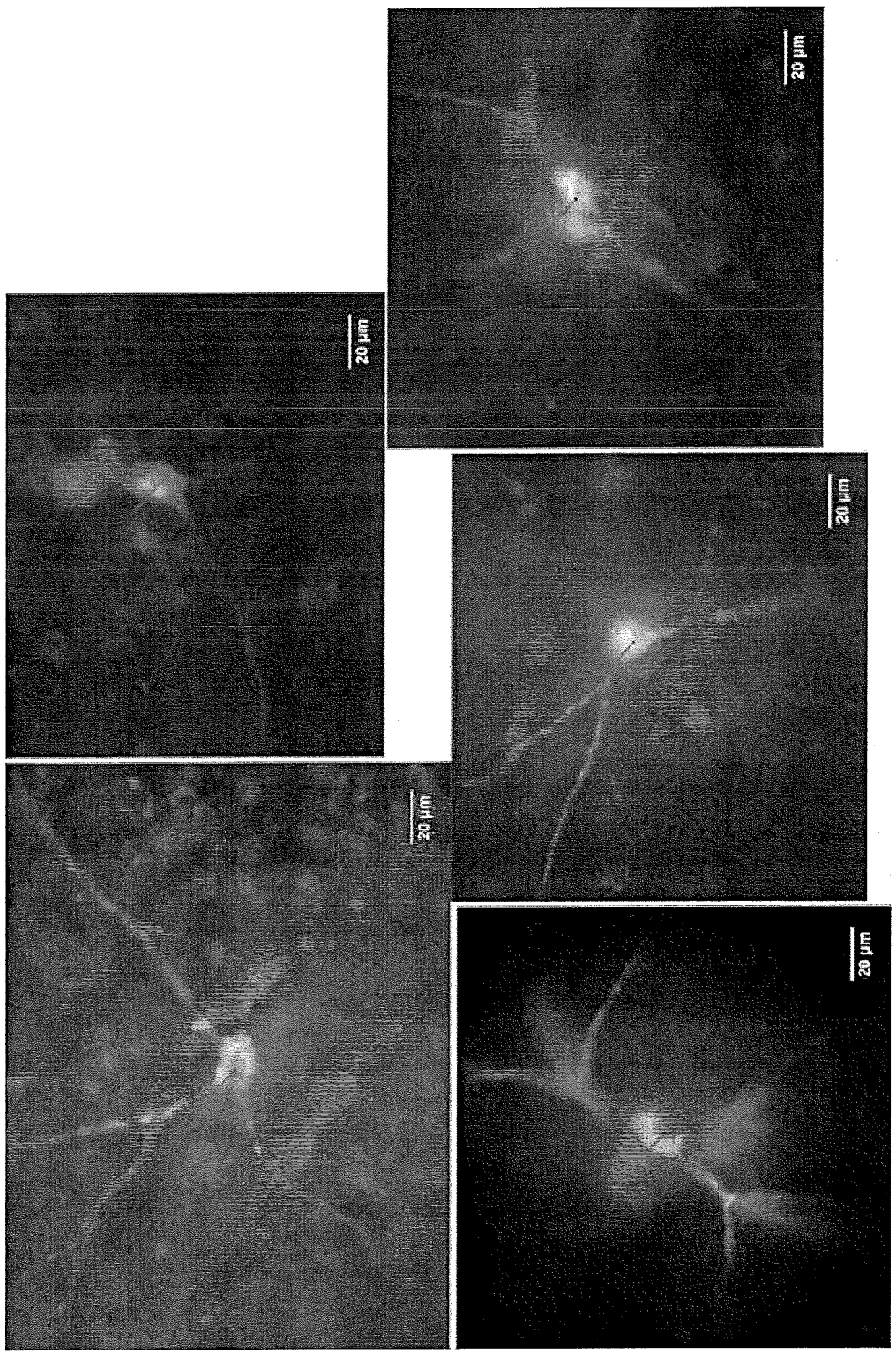
FIG. 31 is a series of photographs depicting evidence of a focal entry point in cells. These images were taken with very high exposure in order to visualize the residual dye molecules (lysis buffer) and the residual membrane fragments after Inside-Out Lysis.

A focally directed flow of a detergent-containing lysis buffer was applied to the cell body of the target cell in live tissue (FIGS. 7, 26, and 31). The diameter of the flow was smaller than the diameter of the cell body. The concentration of the detergent was above its critical micellar concentration (CMC) value. These two properties enabled the applied lysis buffer to enter the intracellular space without spilling to the adjacent cells in the tissue. Inside the cell, the detergent was diluted to a concentration value that was below its CMC value, allowing the lysis buffer to accumulate in the intact intracellular space and to diffuse throughout the complex shape of the target cell without affecting its complex tissue surroundings. Once enough lysis buffer accumulated inside the target cell and the detergent concentration re-approached its critical value, the cell membrane was lysed from inside ("Inside-Out Lysis") and the lysate was immediately up-taken by a nearby suction channel. The estimated volume of the obtained single-cell lysate is approximately 5-10 nL. The lysis buffer contains a cocktail of irreversible and reversible protease, phosphatase and RNAse inhibitors. Once the lysis buffer has entered the intracellular space, it mixes and homogenizes the intracellular components. Within 10-20 seconds and with perfect spatial resolution, the Inside-Out Lysis method converts a single live cell of any shape in complex solid tissue to a mixed lysate solution with all classes of molecules preserved (FIG. 7).

The materials and methods employed in these experiments are now described.

Materials and Methods

Imaging Setup

The sampling setup was built on the basis of an Olympus BX51WI fluorescence microscope, supplemented with a Hamamatsu Orca-R2 camera and two fast filter wheels (Sutter Instrument Company) for both the excitation channel and the emission channel. Both filter wheels were controlled by the Lambda 10-3 controller (Sutter Instrument Company). The light path in the excitation channel was controller by a SmartShutter™ (acquired from Sutter Instrument Company). The imaging process was controlled by the Micro-manager software.

The following water immersion objectives were used: Olympus 10× (UMPLFLN 10XW, NA 0.3, working distance 3.5 mm), 20× (UMPLFLN 20XW, NA 0.5, working distance 3.5 mm) and 40× (LUMPLFLN 40XW, NA 0.8, working distance 3.3 mm). These objectives were chosen because of the acceptable working distance given the high numerical apertures. The imaging setup was mounted on and firmly fixed to a TMC air-pressure table to avoid any vibrations.

Animals and Organotypic Cultures

All animal procedures were in accordance with Harvard Medical School (HMS) regulations and under an active animal protocol. GIN mice were purchased from Jackson labs. GAD67-GFP mice were obtained from the Murthy lab (Harvard University). GIN mice were used for most experiments. The standard protocol for hippocampal organotypic cultures was used (Stoppini et al., 1991 *J Neurosci Methods.* 37(2): 173-182). Mouse pups (postnatal day 5 or 6) were subject to hypothermia and were decapitated. The hippocampus was then dissected in the Gey's Balanced Salt Solution supplemented with 6.5 g/L glucose. 300 μm thick slices of hippocampus were obtained by using a manual tissue slicer. The obtained hippocampus slices were then quickly transferred to the Millipore inserts (acquired from Millipore; 0.4 μm height, 30 mm hydrophilic PTFE) and cultured in the incubator under the following conditions: 5% $CO_2$, 37° C. The culturing medium contained heat-inactivated horse serum and was prepared as follows: 50 ml MEM 2×, 120 mg Tris, 910 μL of a 7.5% $NaHCO_3$ solution, 50 ml heat-inactivated horse serum, 50 ml 1×HBSS and $ddH_2O$ (added up to 200 ml total volume). Hippocampus slices were serum deprived for 10 hours before lysing single cells. Hippocampus slices were successfully cultured for periods of time exceeding one month with excellent preservation of morphological and tissue-organizational characteristics.

A customized recording chamber for maintaining live tissue during the Inside-Out Lysis process, was casted from Sylgard® 184 (Dow Corning Corporation). The Millipore inserts with live organotypic slices could be inserted and removed from this chamber easily. The tissue slices were perfused in a heated HBSS solution. Perfusion was stopped during and immediately after the Inside-Out Lysis process.

Inside-Out Lysis Setup

Micropipettes were pulled from borosilicate glass tubes with filament (Sutter Instrument Company; OD:1.0 mm, ID: 0.78 mm) with the P-1000 Micropipette Puller (Sutter Instrument Company). Customization of micropipettes was achieved with the assistance of a microforge (Narishige MF-900).

Lysis buffer was prepared as described elsewhere herein. Before loading the delivery micropipette, the cocktails of inhibitors (Halt™ Protease Inhibitor Cocktail 3×, Halt™ Phosphatase Inhibitor Cocktail 3×) were added to the lysis buffer and the lysis buffer was kept on ice. AlexaD555 (MW 10,000) was purchased from Invitrogen. SR101 was purchased from Sigma.

Figure 29:
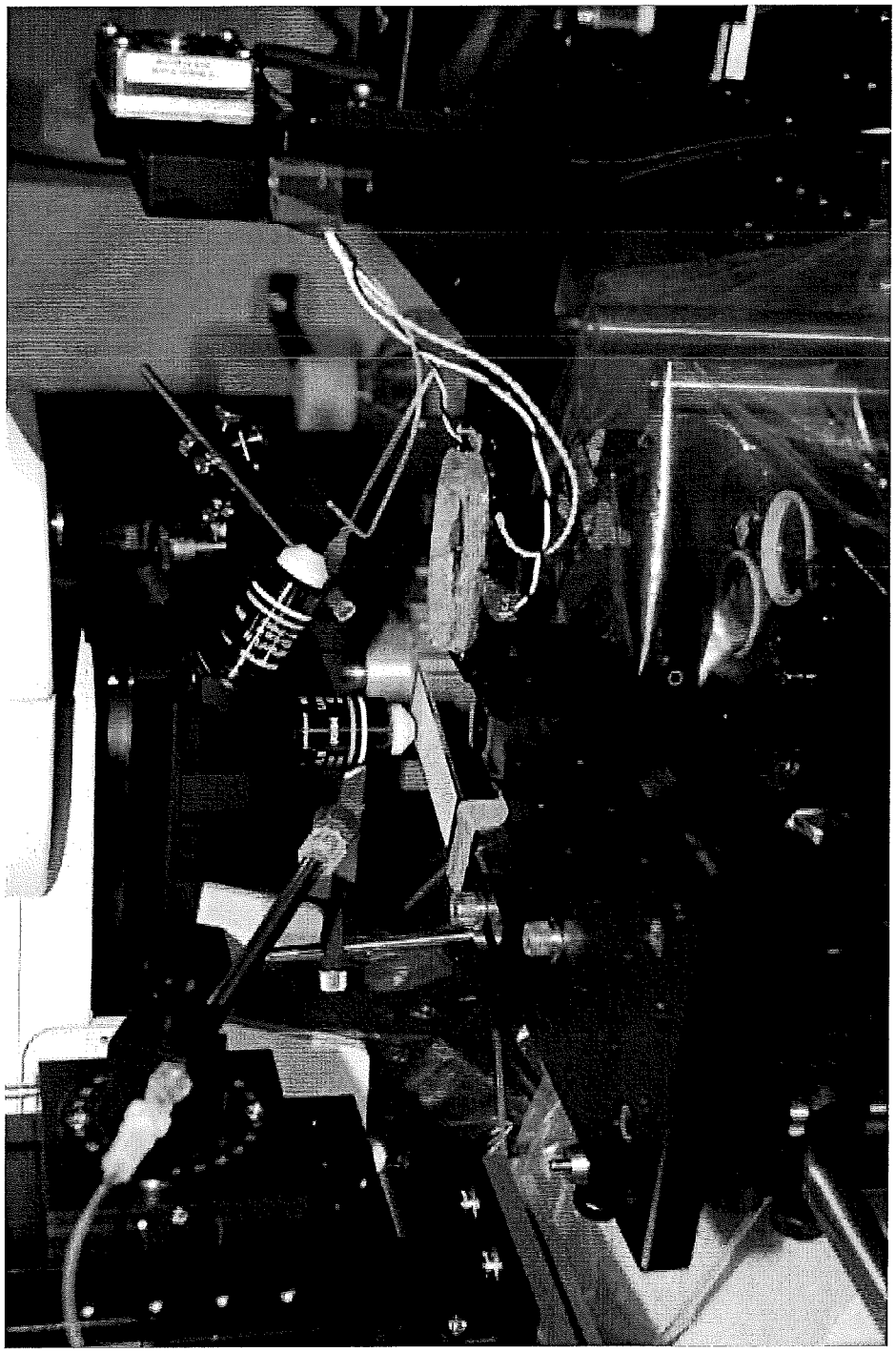
FIG. 29 is a photograph depicting the fast switching between the uptake of the lysis product (lysate) and the deposition of the lysate on the nitrocellulose pad in an automated experimental set-up.

A set of three MP-285 and one MP-225 micromanipulators were acquired from Sutter Instrument and were integrated on the basis of two interconnected MPC-200 controllers (Sutter Instrument Company). The master MPC-200 controller was then interfaced with the GUI in Microsoft Visual Studio via the USB port and via the appropriate C++ libraries for USB port control. All the manipulators were arranged and aligned in such a way that quick switching between the Inside-Out Lysis procedure and the printing procedure could be completed within a few seconds (FIG. 29). The pressure controller was acquired from MicroData Instrument and was interfaced with the GUI over the parallel port and the appropriate C++ library for parallel port control.

The recording chamber was positioned on one MP-285 manipulator. All glass slides with nitrocellulose pads were acquired from GraceBioLabs. The glass slide with a nitrocellulose pad was attached to another MP-285 manipulator. The delivery micropipette was mounted on the MP-225 manipulator and the suction/printing micropipette was mounted on the third MP-285 manipulator. A set of movements was preprogrammed to quickly switch from the recording chamber to the nitrocellulose slide after the completion of Inside-Out Lysis. A set of movements was preprogrammed to quickly retract the uptake micropipette out of the recording chamber and to position it a few microns above the nitrocellulose pad just before printing. Printing was conducted manually but can also be automated. All these movements were completed within a few seconds. While imaging the Inside-Out Lysis process on one cell, the 40× objective was used. When imaging the automated version of Inside-Out Lysis on several cells, the 20× objective was used. The 10× objective was used for printing single-cell lysates on nitrocellulose and for imaging the overviews of whole tissue slices. The sub-micron resolution and programmability of the used micromanipulators allowed for single cell lysis and printing the single-cell lysates in a reproducible fashion as described elsewhere herein.

Printing Concurrent Titration Series

Nitrocellulose slides were acquired from GraceBioLabs. 2470 Aushon Arrayer was acquired from Aushon Biosystems in order to print the titration series on the nitrocellulose slides next to single-cell lysates. GFP protein was acquired from Millipore (14-392). PKCδ and PKCα were acquired from Invitrogen (P2287, P2227). All purified proteins were diluted in the same SDS-containing buffer that was used for single-cell lysis and were printed in 1:2 dilution series on the nitrocellulose pads before printing single-cell lysates on the same nitrocellulose pads. Eight depositions per spot were used in the settings of the high-precision Aushon Arrayer in order to reach a homogenous distribution of proteins within each printed 200 μm spot of the titration series.

Antibodies

Figure 30:
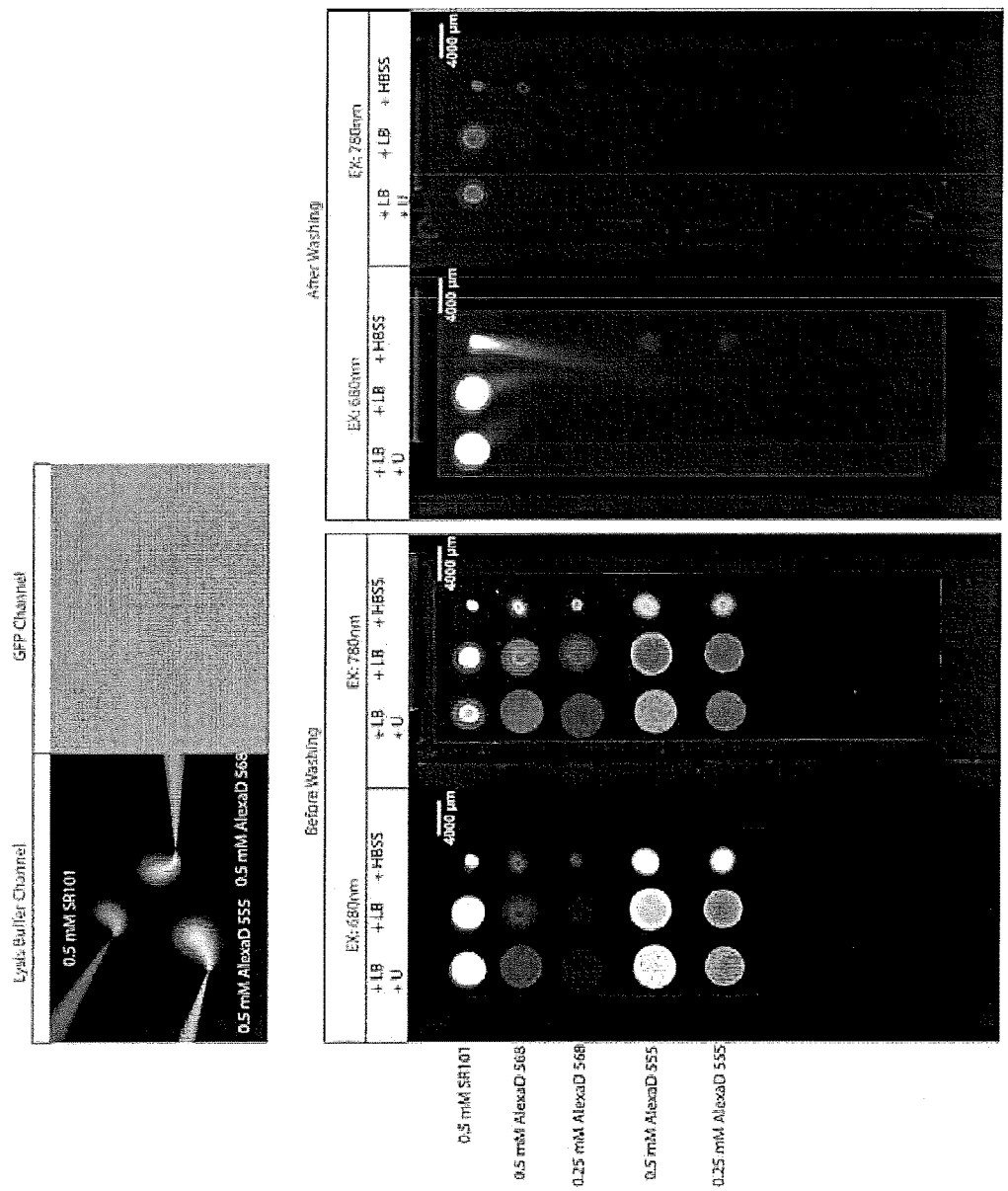
FIG. 30 is a series of photographs depicting the separation of lysis visualization and analytical procedures. If optical methods are used for signal detection then the visualization of Inside-Out Lysis (sampling), necessary to ensure single-cell resolution and to record the cell morphology (if the target cell is not fluorescent), should not interfere with optical signal detection. Different fluorescent dyes (SR101, Alexa 568 dextrane (MW 10,000), Alexa 555 (MW 10,000)) were tried in order to identify the dye that could be washed out after printing the lysate on nitrocellulose. All dyes provided sufficient visualization capabilities for Inside Out Lysis. Different dyes were mixed with the lysis buffer (Tris·HCl (50 mM), SDS (2%), Glycerol (5%), NaF (1 mM)). Also added were 7.4 M urea to the dye-containing lysis buffer. In another instance Hank's Balanced Salt Solution (HBSS) was mixed with each dye. Overall, this example demonstrates that in contrast to the above Alexa dyes, SR101 is not suitable for optical post-lysis signal detection because it is hard to wash out from nitrocellulose. If signal detection is achieved by non-optical methods (such as LA-ICP-MS), then the ability to wash out the fluorescent dyes used for sampling visualization should not matter.

The protocol for washing nitrocellulose slides with printed lysates and for subsequent antibody incubation as described by Sevecka et al. was used (Sevecka and MacBeath, 2006, Nat. Methods 9:152-158; Sevecka et al., 2011, Mol. Cell Proteomics 10:M110.005363). The protocol for washing the printed nitrocellulose slides (FIG. 30) and for subsequent antibody incubation was used as described by Sevecka et al. (Sevecka et al., 2011, *Mol Cell Proteomics.* 10(4): M110.005363; Sevecka and MacBeath, 2006, *Nat Methods.* 3(10): 825-831). The nitrocellulose slides were shortly washed in PBST first and were then washed in Tris buffer (pH 9) for 48 hours. The slides were then blocked in 5% BSA/PBST of the blocking solution provided by LiCor (Odyssey Blocking Buffer) at 4° C. for 1 hour. Next, the slides were incubated with the primary antibodies. The primary β-actin antibody (A1978, Sigma) and the primary GFP antibody (2956, Cell Signalling Technology) were incubated at 1:1000 in 5% BSA/PBST or in Odyssey Blocking Buffer (LiCor) for 24 hours at 4° C. Subsequently, the secondary antibodies (anti-rabbit 680 and anti-mouse 800) were applied at 1:1000 for 12-24 hours at 4° C. The nitrocellulose slides were then quickly washed in PBST several times and were scanned on a LiCor Odyssey scanner (LiCor).

The results of the experiments are now described.

Detergent-Based Lysis

The sampling method of the present invention is applicable to live solid tissues. Therefore, the sampling method of the invention circumvents the disaggregation process and eliminates the artifacts and the biases of various fixation protocols. This sampling method also preserves transcripts, proteins and metabolites by incorporating the technical advantages of detergent-based lysis (Table 1).

TABLE 1

Comparison Between Fixation and Detergent-Based Lysis

| Fixation/Staining/Permeabilization | Detergent-Based Lysis of Live Cells |
|---|---|
| Mechanism parameters are unknown. | Biophysical parameters of detergent/protein and detergent/membrane interactions are known. |
| Molecular preservation varies across cell types across molecule classes across molecules within each class. | All proteins, transcripts, metabolites are preserved by protein denaturation and by protease/RNAse/phospho inhibitors. |
| Incompatible with analytical methods, unless reduced to the lysate format. | Compatible with MS, Western Blot, Lysate Microarrays, RT-qPCR and Sequencing methods across all proteins, transcripts and metabolites. |

Figure 3:
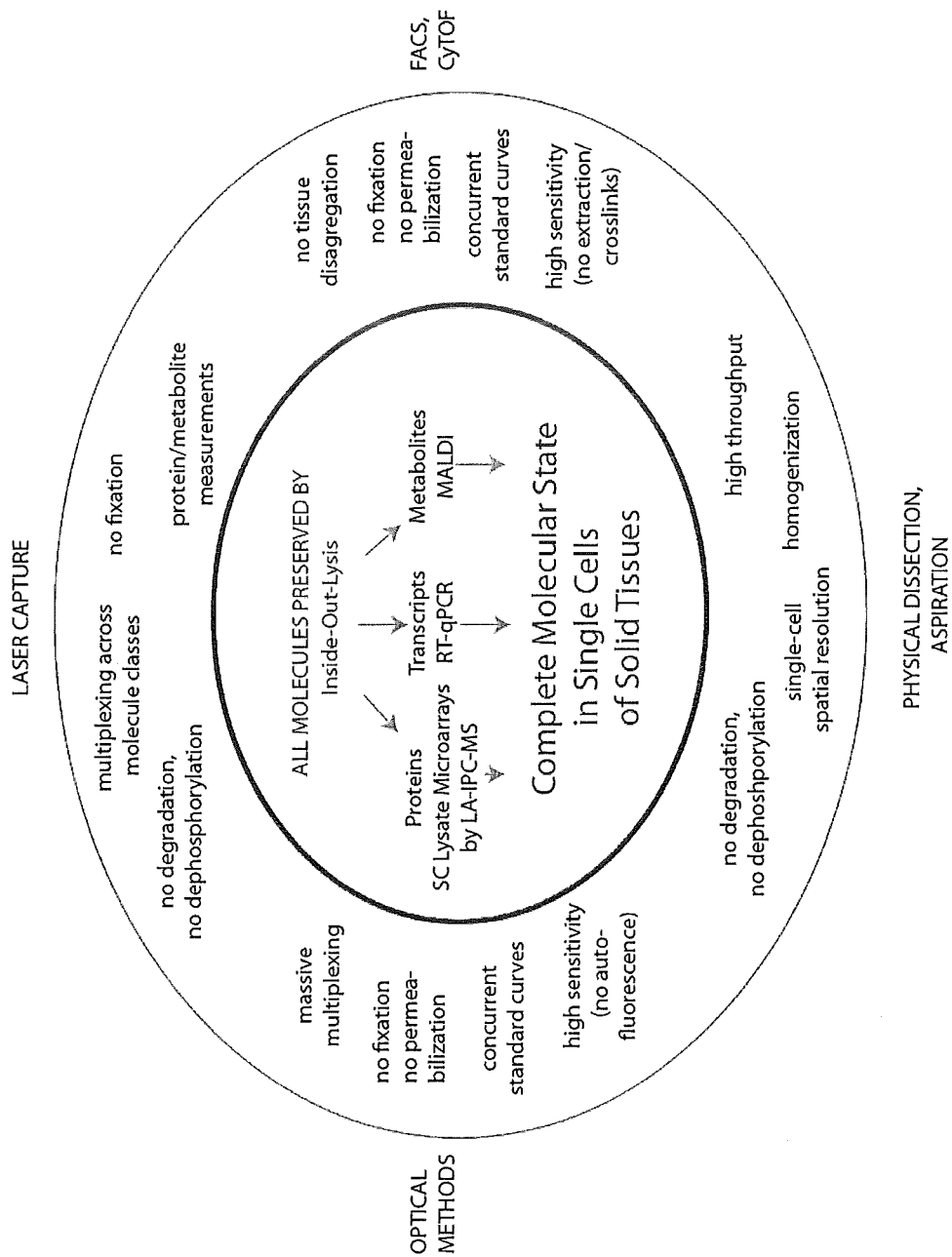
FIG. 3 is a schematic illustration depicting the strategy for resolving limitations. The platform consists of a new sampling method (Inside-Out Lysis), a new analytical method for measuring native proteins in single cells of solid tissues (Single-Cell Lysate Microarrays) and a set of compatible analytical strategies for the quantification of native transcripts and metabolites in single cells of solid tissues. This platform resolved limitations of current methods for sampling and analyzing single cells in solid tissues.

The mixed lysate format and the preservation of all the molecules of the target cell enables the measurement of the 'complete molecular state' in each sampled single cell by applying RT-qPCR (or RNA-Seq), LA-ICP-MS and MALDI-MS to the sub-partitions of the homogenous diluted lysate (FIG. 3).

The need for maintainable live tissue samples has been more acute in neuroscience than in any other field of the life sciences. Because of the loss of tissue context, it has been difficult to study the relationship between neuronal morphology and neuronal function in dissociated neuronal cultures. Dissociated neuronal cultures also make it challenging to study the time course of molecular and morphological development of many neuronal cell types. Because of this acute need for maintainable live tissue systems, organotypic cultures were developed and widely adopted in neuroscience before the need for such live tissue systems emerged in other areas of basic biological research.

Figure 4A:
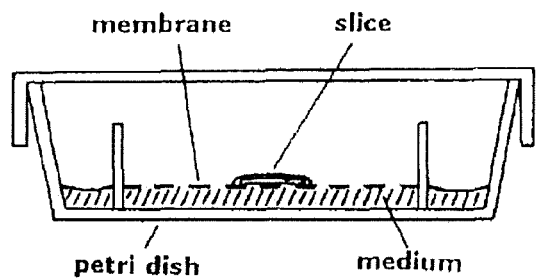
FIG. 4A and FIG. 4B depict organotypic cultures.
Figure 4B:
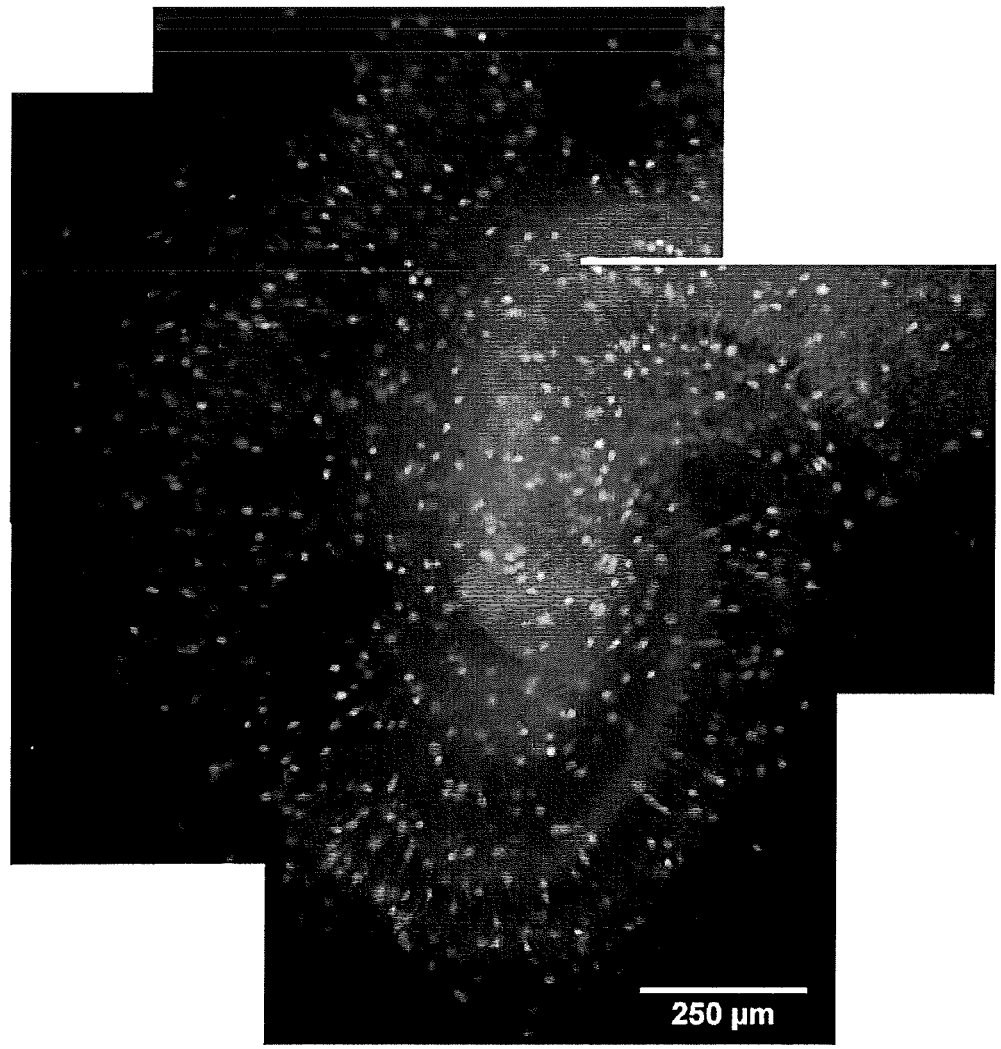

Organotypic cultures of rodent brain regions are maintainable for months in an incubator. After quickly dissecting and slicing the mouse brain region of interest in an optimized procedure, one can culture the harvested slices on a porous membrane in a specialized dish (Stoppini et al., 1991, J. Neurosci. Methods 37:173-182). An example of such a setup is displayed in FIG. 4A. In this setup, the medium does not surround the tissue slice but is up-taken from underneath the porous membrane by the capillary action of the tissue slice. The medium can be either serum-based or serum-free. Hippocampus, cortex, thalamus and cerebellum can be cultured successfully in this manner (Gähwiler et al., 1997, Trends Neurosci. 20:471-477; Banker and Goslin, 1998, Culturing Nerve Cells, second edition).

The time course of development and the associated molecular/morphological changes in organotypic cultures of rodent brain regions resemble the time course of development and the associated molecular/morphological changes in vivo (in live rodents). For example, the onset of long term potentiation (LTP) in vivo occurs at the end of the second postnatal week in rats (Muller et al., 1993, Brain Res. Dev. Brain Res. 71:93-100). In a study by Muller et al., the organotypic hippocampal cultures prepared from 8-days-old rats showed a much faster onset of LTP than the organotypic hippocampal cultures prepared from 2-days-old rats. In both cases however, the onset of LTP occurred at the time equivalent to the time point of 12-14 postnatal days in vivo (Muller et al., 1993, Brain Res. Dev. Brain Res. 71:93-100). This observation suggests that the natural course of molecular development is preserved in organotypic cultures. This observation is consistent with the theory that the course of molecular development in organotypic cultures is not a result of the preparation procedure. The time course of synaptogenesis in organotypic hippocampal cultures also resembles the time course of synaptogenesis in vivo, as assessed by comparative electrophysiological and morphological measurements in organotypic cultures and in the acute brain slices of rats of different ages (Gähwiler et al., 1997, Trends Neurosci. 20:471-477; Muller et al., 1993, Brain Res. Dev. Brain Res. 71:93-100). In the same study by Muller et al., the spatial distribution of synaptogenesis rates across different regions of hippocampus in organotypic cultures resembled the spatial distribution of synaptogenesis rates in vivo (Muller et al., 1993, Brain Res. Dev. Brain Res. 71:93-100).

The organotypic cultures of human colon, lung and prostate tumors were recently established and optimized (Vaira et al., 2010, Proc. Natl. Acad. Sci. USA 107:8352-8356). The culturing procedure of human tumors is similar to the above-described procedure used for culturing rodent brain tissue. Vaira showed that the spatial organization and morphology of cultured human tumors was preserved in organotypic cultures for 5 days after explantation and resembled the original tissue organization. During this culturing period of 5 days, the counts of proliferating and apoptotic cells did not change either. Vaira also showed that pharmacological and analytical studies can be performed in the organotypic cultures of human tumors. The success of culturing various human tumors demonstrates that the methodology of organotypic cultures is general and can be applied to different organs in humans and animals.

Detergents have widely been used for cell lysis in analytical biochemical studies. All rigorous analytical methods require the lysate format of the sample. Table 1 summarizes the advantages of detergent-based cell lysis as compared to cell fixation. There exist a large number of biophysical studies describing the parameters of detergent/protein interactions and the parameters of detergent/membrane interactions (Helenius and Simons, 1975, Biochim. Biophys. Acta 415:29-79; Lichtenberg et al., 1983, Biochim. Biophys. Acta 737:285-304).

Detergents belong to the molecular class of amphiphilic lipids. Each detergent monomer contains a polar region (head) and a non-polar region (tail). The latter usually consists of alkyl chains and/or aromatic groups. The size of the tail of a detergent monomer determines its interaction area with water. The interaction area of the tail with water determines the overall hydrophobicity of the amphiphilic detergent due to the decrease of entropy in water. Generally, amphiphilic lipids with high hydrophobicity (phospholipids and cholesterol) are not soluble in water, whereas amphiphilic lipids with lower hydrophobicity (detergents) are soluble and have a critical micellar concentration (CMC). When the total concentration of a given detergent reaches its CMC value, the addition of any excess detergent molecules to the solution is compensated by the process of micelle formation such that the concentration of free detergent monomers does not exceed the CMC value. The CMC value of a detergent is decreased by higher hydrophobicity, increased by the bulkiness of the tail region, and is also increased by the charge of the head region. Therefore, different detergents have different CMC values. The CMC value of a given detergent and the number of detergent molecules in micelles (aggregation number) also depend on the temperature, the ionic strength and the pH value of the solution.

Figure 6:
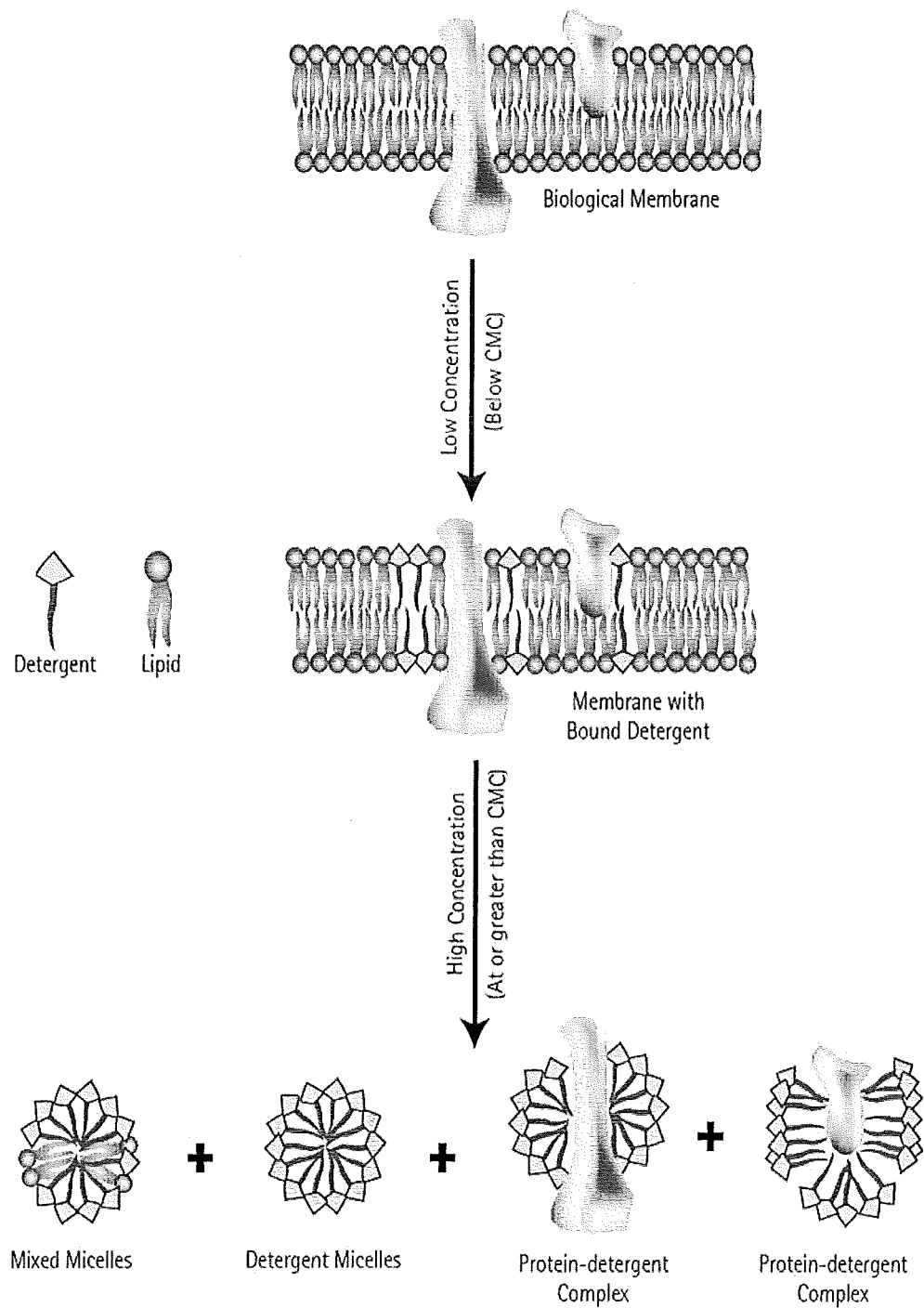
FIG. 6 is an illustration depicting a simplified model of detergent-based lysis. A concentration greater than the CMC value might be required to induce membrane solubilization. Also, the extent of membrane solubilization depends on the composition of the membrane and the number of detergent monomers integrated into the membrane.

The interactions of detergents with biological membranes have been studied extensively with the help of the liposome model (FIG. 6). When the total concentration of detergent molecules is increased above the CMC value in a solution with liposomes, the concentration of free detergent monomers stays at the level below the CMC value because the excess detergent molecules integrate into the phospholipid bilayer of liposomes. As the total concentration of detergent molecules is further increased, the number of detergent molecules in the phospholipid bilayer of liposomes reaches the saturation level, thereby causing the formation of mixed micelles. These mixed micelles contain liposomal phospholipids and detergent molecules. By even further increasing the total concentration of detergent molecules in the solution, all liposomes are solubilized into mixed micelles. Thus, at each concentration of detergent in the solution there is an equilibrium between the free monomers and the monomers integrated into the phospholipid bilayer and there is an equilibrium between the detergent monomers integrated into the phospholipid bilayer and the formation of mixed micelles. The micelle formation process is fast (rate constant of $10 \text{ s}^{-1}$). Empirically, it was also shown that the presence of detergents, such as sodium dodecylsulphate (SDS), increases the membrane area of erythrocytes and protects erythrocytes against osmotic shock.

Micelle formation is crucial for the solubilization of biological membranes but is not crucial for the binding of detergents to soluble proteins. Detergents bind to soluble proteins as monomers at concentrations below the CMC value. Ionic detergents such as SDS generally have a denaturing character. They first bind the hydrophobic patches on the protein surface and thereby start unfolding the protein. The unfolding process then exposes more hydrophobic patches. Thus, the overall process of detergent-induced denaturation is cooperative. The detergent molecules bound to soluble proteins are not available for micelle formation and the detergent molecules bound to micelles are not available for protein binding. Thus, the process of micelle formation and the process of protein binding are competitive.

Figure 5:
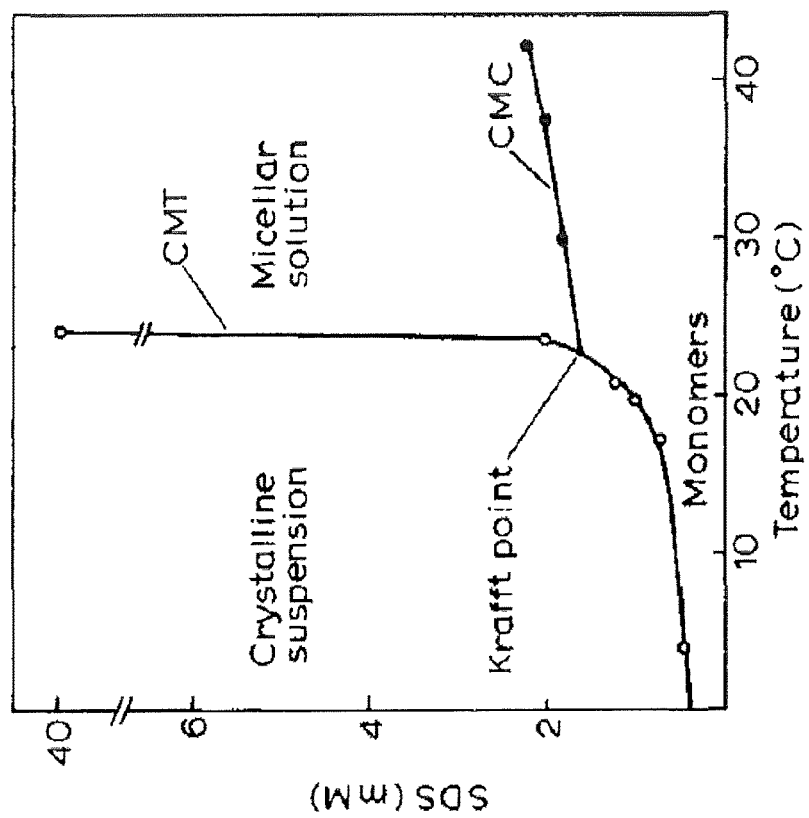
FIG. 5 is an illustration depicting the phase diagram of SDS. The SDS solution was kept at pH 7.4 and contained 0.1 M NaCl and 0.05 M sodium phosphate. The critical micellar temperature was designated as CMT. The critical micellar concentration of SDS was designated as CMC (from Helenius and Simons, 1975, Biochim Biophys. Acta 415:29-79).

The most widely studied detergent is SDS. SDS is an anionic detergent that denatures soluble proteins into straight polypeptide regions and has a constant binding ratio in most proteins. Importantly, SDS does not denature some crucial proteases even at concentrations above the CMC value. When SDS is used for cell lysis, it is common to add a cocktail of reversible and irreversible protease and kinase/phosphatase inhibitors. CMC values of SDS widely vary depending on the composition of the solution. In pure water, the CMC value of SDS is 8.2 mM. In 0.5M NaCl solution, its CMC value is 0.52 mM. FIG. 5 displays the concentration-temperature phase diagram of SDS. This phase diagram also shows that SDS is not present in the crystalline form at biological temperatures (above critical micellar temperature).

Mechanism of Inside-Out Lysis

The following lysis buffer formulation was used: Tris·HCl 50 mM, SDS 2%, Glycerol 5%, NaF 1 mM, 0.5 mM AlexaD555 (10,000), Halt™ Protease Inhibitor Cocktail 3×, Halt™ Phosphatase Inhibitor Cocktail 3×. In several initial experiments, sulforhodamine 101 (SR 101) was used instead of Alexa 555 dextrans. Two mouse strains expressing cytosol-soluble GFP in different subsets of hippocampal interneurons were used in the experiments. These mouse strains were: GAD67-GFP (broad set of putative interneurons), GIN (somatostatin interneurons). Experiments were performed in organotypic hippocampus slices of either GAD67-GFP or GIN mice.

The Inside-Out Lysis process was imaged by acquiring the frames of GFP and Alexa 555 fluorescent intensities with the aid of a rapid filter wheel attached to the microscope. The delivery process of lysis buffer was optimized by performing different configurations of pulled glass micropipettes. The tip aperture of the delivery pipette that was used in the experiments was 0.7 µm. The lysis buffer was added to the target cell at an angle or from above (vertical application). The latter configuration was achieved by carefully crafting the delivery micropipette and bending its taper such that the focal stream of lysis buffer was perpendicular to the surface of the tissue slice. In some instances, attempts were made to prevent the tip of the delivery micropipette from touching the surface of the target cell at the time of delivery initiation.

In the experiments where the final uptake of the single-cell lysate was performed, a customary bent glass micropipette having a 10 µm aperture was used. The flow vector generated by this suction micropipette was perpendicular to the surface of the tissue slice. The aperture of the suction micropipette was positioned 20 µm above the surface of the tissue slice and directly above the target cell. No active negative pressure was applied, as suction was generated solely by the capillary action of the glass capillary. Pulled glass micropipettes were used because of their low cost and easy customization.

Figure 8:
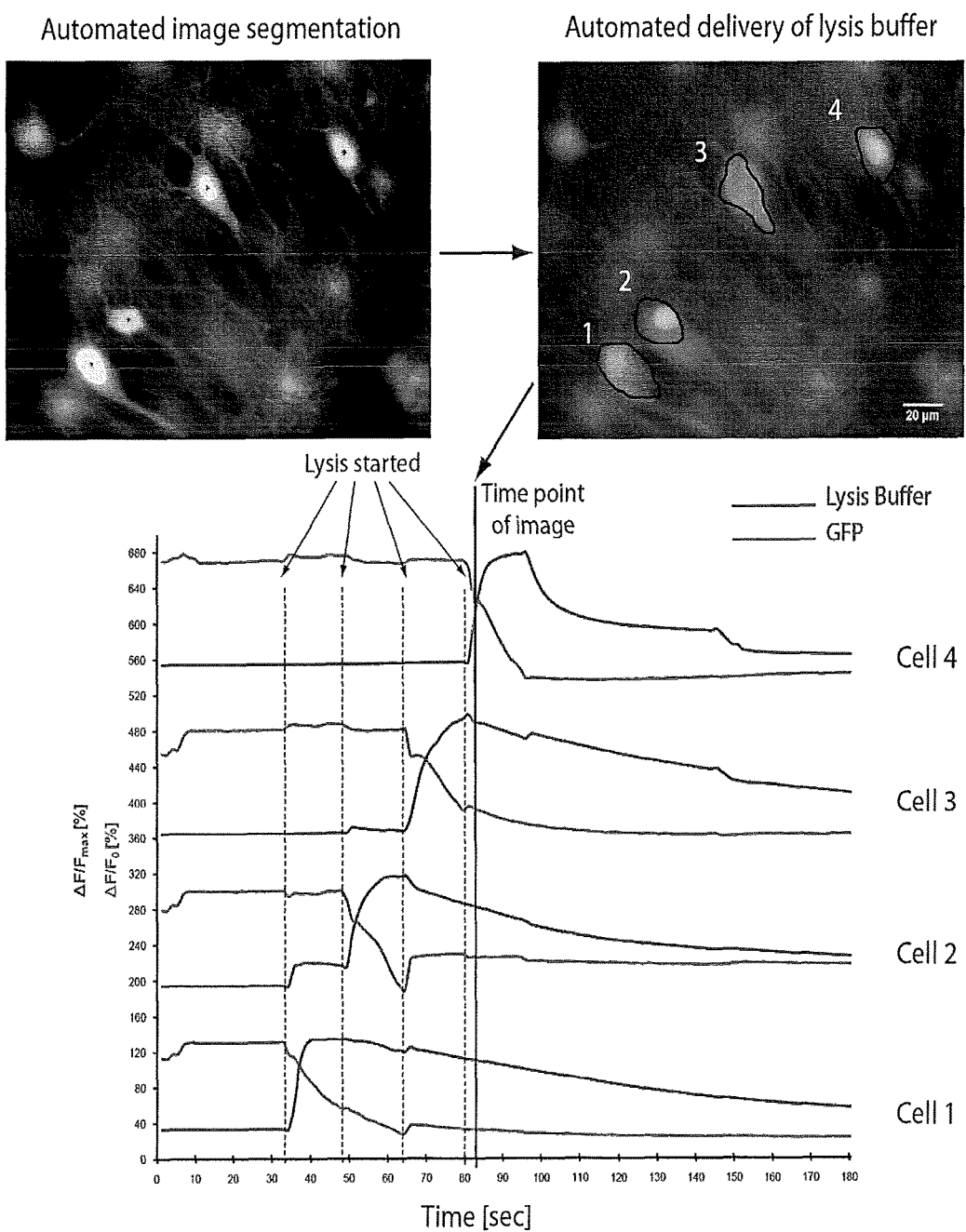
FIG. 8 is an illustration depicting the rapid denaturation of soluble proteins. This is the same experiment as in FIG. 7. GFP fluorescence decreased as soon as the SDS-containing lysis buffer entered the intracellular space of each target cell. During this decrease of GFP fluorescence, SR101 dyes stayed strictly within the geometric boundaries of the target cells (with exception of cell 2) implying that the membrane barrier was intact from the time point of lysis buffer delivery to the time point of GFP fluorescence loss. No suction was applied. Thus, the decrease of GFP fluorescence represents the intracellular GFP denaturation. Here, the delivery of lysis buffer was fully robotic with no human input. The amount of lysis buffer applied in each instance was the same. The line of the second cell (SR101 mixed with the lysis buffer) shows a bump when the delivery to the first cell is initiated because of the fluorescence of the delivery pipette under the objective. Lysis buffer flow was perpendicular to the tissue surface.
Figure 9:
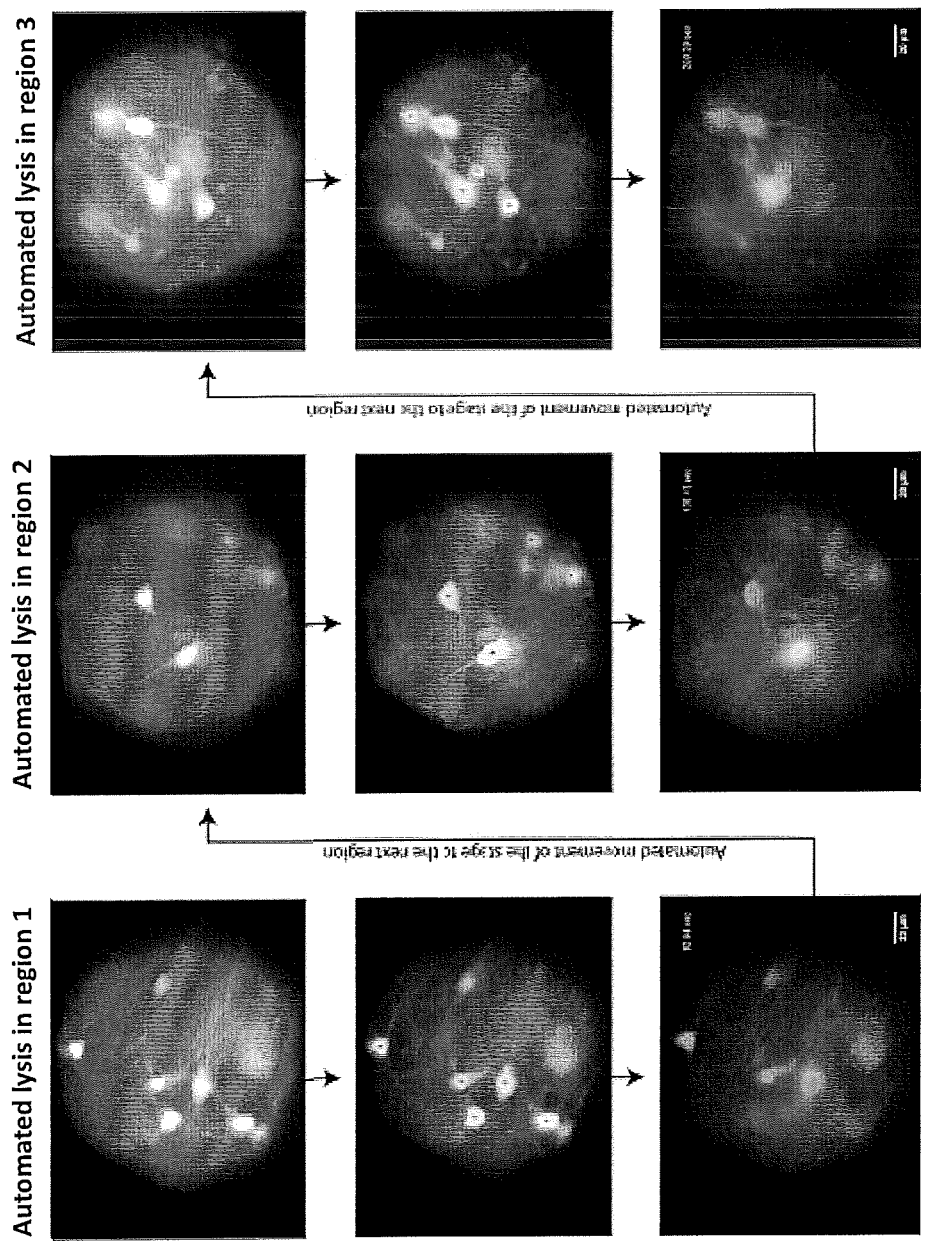
FIG. 9 is a series of photographs depicting a fully automated sequential lysis buffer delivery within a set of different regions of a cultured hippocampal slice (GAD67-GFP, P4+5DIV). Lysis buffer was delivered to fifteen cells in 3 different hippocampus regions in a fully automated manner within a 200 second time period (automated lysis buffer delivery was triggered 40 seconds after the imaging start). The imaged area was constrained by a diaphragm in order to ensure the planarity of the slice surface within that area. For each region three images are displayed: 1) an image acquired before the lysis process was triggered, 2) the same image after image segmentation, 3) an image acquired at a time point of the lysis buffer delivery process in that particular region.

Rapid denaturation of GFP was observed as soon as the SDS-containing lysis buffer entered the intracellular space of a GFP-expressing target cell. In both mouse strains (GAD67-GFP and GIN), GFP freely diffused throughout the cytosol. And because of its relatively small size, GFP also entered the nucleus. GFP fluorescence decreased to background levels immediately after the SDS-containing lysis buffer entered the intracellular space (FIGS. 8, 10, 19, 27, and 28). In these instances, GFP fluorescence continued to decrease while the Alexa 555 dextran (or SR101) molecules were located strictly within the geometric boundary of the single cell. Thus, GFP denaturation seemed to occur intracellularly while the membrane barrier was still intact. GFP fluorescence vanished before the cell membrane was solubilized. FIG. 8 shows the delivery of the SDS-containing lysis buffer to single cells without simultaneous suction (FIG. 9 depicts lysing cells in a fully automated sequential microlysis procedure). In all instances depicted in FIG. 8, GFP fluorescence started decreasing at the same moment when the lysis buffer entered the target cell and before the lysis buffer completely filled out the intracellular space by diffusion/convection. These observations were consistent with biophysical studies showing that detergent monomers bind and denature soluble proteins even at concentrations below the CMC value, which are discussed elsewhere herein.

Figure 10:
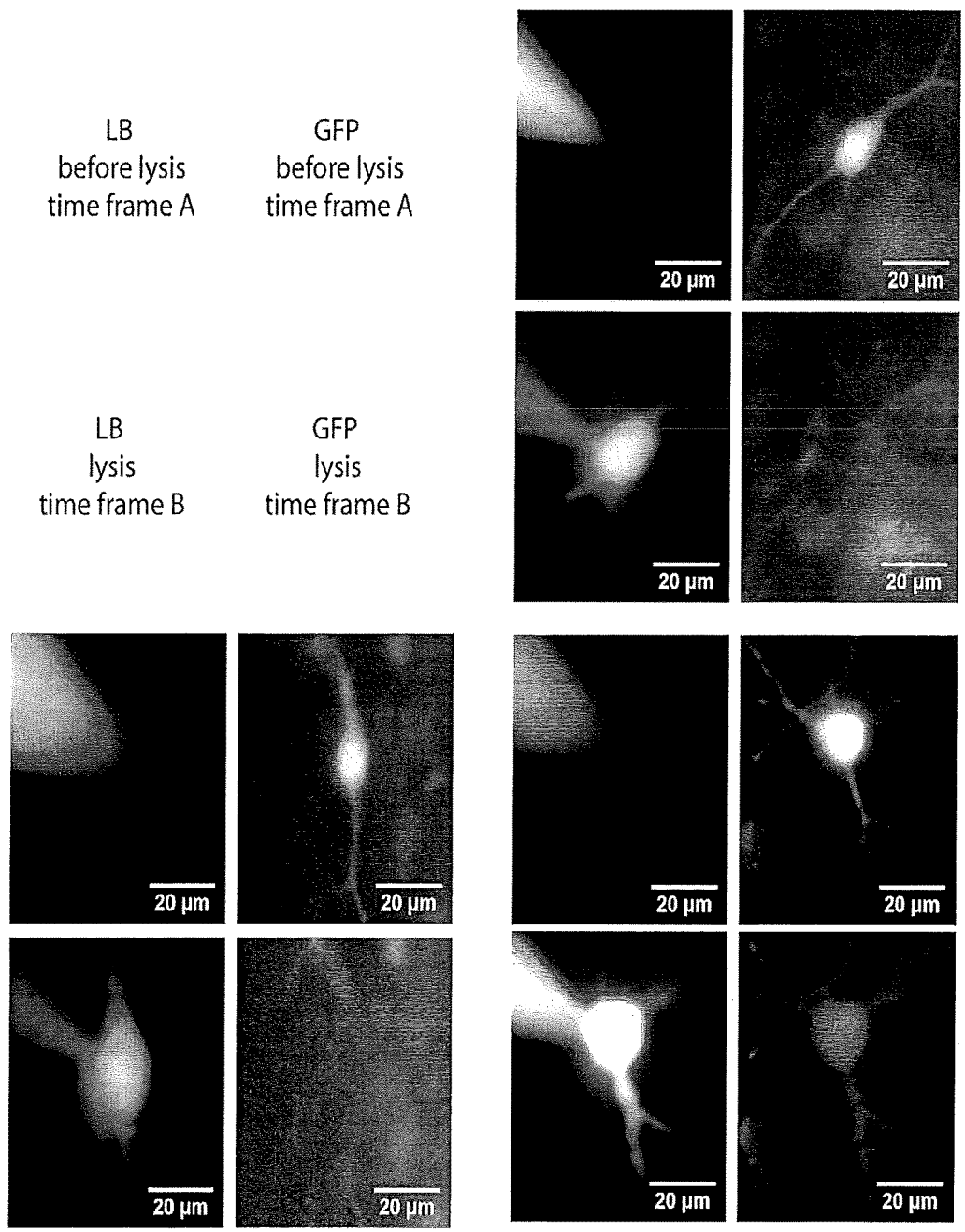
FIG. 10 is a series of photographs depicting cell membrane growth during the lysis buffer delivery. LB stands for lysis buffer. SDS was delivered to single cells by a focal stream of lysis buffer. GFP was denatured and the membrane of each target cell grew simultaneously. Alexa 555 dyes stayed within the geometric boundaries of the target cells during GFP denaturation and during membrane growth. Although not wishing to be bound by any particular theory, this suggests that the membrane barrier was intact from the time point of lysis buffer delivery, throughout the phase of GFP denaturation, and to the time point of extensive membrane growth. Also see FIG. 32.

In all instances of Inside-Out Lysis, a visible increase of membrane area was observed as the lysis buffer was accumulating within the geometric boundaries of the target cell (FIG. 10). This observation was consistent with the integration of SDS monomers into the phospholipid bilayer of the target cell before saturating it and before causing the formation of mixed micelles. This increase of membrane area simultaneously accompanied the decrease of GFP fluorescence inside the growing cell. This was consistent with the concept that protein binding by detergent monomers and membrane solubilization are competitive processes.

Figure 12:
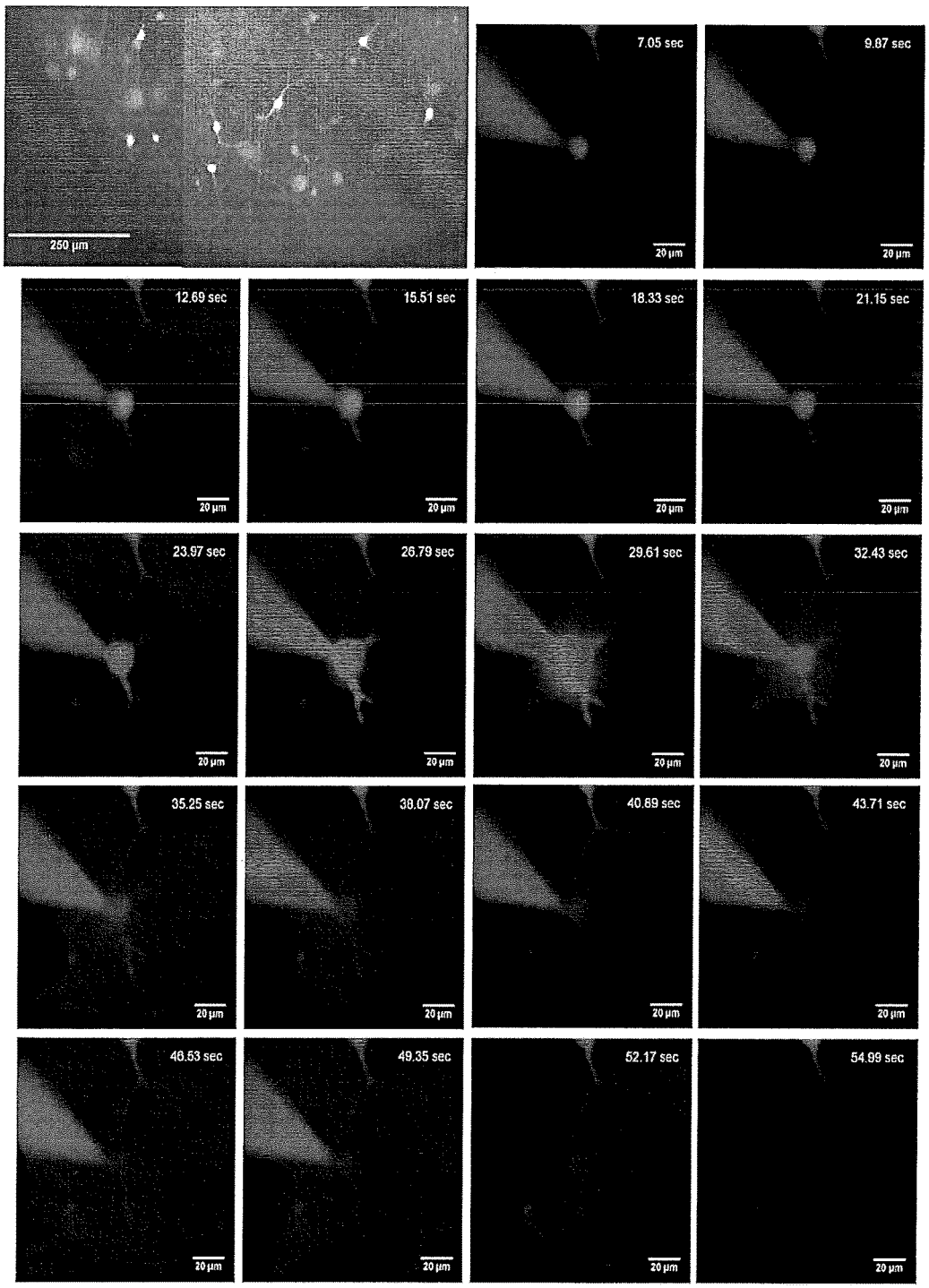
FIG. 12 is a series of photographs depicting the complete and rapid solubilization of the single-cell membrane by Inside-Out Lysis in live solid tissue. The arrow shows the GFP-expressing target cell (somatostatin interneuron) in a hippocampal organotypic slice of a GIN mouse. First, a small amount of lysis buffer (Alexa 555D was used here for visualization) was applied and the cell membrane was intact, presumably after the focal entry point of the applied lysis buffer was sealed. More lysis buffer was applied continuously until the membrane was completely solubilized from inside. The lysate was up-taken by a perpendicular simultaneous capillary-action-driven suction. The delivery micropipette was not bent and the delivery of lysis buffer occurred under an angle and not vertically.

Importantly, Alexa 555 dextran molecules (10,000 MW) of SR101 molecules did not exit the geometric confinements of the target cell when the lysis buffer was continuously applied to its intracellular space. Although not wishing to be bound by any particular theory, this suggests that the membrane barrier was intact during the phase of membrane growth. The solubilization of the cell membrane could be observed after its initial significant growth, as Alexa 555 dyes were observed to leave the geometric confinements of the target cell (FIG. 12). These observations were consistent with studies describing the solubilization process of biological membranes by detergents, which are discussed elsewhere herein.

In some instances, the stream of lysis buffer/solubilizing solution is preferably narrow initially and the aperture of the application channel is around 1.5 µm or smaller. Without wishing to be bound by any particular theory, it is believed that if the aperture of the application channel is larger, then the detergent flow is harder to direct towards the center of the cell and to create a focused intracellular source. Detergents are then more likely to reach the outer membrane and to compromise it too early, before solubilizing the nucleus.

Another important feature related to detergents is that the outer cell membrane increases in size (grows) as detergent monomers incorporate into it from inside. As the membrane grows, it is still intact and still preserves the intact barrier between the inside of the cell and the tissue surroundings. This feature effectively increases the available volume inside the cell and allows accumulation of the applied liquid inside the cell.

Different Modes of Membrane Solubilization

Figure 11:
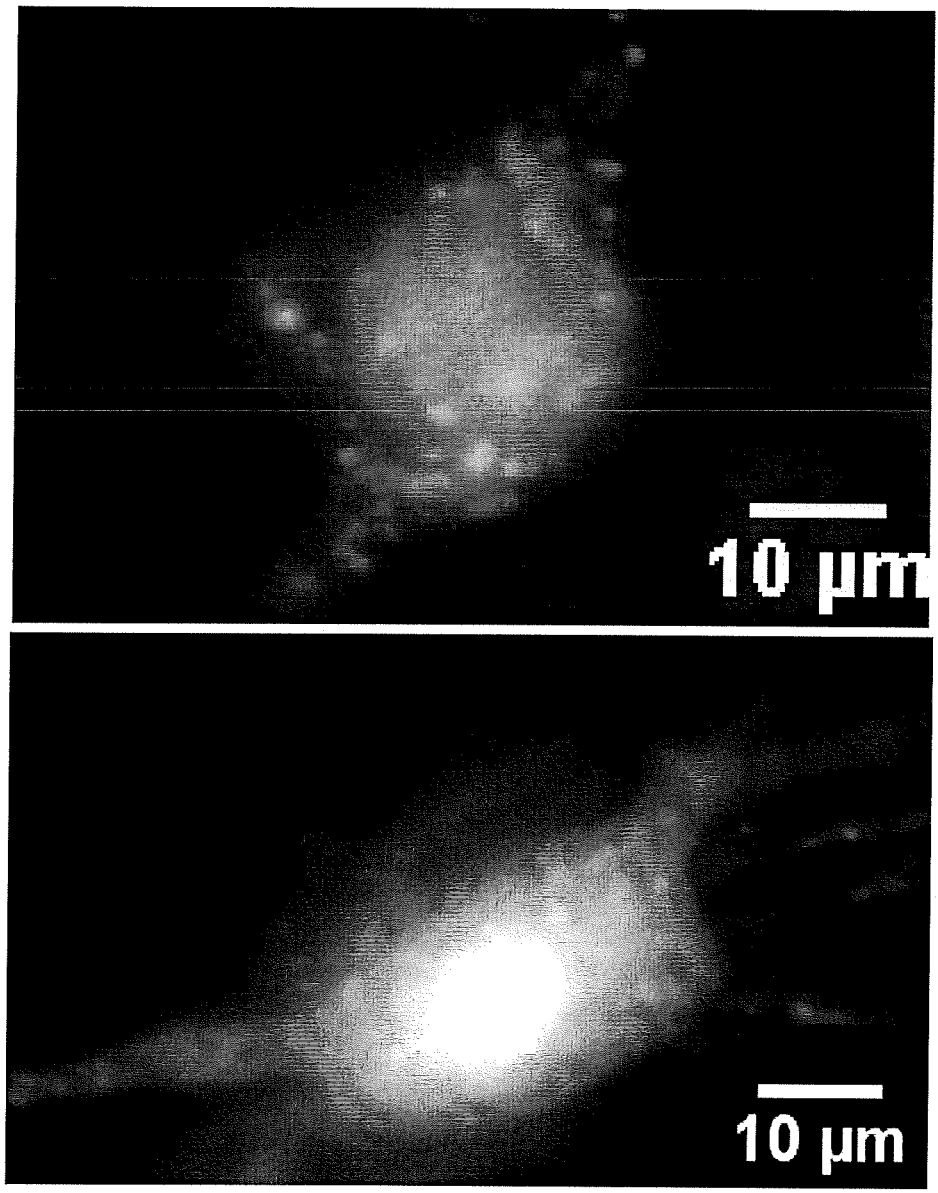
FIG. 11 is a photograph depicting the partial and slow solubilization of the membrane of a target cell. A smaller amount of SDS-containing lysis buffer was applied without the subsequent lysate uptake (no suction). SR101 dyes were observed to be slowly diffusing out of the geometric boundaries of the single cells following a 30 minute (upper image) or 11 minute (bottom image) waiting period. The leftover fluorescent regions were putative membrane patches after partial membrane solubilization. The upper image was acquired under the 20× objective in a GAD67-GFP slice (P4+4DIV). The bottom image was acquired under the 40× objective in a GAD67-GFP slice (P4+6DIV).

Next, the different modes of membrane solubilization were examined. As discussed elsewhere herein, the process of mixed-micelle formation is fast and occurs at the membrane locations where the membrane of the target cell is saturated with detergent monomers. It was reasoned that the total amount of the delivered lysis buffer should be critical in determining the extent to which the membrane of the target cell would be solubilized. First, a smaller amount of lysis buffer was delivered to single cells without active lysate uptake. It was observed that the delivered SR101 dye slowly diffused out of the geometric single-cell boundary, into the live tissue or out of the live tissue, over the above time periods. The cell leftovers resembled the patches of the cell membrane (FIG. 11). This observation was consistent with the concept that the SDS-based lysis buffer can solubilize the membrane of a single cell following its intracellular delivery.

In the next set of experiments, it was reasoned that if enough lysis buffer were applied continuously, the membrane of the target cell would be solubilized more rapidly at some point during the continuous delivery. FIG. 12 shows how when a smaller amount of lysis buffer was first applied to the target cell, no immediate solubilization was observed. After continuously applying more lysis buffer to the same target cell in the later frames of FIG. 12, the membrane was observed to be rapidly solubilized. During the solubilization process, Alexa 555 dextrans were observed to exit the geometric confines of the cell and were eventually up-taken by the nearby capillary-action-driven suction channel (FIG. 12).

Single cells have different membrane areas and different volumes. A smaller cell should require less detergent to be lysed from inside. Importantly, the Inside-Out Lysis method first delivers the detergent-based lysis buffer into the intracellular space of the target cell. Thus, the Inside-Out Lysis method induces the denaturation of soluble proteins and the homogenization of the intracellular organelles in parallel with the detergent integration into the phoshpolipid bilayer of the membrane that precedes the formation of mixed micelles. There is a competition for detergent monomers between the intracellular soluble proteins and the cell membrane of the target cell. Thus, different levels of protein expression across single cells will also affect the amount of lysis buffer required for a complete and rapid solubilization of the cell membrane.

Without wishing to be bound by any particular theory, it is believed that any solubilization and/or chemical dissociation processes should be compatible with this method. From the chemical perspective, dissociation is distinct from solubilization. Solubilization is usually accomplished with detergents. However, different PH values, salt(s), other chemicals, and different concentrations could influence not only the solubilization process itself but also molecular interactions between molecules, resulting in dissociation. For example, urea and other denaturing or reducing (DTT) chemicals could be added. Strictly speaking, these chemicals lead to dissociation reactions that then facilitate solubilization. Accordingly, the present invention encompasses all processes that dissociate and/or solubilize cell components directly, and all processes that facilitate the aforementioned dissociation and solubilization processes.

Sometimes it is not desirable to completely solubilize the outer cell membrane. Instead it may be desirable to use it as a barrier first to solubilize/dissociate the intracellular components and then to extract the resulting liquid through a small opening in the membrane while keeping the overall membrane barrier still intact or mostly intact. The presence of the mostly intact overall membrane barrier would prevent contamination of the extract by other soluble molecules in the surrounding tissue. For a cell located deep inside the tissue, it is much harder to move the resulting liquid through a thick layer of tissue during collection, which will also lead to contamination by other soluble molecules in the tissue. Therefore, this alternative sample collection strategy might be preferable for sampling single cells deep inside the tissue.

The presence (at least temporary) of the intact membrane barrier, while the intracellular components are being solubilized and dissociated, is central to this invention. To accommodate the increase of volume inside the cell due to influx of reagents, detergents can be used. Detergents increase the membrane area while still maintaining the membrane barrier. Eventually, the outer membrane can be solubilized and dissociated or it can be kept mostly intact during withdrawal.

Single-Cell Resolution

Figure 32:
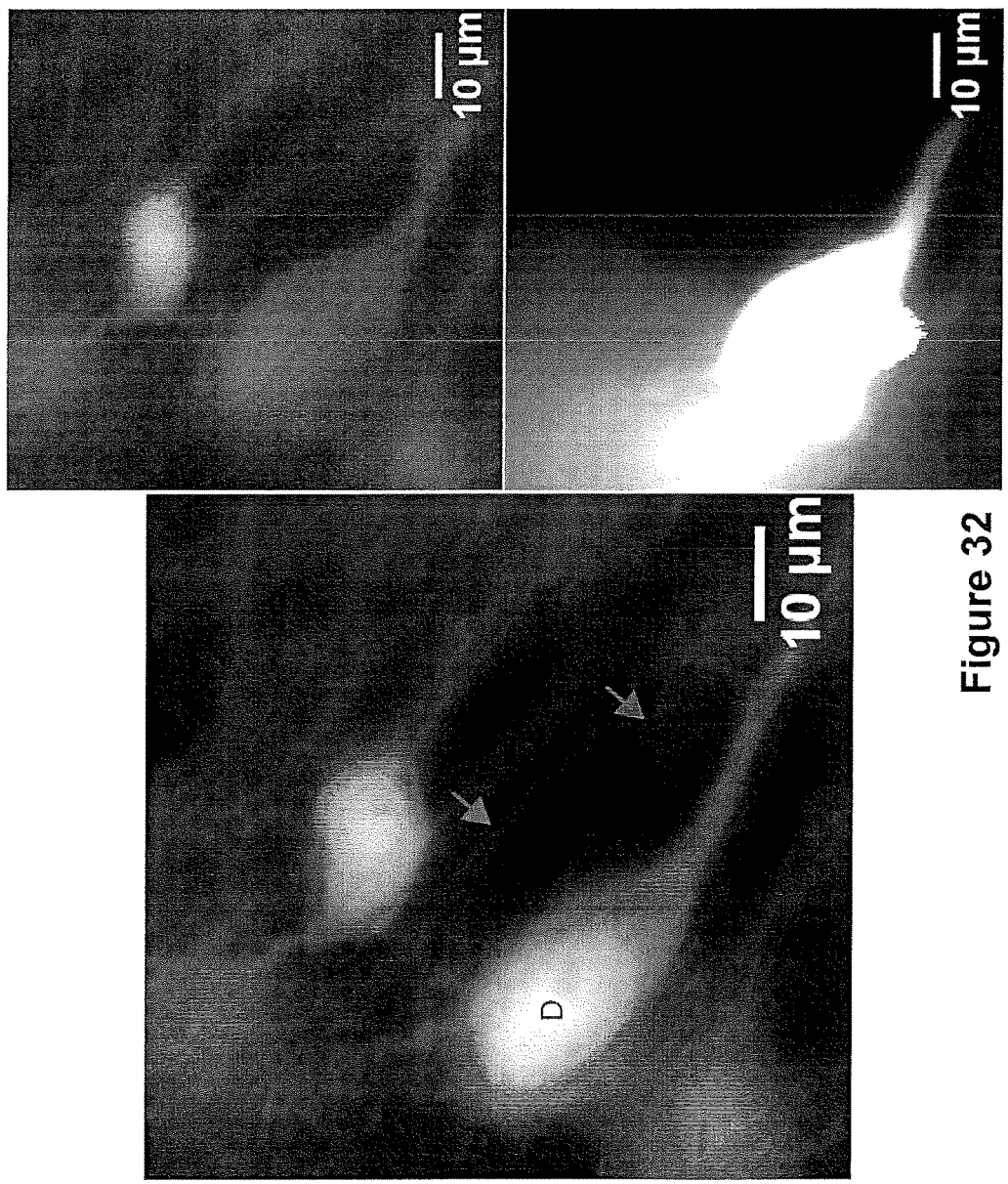
FIG. 32 is a series of photographs depicting how two adjacent dark cells are not visibly affected during the lysis buffer delivery stage of Inside-Out Lysis. The image on the left was acquired with high exposure before Inside-Out Lysis in order to capture the details of GFP distribution in the slice (GAD67-GFP strain, postnatal day 6+7 days in vitro). The two images on the right correspond to the same time point in the Inside-Out Lysis process of the first cell shown in FIGS. 7 and 8. The upper image on the right is the GFP frame. The lower image on the right is the SR101 frame showing the delivery of the SR101-containing lysis buffer to the target cell. The bright background section in the upper left corner of the lower image on the right is the fluorescence from the delivery micropipette. Two dark cells (arrows) can be observed next to the soma and next to the apical dendrite of the target GFP-expressing neuron. The focal point of lysis buffer delivery is designated by the letter D. The SR101 dye was contained strictly within the geometric boundary of the target cell and did not enter the two adjacent dark cells, even after extensive membrane growth.

As described elsewhere herein, the single-cell resolution of Inside-Out Lysis was studied by fluorescence imaging. Although not wishing to be bound by any particular theory, the growth of cell membranes and the simultaneous confinement of Alexa 555 dyes or SR101 dyes strictly within the geometric boundaries of target cells (see FIGS. 8, 10, 12 and 32) suggested that the membrane barrier of target cells was intact from the time point of lysis buffer delivery to the time point of visible membrane growth, and that single-cell resolution was preserved by the intact membrane barrier from the time point of lysis buffer delivery to the time point of extensive membrane growth in the Inside-Out Lysis process. As Alexa 555 or SR101 dyes filled the intracellular space of GFP-expressing target cells, strictly within their geometric boundaries, GFP fluorescence levels decreased immediately inside these cells (FIGS. 8, 10, 14, and 32). Capillary-driven suction was not applied in the experiment presented in FIGS. 8 and 32. Because the membrane barrier was intact at the time point of GFP fluorescence loss, GFP fluorescence loss likely resulted from intracellular GFP denaturation. Without being bound by any particular theory, it cannot be completely ruled out that some detergent monomers could pass through gap junctions to the surrounding cells within the time interval from the time point of lysis buffer delivery to the time point of visible membrane growth. However, neither Alexa 555 (MW 10000) nor SR101 (MW 606) were seen passing through gap junctions to surrounding cells at detectable levels (FIGS. 12 and 32).

At the time point of membrane solubilization, lysate was up-taken by the simultaneous perpendicular capillary-action-driven suction. As described elsewhere herein, the volume of the target cell was diluted approximately 1000 fold (from a few picoliters to 5-10 nanoliters) during the perpendicular uptake into the suction channel. In claiming single cell resolution, it was likely that such a rapid and simultaneous dilution (eventually 1000 fold) would eliminate any peripheral lysis in this last step of Inside-Out Lysis.

Experiments can be performed to examine whether the transient contact (1-4 seconds) between the diluted detergents and the peripheral surroundings of the target cell during the lysate uptake (last stage of Inside-Out Lysis) lead to contamination. A slice of GAD67-GFP hippocampus can be obtained and examined for a dark cell (not expressing GFP) surrounded by GFP-expressing cells. This dark cell can be lysed and measured to determine whether GFP is absent in the obtained lysate.

Printing Single-Cell Lysates

The lysate of each single cell sampled by Inside-Out Lysis was up-taken by a nearby capillary-action-driven suction channel and therefore is diluted in the sample solution surrounding the tissue slice (Hank's Buffered Salt Solution (HBSS)). The volume of the up-taken diluted lysate of each single cell was estimated to be approximately 5-10 nL. This volume estimate was calculated as follows: a customized bent suction micropipette was kept under positive pressure until the time point of lysis buffer delivery in order to ensure that it was empty before Inside-Out Lysis was triggered. The positive pressure was then released and the vertical suction was triggered by the capillary action of the micropipette. At the same time, Inside-Out Lysis of the target cell was triggered as well. After the lysate of the target cell was completely up-taken, the suction micropipette was robotically pulled out of the sample solution within a few seconds. Given the visible up-taken volume and given the known approximate geometry of the suction micropipette, the above-mentioned upper bound of 5-10 nL was derived.

Figure 13A:
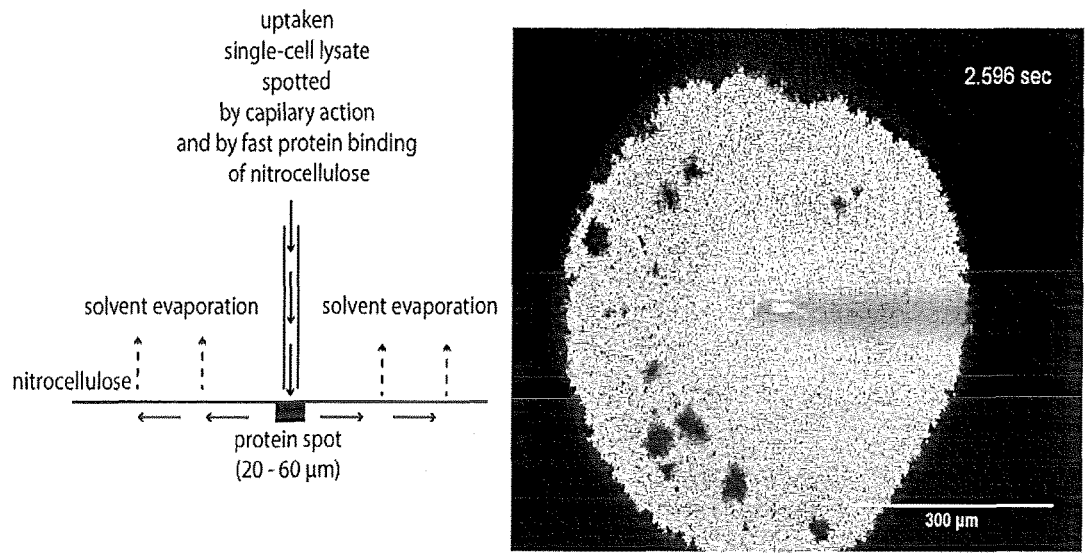
FIG. 13A and FIG. 13B depict printing single-cell lysates on a glass-mounted nitrocellulose pad.

In order to analyze the protein content of each single cell, each up-taken single-cell lysate was printed on a glass-mounted nitrocellulose pad. A method was developed to enrich the proteins of each diluted single-cell lysate (5-10 nL) on nitrocellulose within the boundary of a very small spot (20-50 μm). This method is based on the biophysical property of nitrocellulose to bind the proteins of the applied extract rapidly within a small area, whereas the solvent freely expands in a radial manner, driven by the capillary action of nitrocellulose, and naturally evaporates from a much larger area on nitrocellulose (FIG. 13A). By repeatedly applying the fractions of the total lysate volume onto the same spot on nitrocellulose in this manner, the protein content of each single-cell lysate was enriched within the boundary of a 20-50 μm spot (FIG. 13). As the single-cell lysate was concentrated within a small dense spot on nitrocellulose, the noise generated by the nitrocellulose was expected to be negligible.

Figure 13B:
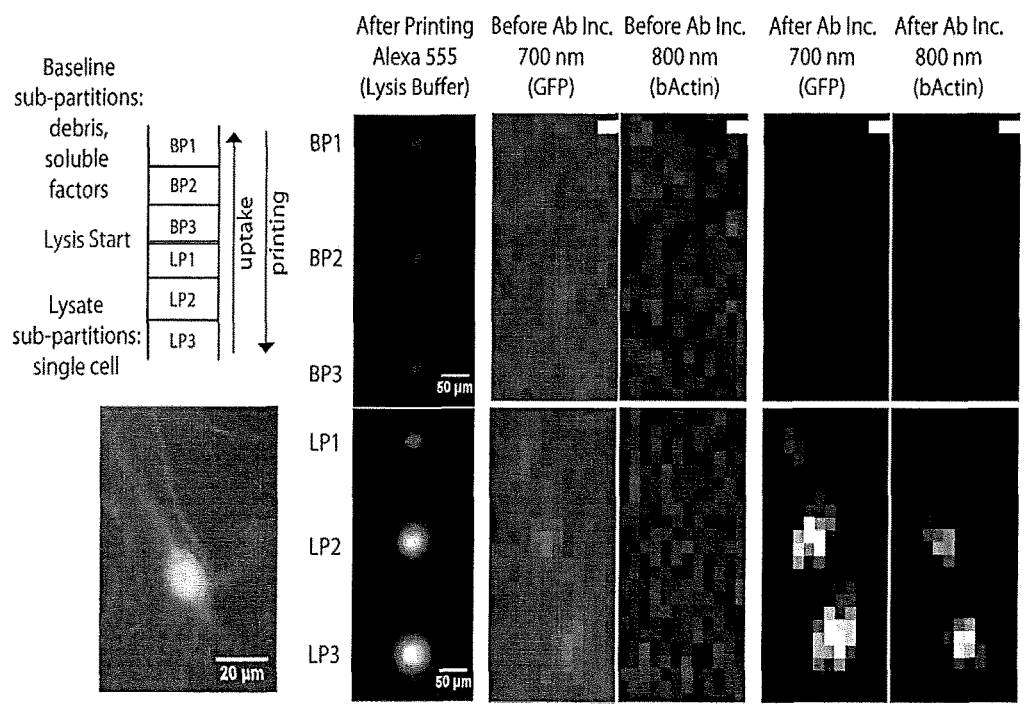

Live tissue surface may contain cell debris. The suction protocol also collected the surrounding medium (HBSS) and all the soluble factors within the tissue slice. Therefore, a protocol was developed which ensures the specificity of the recorded signals after printing single-cell lysates on nitrocellulose. After all the components of Inside-Out Lysis were positioned at the target cell, the capillary-action-driven suction was triggered by releasing its balancing positive pressure. After one minute, the Inside-Out Lysis process of the target cell was triggered. The only difference between these two time intervals was the delivery of lysis buffer to the target cell. After up-taking the lysate of the target cell, two partitions within the total up-taken volume remained: the baseline partition and the lysate partition (FIG. 13B). These two partitions were then printed in separate spots next to each other on the same nitrocellulose pad. The lysate spot(s) represented the results of Inside-Out Lysis and the baseline spot(s) represented all other factors that could possibly contribute to the measured signal in the lysate spot. This protocol was used in all subsequent measurements.

The lysate partition of one GFP-expressing somatostatin interneuron was subdivided into 3 separate spots on the same nitrocellulose pad (FIG. 13B). The baseline partition is also subdivided into 3 spots on the same nitrocellulose pad. Each spot was generated by 10 visually identical depositions, as estimated by the visible extent of radial solvent spreading in the nitrocellulose during each deposition. The total deposited volume was considered to be approximately equal across all spots. However, the corresponding GFP and β-actin signals were only observed in the lysate spots and were not observed in the baseline spots after antibody incubation. This example in FIG. 13B demonstrates that the lysate partition of each sampled single cell was divided into several sub-partitions. High protein signal density was achieved within the boundaries of even smaller spots on nitrocellulose, making it even easier to print just one sub-partition of the single-cell lysate partition on a nitrocellulose pad for protein analysis and to use the other sub-partitions of the same single-cell lysate partition for the analysis of other molecular classes.

Validation of Inside-Out Lysis

Two spatially separated single cells from the same organotypic hippocampus slice of a GIN mouse were lysed. One cell expressed GFP (somatostatin interneuron) and the other cell did not express GFP. The lysate sub-partitions of these two cells (3 spots for each cell, covering the whole lysate partition) and the corresponding baseline sub-partitions (3 spots for each cell) were printed on the same nitrocellulose pad as described elsewhere herein. Next the positive controls were added in order to assess antibody specificity. A titration curve of purified recombinant GFP and a titration curve of the average hippocampus lysate of a same-age GIN mouse were printed next to the single-cell lysate spots and next to the corresponding baseline spots on the same nitrocellulose pad with the help of an Aushon Arrayer.

Two negative controls were also printed. In order to obtain the first negative control, the delivery micropipette and the suction micropipette were positioned next to each other in the HBSS-filled sample chamber in the absence of a tissue slice.

Figure 14:
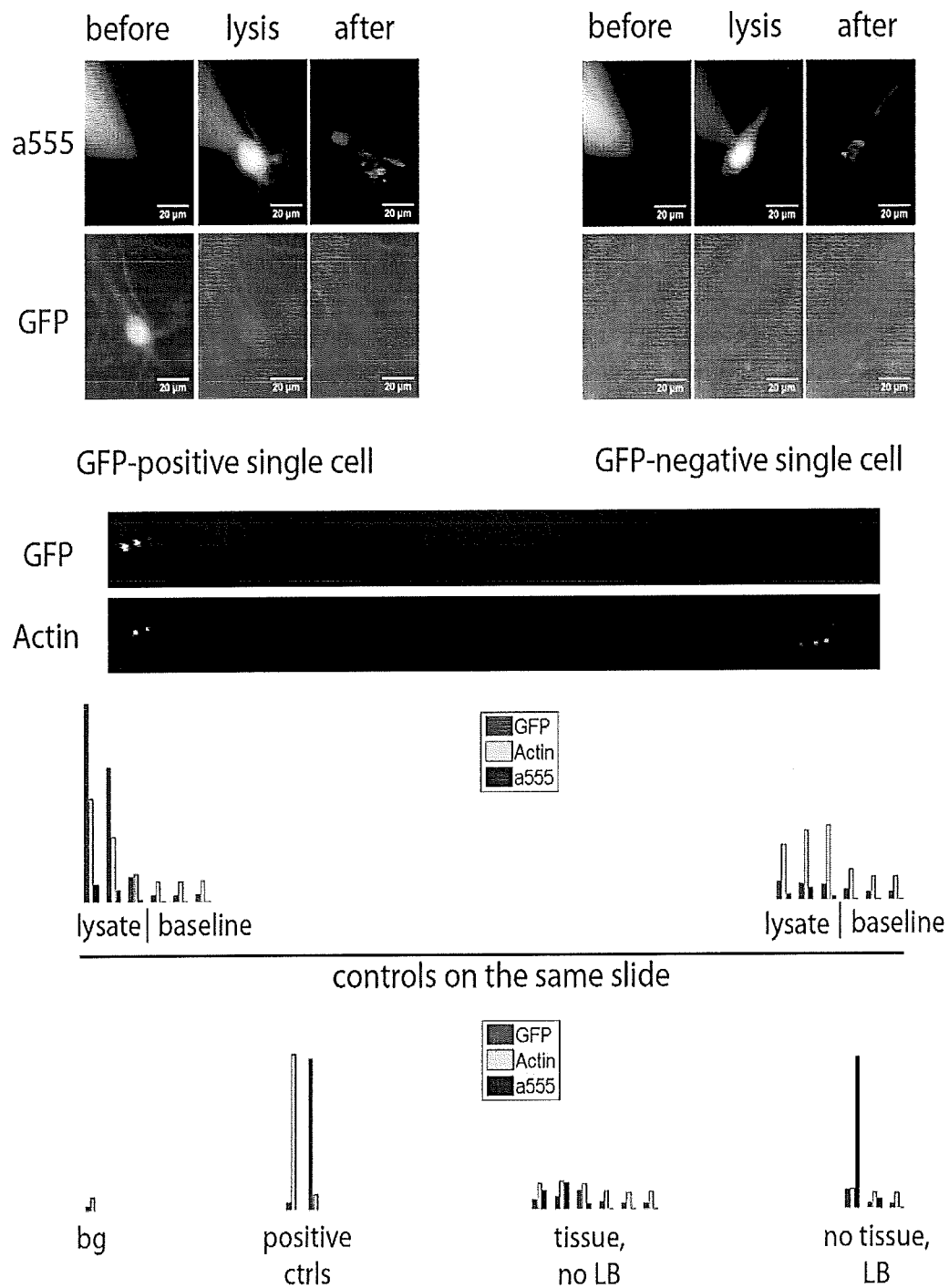
FIG. 14 is a series of illustrations depicting the validation of Inside-Out Lysis. Two cells were lysed in the same slice of a GIN mouse. One cell expressed GFP (somatostatin interneuron) and the other cell did not express GFP (CA3 pyramidal neuron). All the concurrent negative controls were negative. All the concurrent positive controls were positive. The entire lysate partition of each single cell was printed in three lysate spots respectively. The lysate spots of each single cell showed the expected signal distribution. The baseline spots were negative. These results demonstrate the successful use of single-cell lysate sub-partitioning, as the lysate partition of each cell in the experiment was subdivided into three sub-partitions.

The lysis buffer from the delivery pipette was then up-taken by the suction micropipette in a laminar flow and was printed on the same nitrocellulose pad in the same manner as the above-mentioned single-cell lysates, representing the first negative control ("no tissue, LB," FIG. 14). A stream of HBSS mixed with Alexa 555 dextrans was applied to a single cell in the hippocampus slice of a GIN mouse under the same settings that are usually used for Inside-Out Lysis, resulting in the absence of any lysis. The up-taken solution was printed on the same nitrocellulose pad in the same manner as the above-mentioned single-cell lysates, representing the second negative control ("tissue, no LB," FIG. 14). Overall, the baseline spots and the two above-mentioned negative controls encompassed all the possible non-specific factors that may contribute to the recorded signals in the lysate spots of the two single cells. The non-specific factors covered by the baseline spots and by the two negative controls included: lysis buffer (Tris·HCl 50 mM, SDS 2%, Glycerol 5%, NaF 1 mM, 0.5 mM AlexaD555 (10,000), Halt™ Protease Inhibitor Cocktail 3×, Halt™ Phosphatase Inhibitor Cocktail 3×), all printing/procedural factors and artifacts, convective flow factors, soluble factors in the tissue slice and cell debris on the tissue surface. The only event that was not covered by the set of baseline spots and the negative controls was the event of applying lysis buffer to a live single cell, which was exclusively covered by the lysate spots (FIG. 14).

The data in FIG. 14 show that the negative controls and the baseline spots did not generate any GFP or β-actin signals significantly above the background level. The positive controls were measured at the spots of the corresponding titration curves (concurrent standard curves) with signal intensities that were in the range of the signal intensities of the lysate spots. These positive controls show that the antibodies were specific (FIG. 14). As expected, the GFP levels in the average lysate were negligible after averaging all the cells of the GIN-mouse hippocampus. The sampled GFP-expressing single cell in FIG. 14 is the same cell displayed in FIG. 13. As expected, the three lysate spots of the GFP-expressing cell showed both GFP and β-actin signals, whereas the three lysate spots generated from the dark cell (CA3 neuron) showed only β-actin signals. Alexa 555 traces in FIG. 14 were measured immediately after printing the samples and were observed only in the lysate spots and the main negative control spots, but were not observed in the baseline spots. As all the negative controls provided negative results while all the positive controls provided positive results, it is likely that the GFP and β-actin signals in the lysate spots were exclusively associated with the event of applying lysis buffer to a live single cell. Thus, these signals necessarily originated from the single cells lysed by Inside-Out Lysis in the hippocampus.

Automation and Throughput

Figure 15:
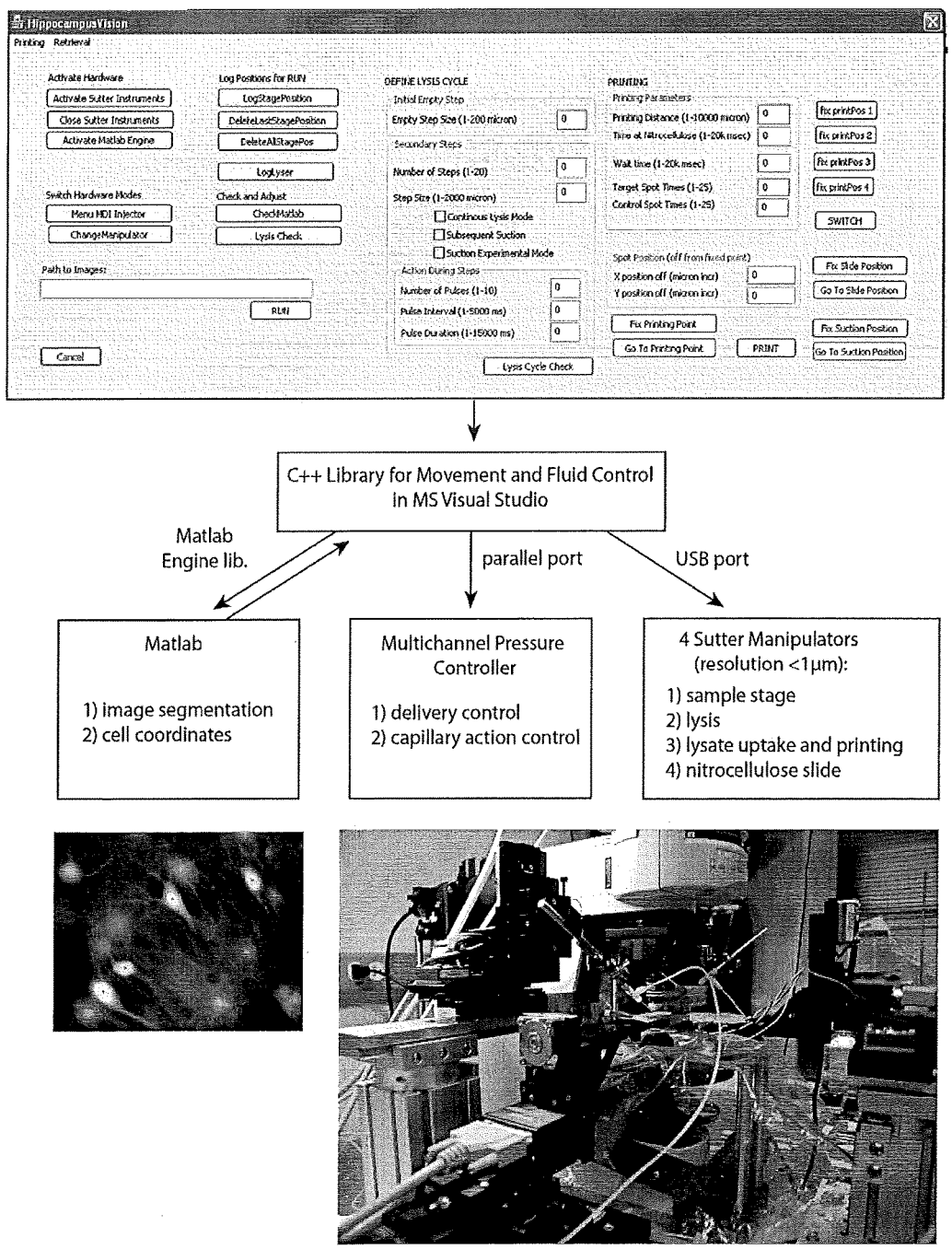
FIG. 15 is a series of images depicting the cell sampling and printing setup of the instant invention.

In order to interface the Inside-Out Lysis method with the lysate printing procedure, an extensive setup was built from ground up (FIG. 15). This setup facilitated the precise positioning of all the procedural components and enabled the rapidly coordinated movements of these components. Rapid programmable movements are required for switching from the Inside-Out Lysis method to the printing procedure on nitrocellulose. Because of the small liquid volumes (approx. 10 nL lysate+approx. 30 nL baseline) and the small apertures (10 μm) involved in the lysis and the printing processes, it was necessary to switch to the printing procedure within just a few seconds after the final single-cell lysate uptake. Importantly, the infrastructure for further extensive automation has also been built. A C++ library on top of the basic command library provided by Sutter Instrument Company was written to encode any sequence of movements of the 4 robotic arms at submicron resolution. This library was used for the complete automation of the lysis delivery process (FIGS. 7 and 8). A user interface was also built for convenience (FIG. 15).

Lysis buffer was delivered rapidly and in some instances in a fully automated fashion (FIG. 8). Given the current formulation of the lysis buffer, intracellular GFP denaturation was completed within the period of approximately 10 seconds after the initiation of lysis buffer delivery (FIG. 8). It took approximately 10 seconds to uptake the lysate after membrane solubilization (FIG. 12). Therefore, the whole process could take at least 10 seconds and at most 20 seconds after optimization. Because each initial tissue sample could provide enough material for tens of organotypic slices, the parallelization of the entire process could result in the effective throughput of 2 seconds per single cell for a given tissue sample.

Uptake of all Proteins of Target Single Cells

Single-cell lysates were completely deposited on nitrocellulose (FIGS. 13 and 14). Although not wishing to be bound to any particular theory, FIG. 22 suggests that cytosol-soluble proteins were completely uptaken because in vivo GFP fluorescence perfectly correlated with the recorded GFP signals after sampling and analyzing the lysates of four GFP-expressing cells and two dark cells as described elsewhere herein. Experiments can be performed to determine if all proteins of target single cells were denatured, solubilized, and uptaken. Experiments can be performed to determine whether all membrane proteins and all proteins clustered with membrane proteins were up-taken in the Inside-Out Lysis process. Different lysis buffer formulations containing stronger denaturing agents, such as urea, can be utilized in the Inside-Out Lysis process.

Example 2

Single-Cell Lysate Microarrays

Single-cell lysates and baselines were printed on a nitrocellulose pad, as described elsewhere herein. A high-precision arrayer was used to print the titration series of purified recombinant proteins and/or control lysates next to the printed spots of the single-cell lysates on the same nitrocellulose pad. A mixture of lanthanide-labeled antibodies was applied and each spot was sampled on nitrocellulose and the lanthanide signal detected with LA-ICP-MS (the laser ablation version of ICP-MS).

This strategy eliminated the disadvantages of Lysate Microarrays and CyTOF. Namely, this strategy did not require the sub-fractioning of the limited single-cell material and eliminates the auto-fluorescence of nitrocellulose, thereby resolving the limitations of Lysate Microarrays with respect to single-cell measurements. This strategy did not require tissue fixation/permeabilization and tissue disaggregation, thereby resolving the limitations of CyTOF with respect to tissue analysis.

At the same time, this strategy incorporated the advantages of the two methods. Namely, this strategy enabled the printing of concurrent standard curves and the rigorous validation of antibody probes as in Lysate Microarrays, as discussed elsewhere herein. At the same time, this strategy also incorporated the multiplexing capacity of lanthanide labeling.

The materials and methods employed in these experiments are now described.

Materials and Methods

Validation and Conjugation of Antibodies

All Cell Signaling Technology antibodies were ordered both in the standard and in the customized BSA-free formulations. The β-actin antibody acquired from Sigma and the GFP antibody acquired from Epitomics, were available in the standard BSA-free formulation. To measure proteins in Single-Cell Lysate Microarrays, the BSA-free antibodies were conjugated with the polymers carrying different lanthanides. All 8 antibodies were conjugated to different lanthanide labels in a one-to-one manner. The polymers and the lanthanides were acquired from DVS Sciences and their conjugation protocol was followed. The Cell Signaling Technology antibodies in the standard BSA-containing formulation were used for Western blots.

In order to obtain the average hippocampal lysate of a GIN mouse, two hippocampus samples were dissected from the same mouse and quickly placed into 200 µL of the same SDS-containing lysis buffer used in all other procedures. The tubes remained with the lysis buffer-submerged hippocampus samples in a 4° C. cold room for 2 hours. The hippocampus average lysate was then filtered to remove the extracellular matrix and DNA and stored in a −80° C. freezer. The concentration of proteins in the average lysate was measured by Micro BCA™ Protein Assay and was estimated at around 3.1 mg/ml. Because the pan-specific antibodies used in the Single-Cell Lysate Microarray experiments were previously pre-validated for general use within the format of Lysate Microarrays, only a Western blot experiment on the average hippocampus lysate was run to confirm the specificity of these antibodies in mice. The NuPAGE® SDS-PAGE Gel System (Life Technologies) was used. Each average lysate blot was incubated with the primary antibody of interest and with the β-actin antibody. After incubating the blots with the corresponding fluorescently labeled secondary antibodies, the signal intensities were acquired on a LiCor Odyssey scanner.

Detection by LA-ICP-MS

The Inside-Out Lysis procedure, the printing procedure for single-cell lysates, the printing procedure for the titration series, and the antibody incubation procedure described elsewhere herein were used in the Single-Cell Lysate Microarray experiments.

Thermo Electron X-Series ICP-MS (ICP-MS) and a New Wave 213 nm UV Laser (LA) were used for signal detection and spot sampling. The sensitivity and stability of the LA-ICP-MS instrument were both optimized prior to sampling the spots of interest on nitrocellulose pads. Usually, the sensitivity of LA-ICP-MS depends on argon flow. Argon flow is essential to sustain the inductively coupled plasma generated by a strong oscillating magnetic field via argon ionization. Argon flow is also used to introduce the sample into the plasma for atomization and ionization before the ionized elements enter the mass spectrometer. Thus, the optimization of the argon flow was crucial to achieve high sensitivity. After turning on the instrument, argon flow was optimized in ICP-MS with a standard salt solution in order to achieve high sensitivity. Subsequently, the instrument was switched to the laser ablation mode. The diameter of all laser-ablated spots was 80 µm. Laser strength was optimized to minimize the sampling of the glass base beneath each nitrocellulose pad.

The results of the experiments are now described.

Multiplex Measurements

Figure 17:
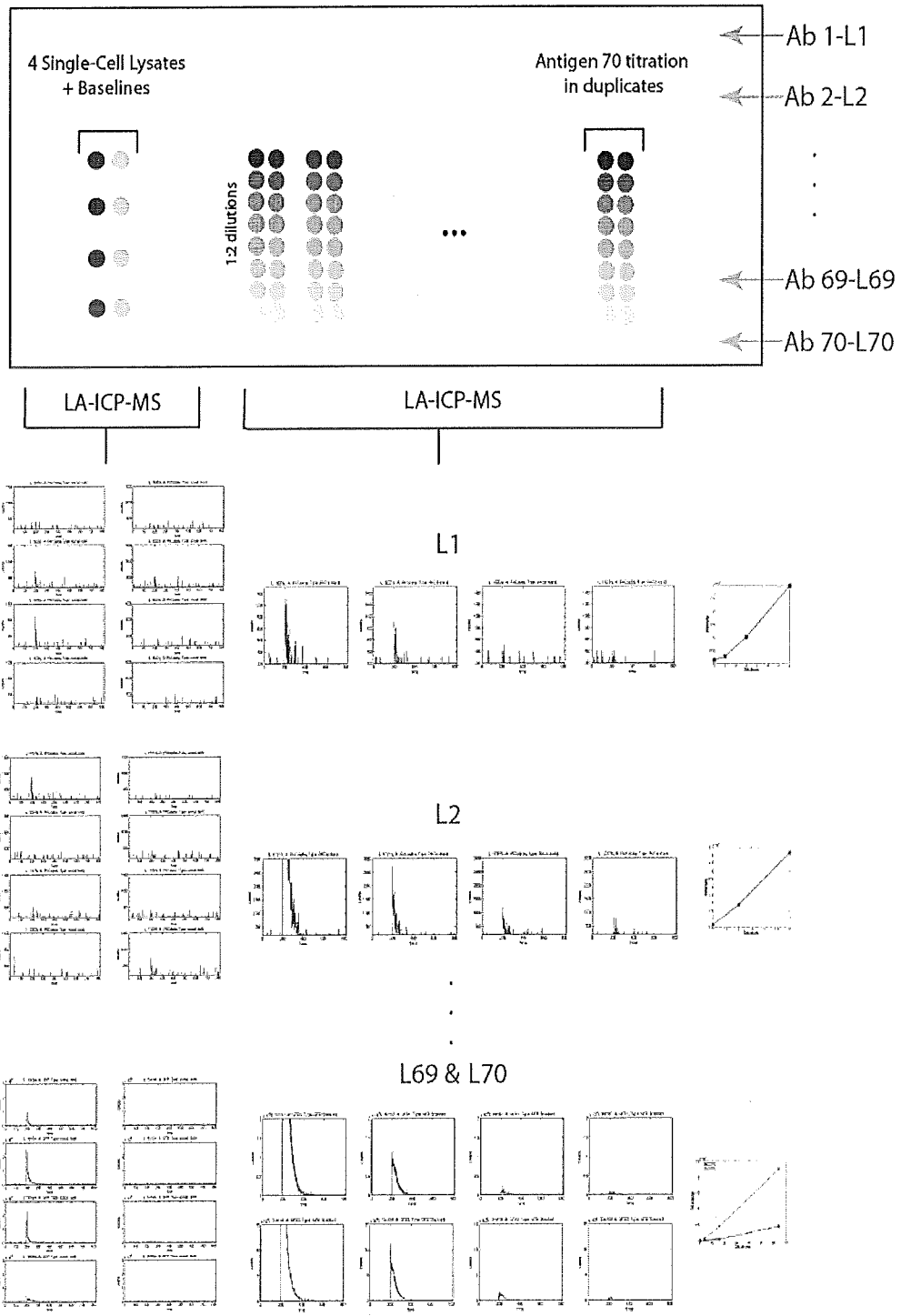
FIG. 17 is a series of graphs depicting Single-Cell Lysate Microarrays, which combine the analytical rigor of Lysate Microarrays with the multiplexing capacity of lanthanide-labeling.

By combining the advantages and by eliminating the disadvantages of Lysate Microarrays and lanthanide-labeling/CyTOF in one platform, multiplex analytical measurements of native proteins in single cells of solid tissues can be performed (Table 2). This platform may be referred to as Single-Cell Lysate Microarrays (FIG. 17).

TABLE 2

Single-Cell Lysate Microarrays enable multiplex analytical protein measurements of native proteins in single cells of solid tissues.
Unbold: disadvantages, Bold: advantages.

| Single-Cell Lysate Microarrays | Lysate Microarrays | CyTOF/Mass Cytometry |
|---|---|---|
| massive protein multiplexing | massive protein multiplexing | massive protein multiplexing |
| single-cell resolution | no single-cell resolution | single-cell resolution |
| no auto-fluorescence | auto-fluorescence | no auto-fluorescence |
| no tissue fixation/ permeabilization | no tissue fixation/ permeabilization | tissue fixation/ permeabilization |
| no tissue disaggregation | no tissue disaggregation | tissue disaggregation |
| concurrent titrations/standards | concurrent titrations/standards | no conc. titrations/no standards |
| reliable probe validation | reliable probe validation | poor probe validation |

The Lysate Microarray technology (also referred to as Reverse Phase Lysate Arrays) was first reported in 2001 (Paweletz et al., 2001, Oncogene 20:1981-1989). By robotically printing small lysate spots (~200 µm diameter) with high signal density on glass-mounted nitrocellulose pads, and by probing these nitrocellulose pads with pre-validated antibodies, high sensitivity and low sample requirements are achieved in highly multiplex protein measurements across an extensive set of samples and physiological conditions. Titration curves of control lysates and/or purified target proteins can be printed next to the unknown samples on the same nitrocellulose pads. These concurrent titration curves reveal the standard curves for each antibody probe. Thus, Lysate Microarrays compensate for signal non-linearity at low substrate levels and allow to map the recorded signal differences to the corresponding quantity differences.

The main bottleneck for the scalability of Lysate Microarrays is the number of available antibodies with invariantly low cross-reactivity across various lysates. Most antibodies cross-react with unspecific antigens. In contrast to Western blot, the cross-reactive signal component in Lysate Microarrays cannot be separated from the specific signal component by size separation of proteins. In Lysate Microarrays, any given lysate spot contains a homogenous mixture of all proteins of the original sample and thus any cross-reactive signal will also contribute to the total recorded signal in each lysate spot. The following example demonstrates how the cross-reactivity of antibodies can obscure the specific signal component in Lysate Microarray measurements.

Let
P(Ab binds|Target)=0.99,
|P(Ab binds|nonTarget1)=0.01,
P(Ab binds|nonTarget2)=0.05,
Target=1000,
nonTarget1=70,000,
nonTarget2=29,000,
Then
P(Ab binds)=0.0314,
E(# total Ab bindings)=3140,
E(# specific Ab bindings)=90.

The above example shows that given an antibody and a relatively low number of targets in the spotted homogenous mixture of proteins, the cross-reactive signal component (2150) is at least twice as large as the specific signal component (990). This example also demonstrates that antibody cross-reactivity can be parameterized by three parameters: 1) the proportion of target proteins in the total mixture, 2) the distribution of various non-target proteins in the mixture and 3) the inherent binding probabilities of the given antibody to targets and to non-targets. Many crucial kinases and phosphatases occur in low copy numbers (100-1000 in single cells). The distribution of non-target proteins also varies from cell to cell within a cell type and from cell type to cell type. The purpose of Lysate Microarrays is to measure the levels of crucial proteins in unknown samples. Therefore, the binding probabilities of antibodies are the only parameter that can be optimized in order to minimize the cross-reactivity of antibodies in Lysate Microarrays. An extensive screening test is required to identify the antibodies with optimal binding probabilities.

Figure 16:
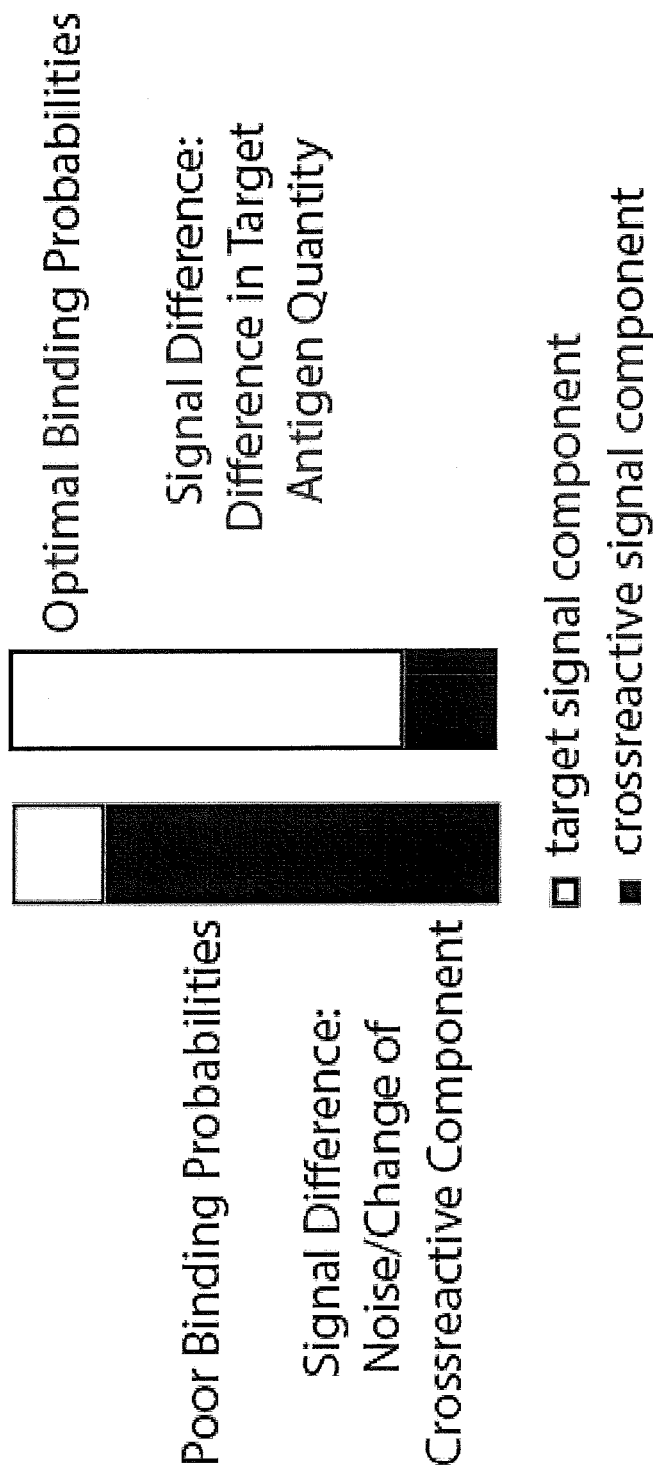
FIG. 16 is an illustration depicting two possible categories of antibodies in the format of Lysate Microarrays. In contrast to Western blot, proteins cannot be separated by size in Lysate Microarrays. As a consequence, antibodies with optimal binding probabilities (second case from the left) and thus with invariantly low cross-reactivity are required. Once a set of antibodies in this category is validated, analytical protein measurements can be accomplished in unknown samples with Lysate Microarrays.

Sevecka had designed a set of screening tests for pan-specific antibodies (Sevecka et al., 2011, Mol. Cell Proteomics 10: M110.005363). For each tested antibody, their first test required the presence of a single dominant band of correct size in the Western blot across all the lysates of 17 different human cell lines, while their second test required that the target levels measured in Western blot should also highly correlate (>0.75) with the corresponding levels in Lysate Microarrays across the same 17 human cell lines. Each cell line expressed different levels of target antigens and presumably different levels of non-target proteins. If the binding probabilities of a given antibody are optimal, then it will be specific across different cell lines, because the cell-line-dependent variation of the cross-reactive component will not affect the accurate detection of the different target levels. This will lead to a high correlation between Western blot and Lysate Microarrays. If the binding probabilities of a given antibody are poor, then the cell-line-dependent differences and the noise of the cross-reactive component will obscure the true target levels in Lysate Microarrays, leading to a low correlation (FIG. 16). The second test by Sevecka et al. is equivalent to 17 independent Bernoulli trials, because every distinct cell line can be considered as a Bernoulli trial and the tested antibody can be considered as a biased coin. Given 17 or approximately 17 'good' outcomes after 17 independent trials, the probability is high that this particular antibody (coin) will be specific (biased=good binding probabilities) in any other cellular context (future trials) and thus can be used to make accurate measurements across unknown cell types. 10% of 129 tested by Sevecka et al. pan-specific antibodies passed these two tests. This selected set of antibodies is generally valid for measuring proteins in unknown samples within the format of Lysate Microarrays.

Lysate Microarrays are not appropriate for single-cell measurements. The multiplexing capacity of Lysate Microarrays is based on the subdivision of the original homogenous sample into its sub-fractions and on printing these sub-fractions on multiple spatially separated nitrocellulose pads for the subsequent incubation of each pad with a different antibody. In the case of a single cell, the original protein material is very limited and should not be subdivided for the sole purpose of protein multiplexing. Signal acquisition in Lysate Microarrays is achieved by scanning fluorescently labeled secondary antibodies. In this setting, auto-fluorescence of nitrocellulose can also be prohibitively high, when low amounts of single-cell material are to be analyzed. Nitrocellulose auto-fluorescence is another reason why Lysate Microarrays are not appropriate for single-cell measurements.

The possibility of detecting metal-labeled probes by atomic mass spectrometry was first reported in 2002 (Quinn et al., 2002, J. Anal. At Spectrom 17:892-896). By conjugating different rare metal labels to different affinity-based probes in a one-to-one manner, the multiplexing capacity of any probe-based measurement can be significantly increased due to the large number of existing rare metal elements. As the probed sample is being processed through the 5,000-10,000° C. plasma (inductively coupled plasma mass spectrometry, ICP-MS), all molecules of this sample are atomized and ionized before entering the mass spectrometry module. Because rare metals do not occur in most biological systems at significant levels, the measured counts of rare metals then correspond to the levels of the respective labeled probes being present in the probed sample. For example, antibodies can be conjugated to the polymers containing lanthanide chelators. These lanthanide-labeled antibodies enable highly multiplex detection of proteins. Lanthanide-labeling has been developed and commercialized in the context of the CyTOF/Mass Cytometry instrument by DVS Sciences (Bendall et al., 2011). This instrument emulates flow cytometry. Thus, CyTOF also shares all the limitations of flow cytometry with respect to analyzing single cells in solid tissues (Table 2).

Antibody Validation and Lanthanide-Labeling

A set of pan-specific antibodies that had previously been validated by Sevecka et al. for the general use in Lysate Microarrays as described elsewhere herein were obtained for the development of Single Cell Lysate Microarrays. Out of 129 pan-specific antibodies tested across 17 different human cell lines, Sevecka et al. were able to identify 12 antibodies of high general specificity for analytical studies with Lysate Microarrays (Sevecka et al., 2011, Mol Cell Proteomics 10:M110.005363). A subset of these 12 antibodies was used for the development of Single-Cell Lysate Microarrays. Because the Inside-Out Lysis method for sampling single cells in organotypic cultures of mouse hippocampi was to be used, each antibody in the selected subset needed to also be antigenic in mice. Kinases were selected as target antigens because of their crucial role in cell signaling and their expected low relative abundances in single cells. Successful measurements of these kinases with Single-Cell Lysate Microarrays would constitute a confirmation of the high sensitivity of this method. FAK, PKCδ, PKCα and PAK1 were selected as target kinase antigens. A validated antibody for β-catenin was also included. Because rare GFP-labeled somatostatin interneurons in the organotypic hippocampus cultures of GIN mice were to be lysed, two GFP-specific antibodies were added to the overall set of antibodies. One of these GFP-specific antibodies was the same antibody used in the validation of Inside-Out Lysis, as described elsewhere herein.

Figure 18:
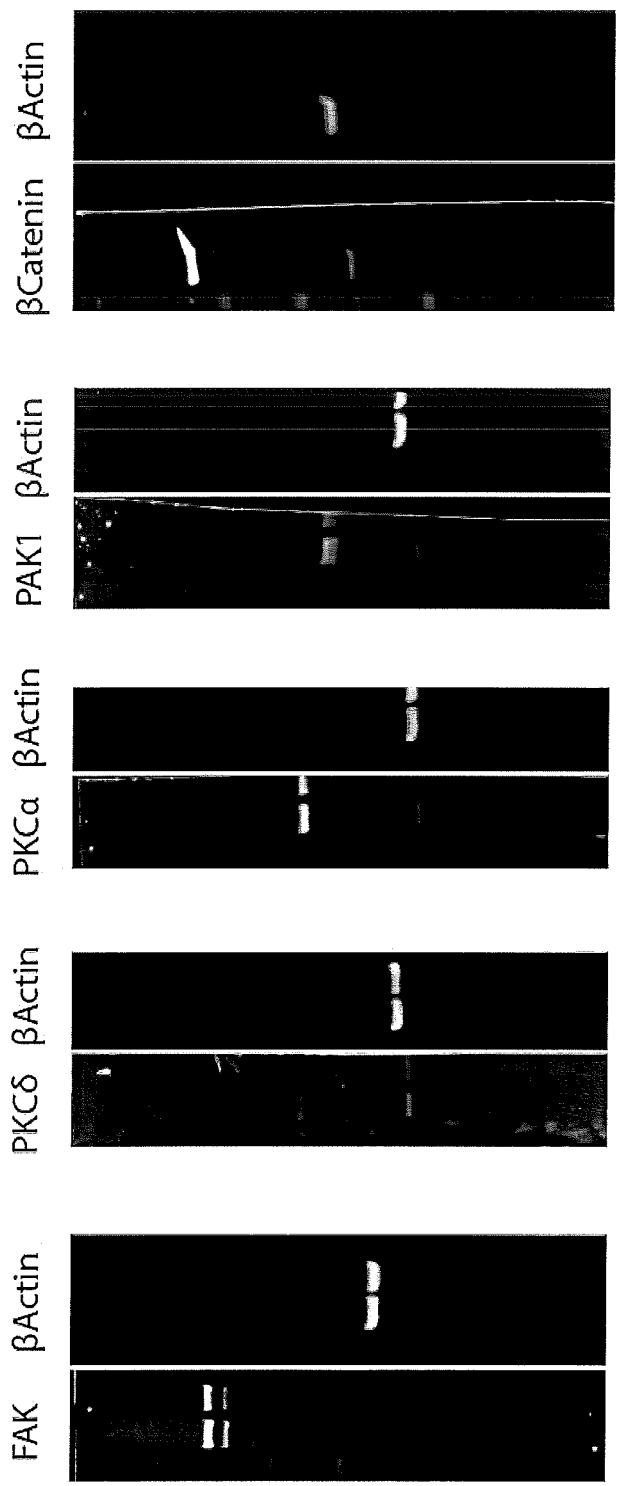
FIG. 18 is a series of photographs depicting additional antibody validation. Each pan-specific antibody, previously validated for Lysate Microarrays by comparing the signal distribution in Lysate Microarrays with the corresponding signal distribution in Western blots across 17 human cell lines, gave a single dominant band in the Western blots performed on the average lysate of GIN mouse hippocampus. The GIN mouse was of the same age as the GIN mice used in later experiments. The second band in PKCδ, PKCα, PAK1 and β-catenin blots came from the fluorescence of the secondary antibody against the primary β-actin antibody.
Figure 19A:
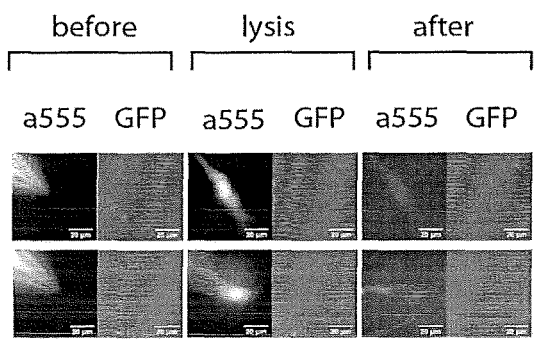
FIG. 19A, FIG. 19B, and FIG. 19C depict Single-Cell Lysate Microarray data. In the upper segment, a555 stands for Alexa 555.
Figure 19A:
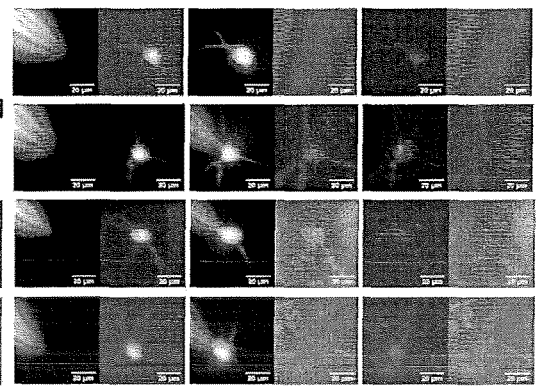
Figure 19A:
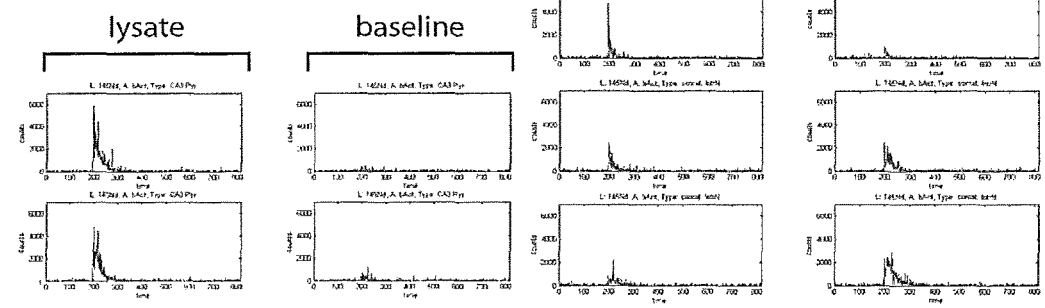
Figure 19A:
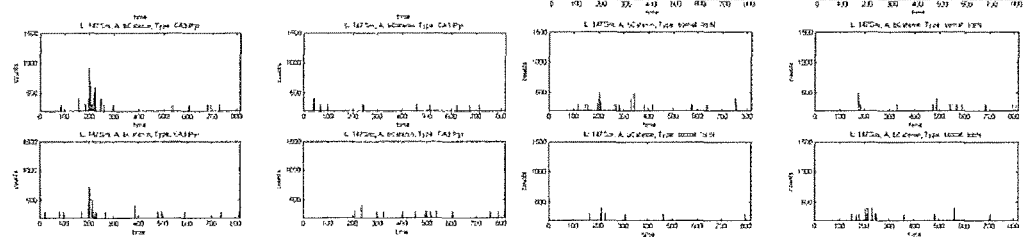
Figure 19B:
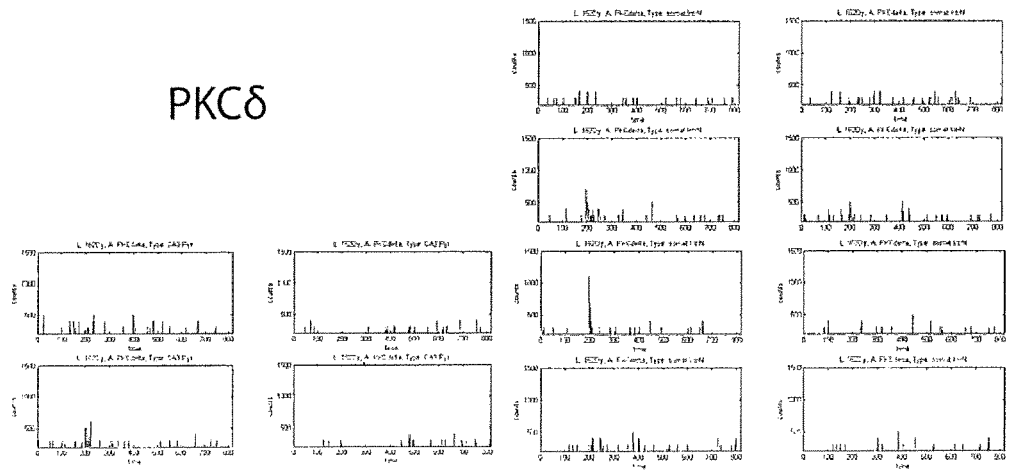
Figure 19B:
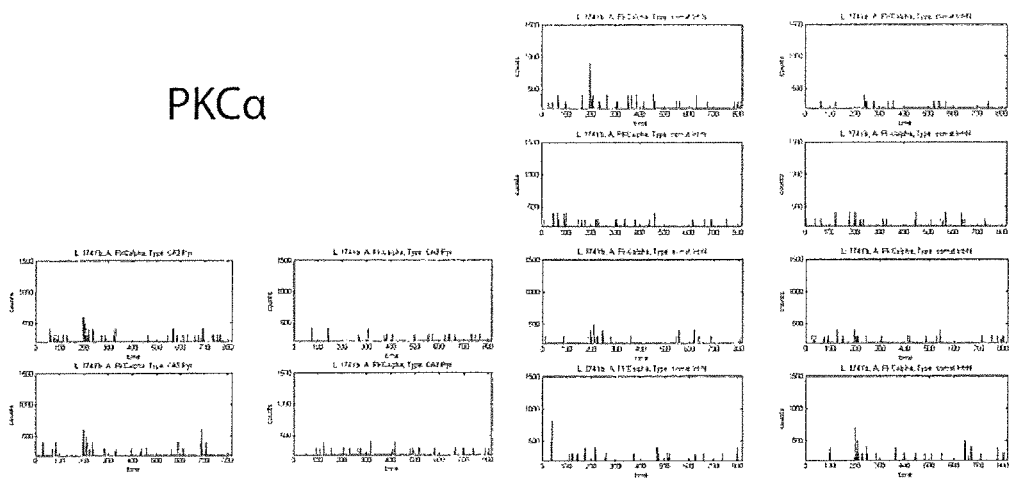
Figure 19B:
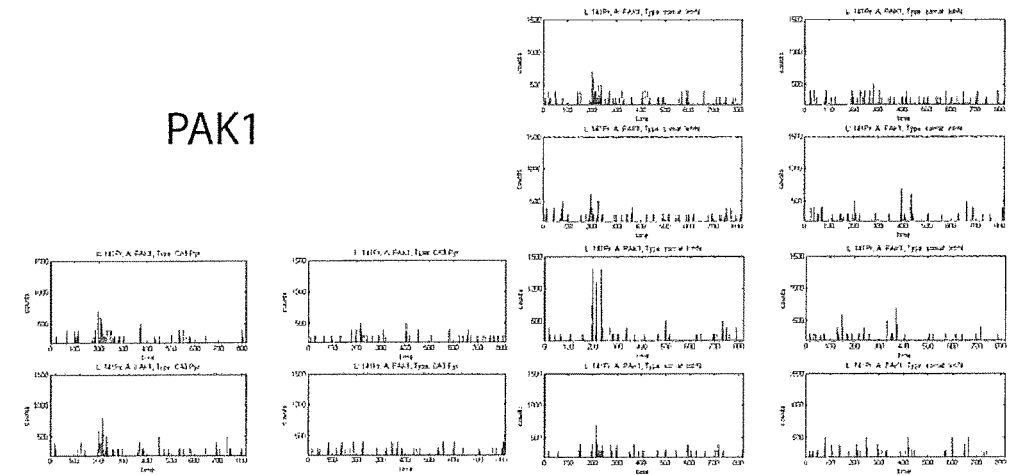
Figure 19C:
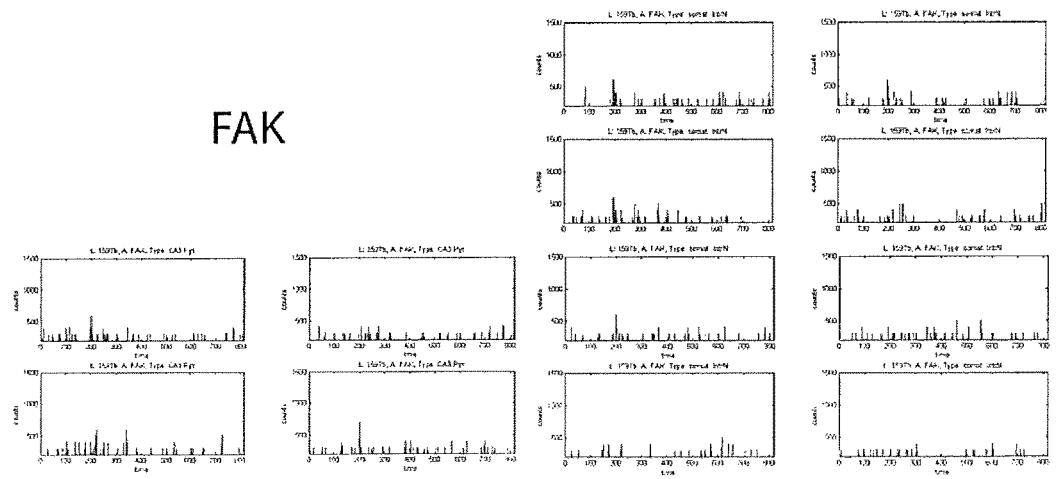
Figure 19C:
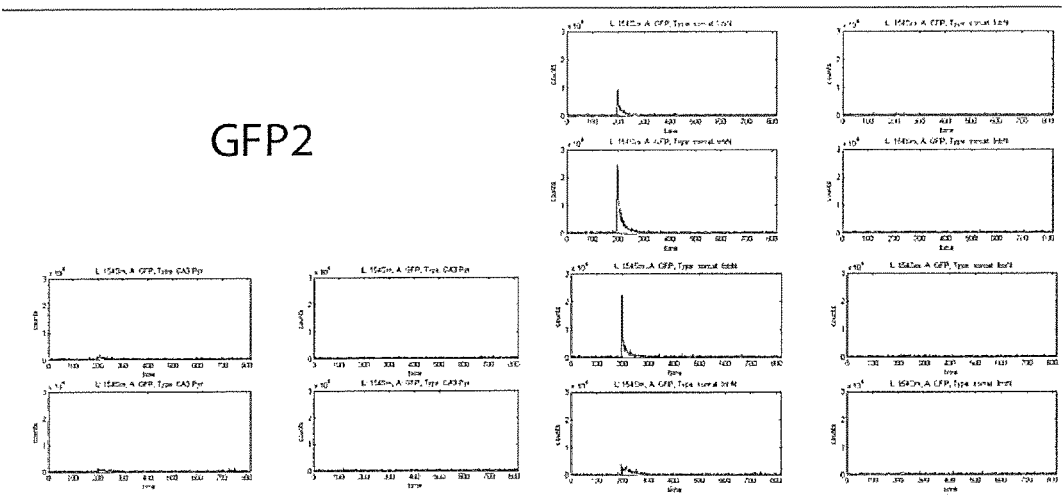
Figure 19C:
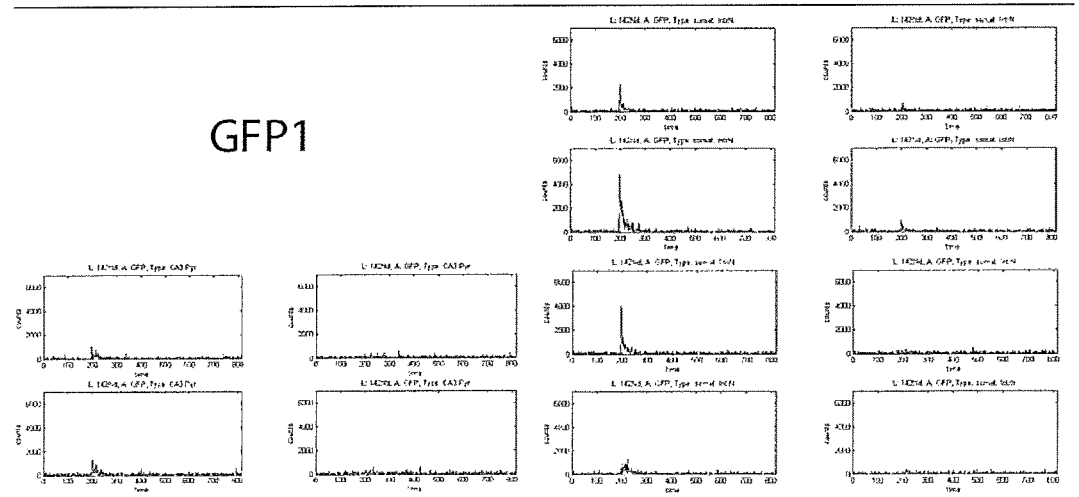

Because the selected antibodies against kinases and β-catenin had previously been validated across 17 human cell lines and were expected to perform well in any unknown context as discussed elsewhere herein, it was reasoned that a simple confirmation of their specificity in mice was sufficient. A Western blot experiment was performed on an average lysate of the hippocampus of a 6-day old GIN mouse. All these antibodies had a clear dominant band of the correct size, thus confirming their specificity against mouse antigens (FIG. 18). GFP antibodies were not independently validated and were expected to be specific, as confirmed in later experiments.

Next, the purified BSA-free formulations of the selected set of antibodies were obtained for subsequent lanthanide conjugation. Lanthanide conjugation was performed according to the protocol provided by the manufacturer of the obtained lanthanide polymers (DVS Sciences). The list of antibodies and the corresponding lanthanide labels is provided in Table 3.

TABLE 3

Lanthanide-Labeling of the Selected Set of Antibodies Previously Validated for Lysate Microarrays and then Confirmed by Western Blot.

| Antigen | Antibody | Lanthanide Label |
| --- | --- | --- |
| βActin | A1978, Sigma | Nd145 |
| PKCδ | 2058, CST | Dy162 |
| PKCα | 2056, CST | Yb174 |
| PAK1 | 2602, CST | Pr141 |
| FAK | 3285, CST | Tb159 |
| βCatenin | 9582, CST | Sm147 |
| GFP1 | S2038, Epitomics | Nd142 |
| GFP2 | 2956, CST | Sm154 |

Multiplex Analytical Protein Measurements of Native Proteins with Single-Cell Lysate Microarrays Four GFP-expressing somatostatin interneurons were sampled from 2 slices of live organotypic hippocampus cultures of a GIN mouse (postnatal day 5+7 days in vitro). Two putative CA3 pyramidal neurons from the CA3 region of the same hippocampus slices were also sampled. These 6 single-cell lysates and their corresponding baseline spots were printed on the same glass-mounted nitrocellulose pad. For each single-cell lysate, one spot with the entire lysate partition and one spot with the baseline partition were each printed, as described elsewhere herein. For each single-cell lysate, one spot (30 depositions) with the entire lysate partition and one spot (31-32 depositions) with the baseline partition were printed, as described elsewhere herein. For each cell, the deposited amount of liquid in the lysate spot was approximately equal to the deposited amount of liquid in the corresponding baseline spot. All in vivo GFP intensities were also recorded prior to single-cell lysis under the same settings of the imaging setup. Because all the imaged and sampled cells were close to the surface of the two hippocampus slices, light scattering should not have had any significant effect on the recorded intensities of in vivo GFP fluorescence of these cells. The sampled CA3 pyramidal neurons did not express any GFP at the detection sensitivity of the imaging setup.

Next, the titration series of purified recombinant PKCα, PKCδ and GFP were printed by the high-precision Aushon Arrayer on the same nitrocellulose pad next to the printed single-cell lysates and next to their baselines. The titration series of the average hippocampus lysate of a GIN mouse was also printed next to these titration series of recombinant proteins. All spots were marked by making 10 μm-large incisions on the nitrocellulose pad next to the printed spots in order to maintain the visual coordinates of all the printed spots throughout the subsequent washing and antibody incubation steps.

The same set of washing and antibody incubation steps were applied to the printed glass-mounted nitrocellulose pad as described by Sevecka (Sevecka et al., 2011, Mol Cell Proteomics 10:M110.005363). In a different set of experiments, it was determined that the following concentrations of the 8 lanthanide-labeled antibodies bring the corresponding signals generated by single-cell lysates into the sensitivity range of the LA-ICP-MS detector: 0.66 μg/ml for the conjugated β-actin antibody and 3.3 μg/ml for all the other conjugated antibodies. After antibody incubation, the spots of the printed single-cell lysates, the spots of their baselines, and the spots of all the printed titration series were sampled with the help of a tuned and calibrated LA-ICP-MS instrument during a single acquisition run. By adjusting the laser strength and by recording the traces of 85Rb and 88Sr, it was ensured that the glass base of the nitrocellulose pad was not sampled by laser ablation to a significant extent. A control pulse of high laser intensity was also applied to the blank region of the nitrocellulose pad in order to ensure that by sampling a significant amount of glass (indicated by 85Rb and 88Sr traces) and nitrocellulose (indicated by tiny visible nitrocellulose holes), no lanthanide traces could be detected. Thus, after washing and antibody incubation, glass and nitrocellulose alone did not lead to the detection of lanthanides.

Obtained measurements by LA-ICP-MS are presented in FIG. 19. In the first upper segment of FIG. 19A, each row represented 3 time points of the Inside-Out Lysis process of each sampled cell ('before', 'lysis', 'after'). For each cell, the three select time points of the lysis process show that, as expected, GFP lost its fluorescence after the intracellular space was filled with the SDS-containing lysis buffer. The last time point in each row ('after') showed that the contents of the target cells were eventually up-taken by the simultaneous capillary-action-driven suction channel. In the other segments of FIG. 19, the following LA-ICP-MS sampling procedure for sampling each spot was used. The sampling procedure for sampling each spot on the nitrocellulose pad by the LA-ICP-MS instrument took 3 minutes (time axis in FIG. 19 is number of recorded time frames by the LA-ICP-MS detector within the sampling procedure). In the first interval of each sampling procedure, the instrument noise was measured by acquiring the noise data prior to laser ablation. Then a sequence of laser pulses was applied to the spot location on the nitrocellulose pad. This sequence of fast laser pulses was applied for the duration of 60 seconds. The residual time within each sampling procedure was spent waiting until the continuously measured counts of elements from the most recently sampled spot returned to the noise levels of the instrument. Using this sampling procedure for each spot, all the spots of single-cell lysates, baselines and titration series were sampled on the above-described nitrocellulose pad.

The baseline spots containing HBSS solution, tissue debris and/or soluble tissue factors showed low signal in most cases (cells 1 to 4; cells are numerated from left to right and from top to bottom). The baseline spots of the last two somatostatin interneurons (cell 5 and cell 6) showed significant β-actin signals with relatively low β-actin signals in the corresponding lysate spots. The baseline spots of the other 4 cells (cells 1 to 4) did not generate any signals significantly above the instrument noise levels across all 8 channels. The volume printed in each baseline spot was larger or approximately equal to the volume printed in each lysate spot, as described elsewhere herein. Each baseline spot of the first 4 cells (cells 1 to 4) encompassed all the possible sources of procedural noise that could originate from Inside-Out Lysis, from printing and/or signal detection procedures. These sources of procedural noise included: HBSS solution, tissue debris, soluble factors in tissue, the printing process, incubation/washing steps, and LA-ICP-MS noise. Therefore, any signal differences recorded at the time of laser-firing in the lysate spots of the first 4 cells did not originate from any subset of the above-mentioned procedural noise sources. Thus, the signal levels in the lysate spots of the first 4 cells (cells 1 to 4) did not originate from the non-specific signal levels of the baseline components. The signals in and the signal differences across the lysate spots of the first 4 cells originated from the differences in antibody binding to the printed single-cell lysates.

Figure 21:
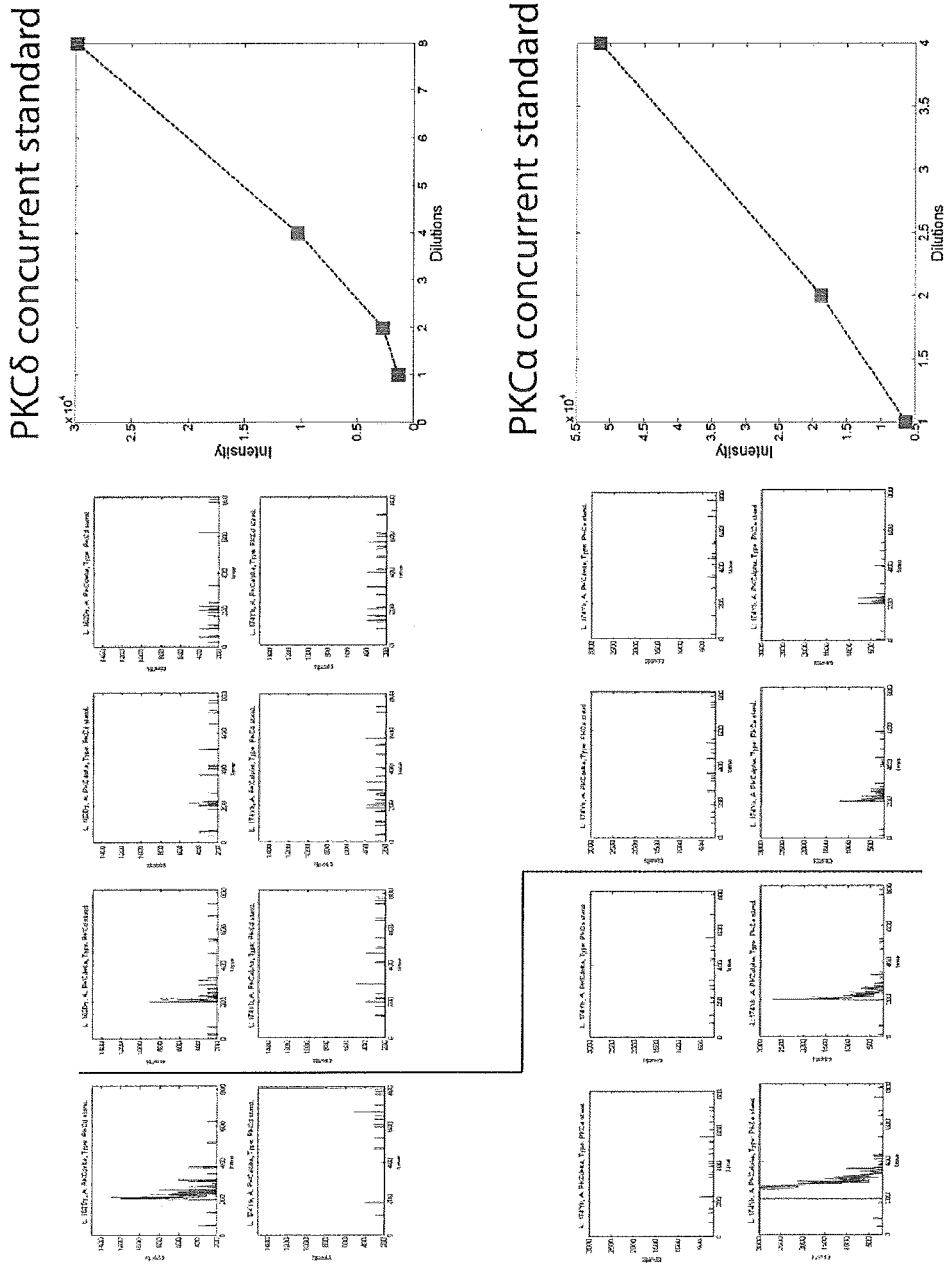
FIG. 21 is a series of graphs depicting a concurrent PKCδ and PKCα titration series revealing the standard curves. The titration series of PKCδ and PKCα were printed on the same glass-mounted nitrocellulose pad, on which the single-cell lysates in FIG. 19 were also printed and measured. All titration series were printed by the high-precision Aushon Arrayer. The line delineates the dynamic range within which the recorded signals of PKCδ and PKCα in the single-cell lysate spots were confined (compared to FIG. 19). The nonlinear nature of the standard curves also makes the inclusion of such concurrent standards in any single-cell measurement necessary (FIG. 2).

Inspection of the recorded signals across all 8 dimensions suggested that there were significant differences in signals between single cells within each dimension (FIG. 19). These differences did not come from procedural noise sources. It was likely that these signal differences represented the differences in protein quantities because the data in FIG. 14 showed that lysis buffer components had no detectable effect on antibody binding. As all the kinase antibodies and the β-catenin antibody were validated across 17 different cell-line contexts in the format of Lysate Microarrays, these antibodies have very low cross-reactive components in any cell type. FIG. 21 depicts the expected signals obtained from the concurrent titration series of purified PKCδ and PKCα on the same nitrocellulose pad, on which the single-cell lysates and their corresponding baselines were also printed and sampled (FIG. 19). By looking at the concurrent titration series of PKCδ and PKCα (FIG. 21), it was observed that lanthanide-labeling did not affect the specificity of the validated antibodies. The measured differences in signals between single cells within each of the 8 dimensions (channels) thus likely originated from the differences in the corresponding quantities of target proteins in these lysate spots.

Figures 22A, 22B:
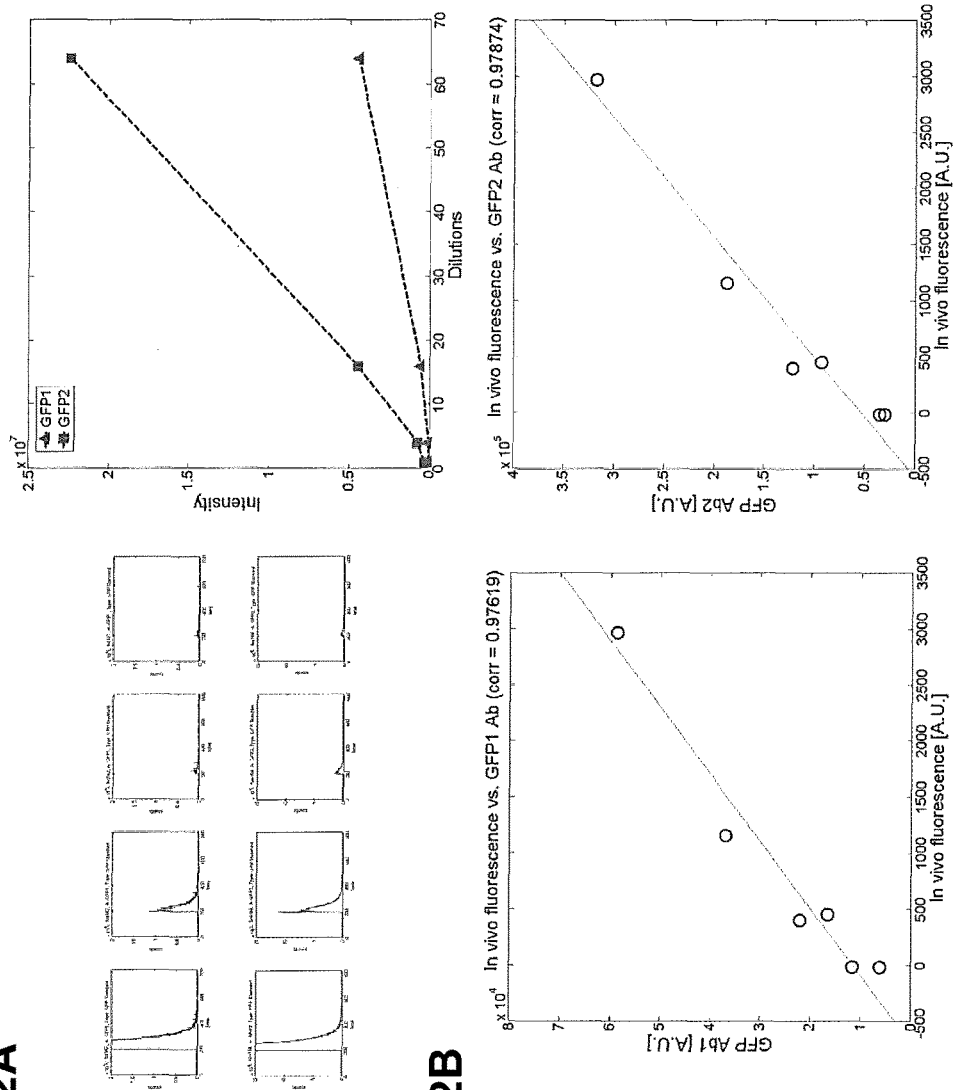
FIG. 22A and FIG. 22B depict results from GFP titration series and measurements.

Because the in vivo GFP fluorescence levels of the sampled somatostatin interneurons and CA3 neurons were recorded under the same settings of the imaging setup prior to Inside-Out Lysis, the recorded in vivo GFP fluorescence levels were compared with the corresponding measurements across the same 6 sampled single cells. FIG. 22B shows an almost perfect correlation between the in vivo GFP fluorescence recorded before Inside-Out Lysis and the measured GFP levels in the corresponding single-cell lysates that were simultaneously probed with two different GFP antibodies in Single-Cell Lysate Microarrays. This was an additional validation of the Inside-Out Lysis method. As described elsewhere herein, and without being bound by any particular theory, the high correlation values suggest that most soluble proteins were uptaken from single cells during the Inside-Out Lysis method. Four spots of the GFP titration series were sampled and the concurrent standard curves for each of the two GFP antibodies was obtained. Because the conjugation procedure for each GFP antibody was the same during the incubation procedure and because the concentrations of the two antibodies were the same, it is likely that the different slopes of the GFP standard curves, derived from the same four spots of the same titration series in FIG. 22A, resulted from the corresponding differences in the KD values between these two GFP antibodies.

Figure 20:
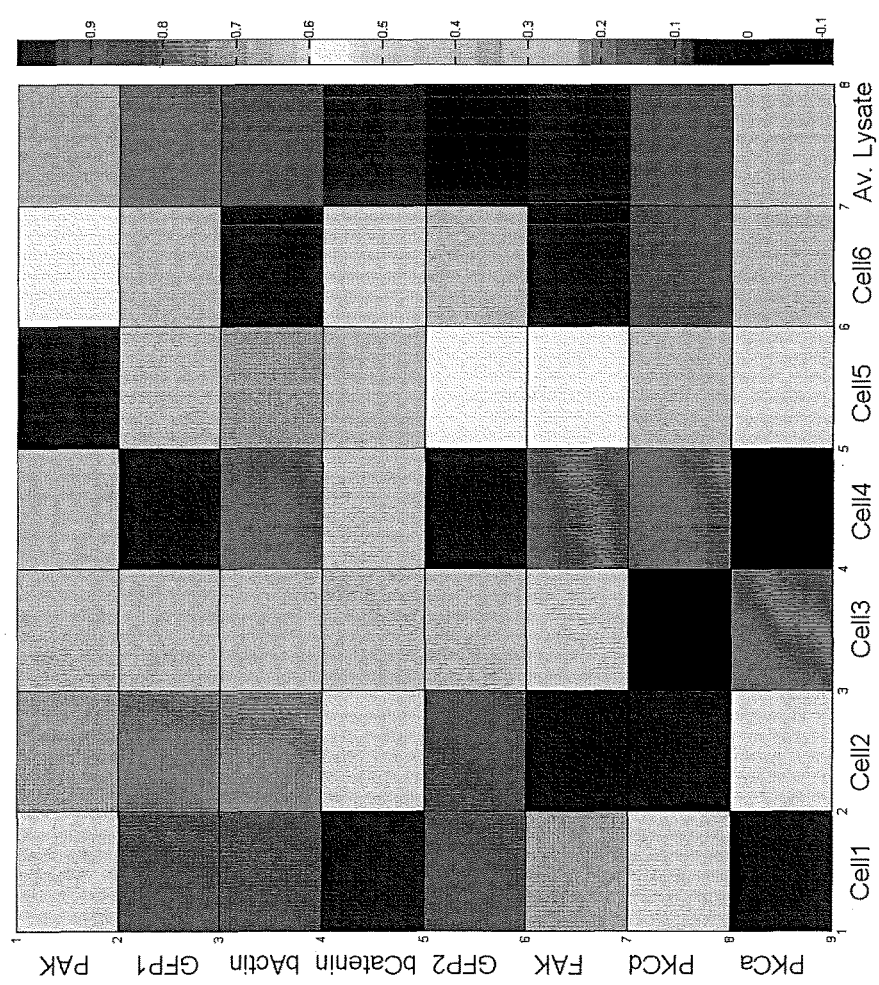
FIG. 20 is an illustration depicting integrated LA-ICP-MS counts of the measurements in FIG. 19. The time-integrated intensity of the baseline spot (from the 170th frame to the 370th frame) was subtracted from the time-integrated intensity of the single-cell lysate spot (from the 170th frame to the 370th frame) in cells 1 to 4. In cells 5 and 6, the printing of the baseline was not entirely successful and only the integrated instrument noise was subtracted from the total integrated intensity over both the baseline and the lysate spots. The maximum value within each channel across all the single cells was assigned the value of 1.0. The measurement of one spot on the titration series of the average hippocampus lysate was also included.

The integrated levels of β-actin were similar across all the sampled single cells except in one instance (FIG. 20). The β-actin levels of the second somatostatin interneuron (Cell4 in FIG. 20) were significantly lower than those of the other cells. This result did not affect the high levels of GFP measured in Single-Cell Lysate Microarrays that perfectly correlated with the pre-lysis in vivo fluorescence of this same cell. Without wishing to be bound by any particular theory, one explanation is that the current lysis buffer, used in the Inside-Out Lysis procedure, is not optimal for the solubilization of the actin network. This can be remedied by changing the formulation of the lysis buffer or by further optimizing the lysis procedure. An alternative explanation is that the levels of β-actin are variant across single cells and cannot be used for normalization. Glyceraldehyde 3-phosphate dehydrogenase (GAPDH) could be used as an alternative normalizing antigen in future measurements.

Some standard curves were non-linear within the signal range that was relevant for single-cell measurements (FIGS. 21 and 22). The PKCδ, PKCα and GFP titration series (FIGS. 21 and 22) were printed by the high precision Aushon Arrayer 2470 from the prepared dilution samples of each antigen. Eight depositions from each prepared dilution sample were printed onto each spot of the titration series by the Aushon Arrayer and thus the differences between the amounts of antigen deposited in the spots within a titration series were expected to represent the concentration differences between the corresponding dilution samples of this antigen (see Sevecka et al., 2011 for examples of Aushon Arrayer printing). Aushon does not publish the numerical values of printing noise but it is expected to be negligible in current settings. The high number of depositions per spot (8) also ensured that the lysate distribution within each printed spot was uniform. During laser ablation in the LA-ICP-MS sampling procedure, a sub-spot was sampled within each printed spot of the titration series. The position of the sub-spot within the initial spot remained the same in all laser ablation samplings of the titration series.

Figure 2:
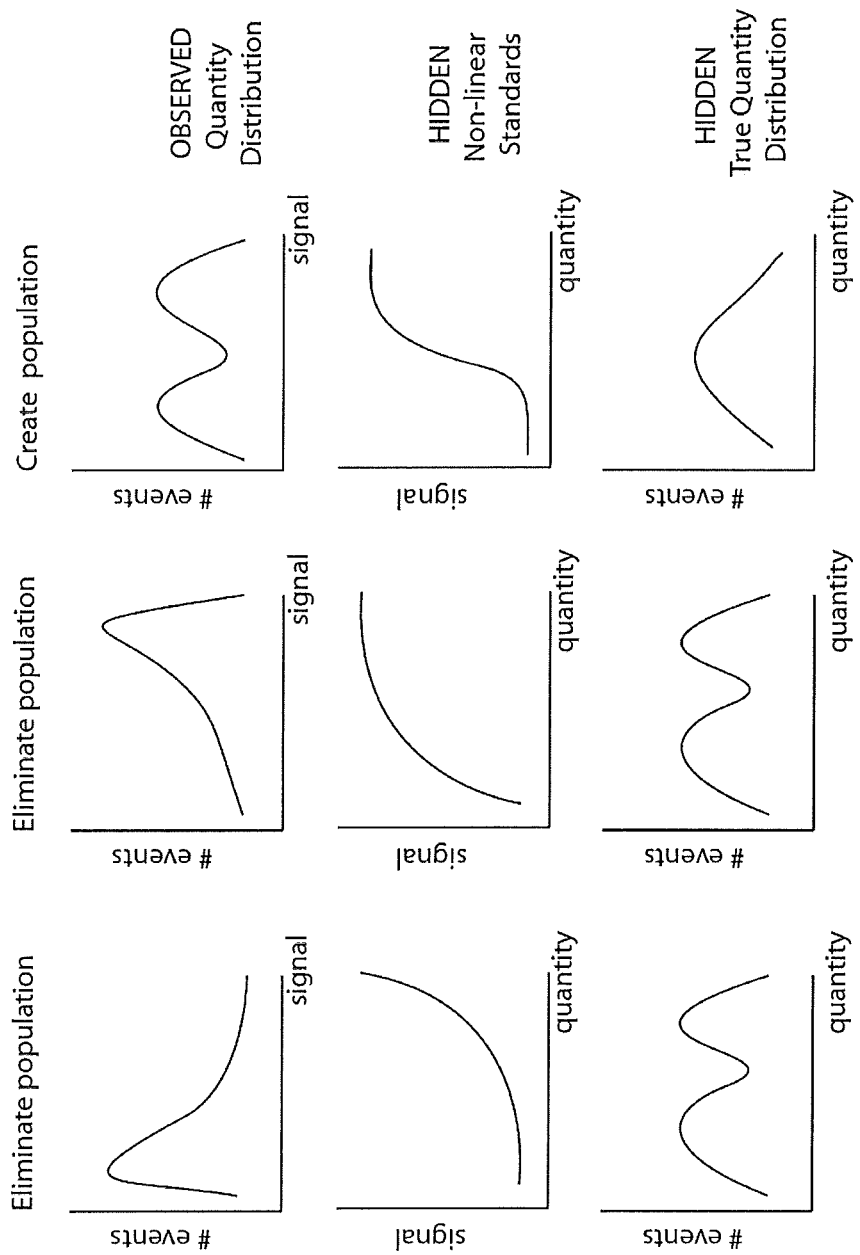
FIG. 2 is a series of graphs depicting the different non-linear standard curves. The true hidden distribution is shown in the bottom row. The distributions in the upper row were obtained by applying the standard curves in the middle row to the true hidden distributions in the bottom row. Non-linearity of the standard curves emerged when the substrate of an affinity-based probe was present in very small amounts in single cells (first case from the left). At low antigen concentrations, bivalent antibodies may not find closely located antigens to be bound by the antigen binding sites in Lysate Microarrays measurements, thereby leading to the non-linearity scenario displayed in the first case from the left. Fixation and permeabilization also changed the availability of substrates, as discussed elsewhere herein, and likely induced non-linearities.

Although not wishing to be bound by any particular theory, these experimental parameters suggest that the emergence of non-linearity at low antigen concentrations in the PKCδ and GFP standard curves (FIGS. 21 and 22) was not primarily due to the error of printing by the Aushon Arrayer and was not primarily due to the spot location error associated with the sampling procedure by LA-ICP-MS. The monotonicity and the linearity of the signal decrease in all standard curves at high antigen concentrations (high x-axis values in FIGS. 21 and 22) also implied that printing and pipetting errors did not primarily contribute to the emergence of non-linearity at low antigen concentrations. The signal levels in the last data-point of each standard curve were significantly above the instrument noise levels and above the noise across the four baseline spots (cells 1 to 4, FIG. 19), which were acquired from the same nitrocellulose pad during the same LA-ICP-MS run. Although not wishing to be bound by any particular theory, these experimental parameters suggest that the noise of printing by the Aushon Arrayer, the noise of pipetting, and the noise of the sampling procedure by LA-ICP-MS did not primarily contribute to the emergence of non-linearity at low antigen concentrations in the PKCδ and GFP standard curves (FIGS. 21 and 22). It is likely that non-linearity originated from the decrease of the probability for antibody molecules to bind and/or to stay bound to diluted antigens on nitrocellulose. Because the antibodies were bivalent, the decrease of the above probability might be associated with the fact that the binding sites of antibodies were not saturated by nearby antigens on nitrocellulose at low antigen concentrations. Single-Cell Lysate Microarrays enable the correction of these non-linearities and therefore enable the accurate measurements of quantity distributions across single-cell populations (FIGS. 1 and 2).

Example 3

Multiplexing Across Molecular Classes in Human Solid Tissues

Experiments can be performed to multiplex across multiple molecular classes. As described elsewhere herein, the lysate format is compatible with all rigorous analytical methods. Multiplex measurements of proteins, transcripts and/or metabolites can be obtained from the same single cell by subdividing the lysate partition of the sampled single cell into lysate sub-partitions as shown in FIGS. 13 and 14. In order to further decrease the sample requirements for Single-Cell Lysate Microarrays, the diameter of each printed lysate spot can be decreased from 50 μm to 20 μm. This would ensure that the signal density of the smaller 20 µm spots is approximately equivalent to the signal density of the 50 µm spots, while also maintaining a larger sub-partition of the total single-cell lysate partition for the analysis of transcripts (RT-qPCR) and/or metabolites (MALDI). In this setting, the procedure of laser ablation with LA-ICP-MS can be adjusted in order to take full advantage of the high signal density in the smaller 20 µm lysate spot, wherein the diameter of the laser beam can be adjusted to 20 µm and the energy of the laser tuned such that the whole spot can be sampled within just 1 or 2 laser pulses. These two adjustments generate a high signal differential at the elemental counter of the LA-ICP-MS instrument within the interval of just a few seconds, making it unnecessary to integrate the signal curve over a long time interval in sampling sessions. This can provide a high signal-to-noise ratio with respect to the inherent noise of the LA-ICP-MS instrument and to the noise generated by the laser-ablated nitrocellulose. Therefore, comparable Single-Cell Lysate Microarray measurements can be obtained with just a small sub-partition of the total single-cell lysate partition. The other sub-partitions of the total single-cell lysate partition can be used for the analysis of transcripts and/or metabolites. Sampling procedures can also be optimized in order to better mix the lysate inside the cell before its uptake by suction and before its subdivision into sub-partitions.

After depositing the first sub-partition of the total single-cell lysate partition into the 20 µm spot on nitrocellulose for multiplex protein measurements with Single-Cell Lysate Microarrays, the analysis of the residual sub-partition of the total single-cell lysate can be accomplished by amplifying the transcripts in a RT-qPCR reaction. For example, this can be done within the context of the Fluidigm platform (Fluidigm Inc). The multiplex analysis of metabolites can also be achieved by MALDI. Amantonico et al. have measured the abundances of ADP, UTP, ATP, and GTP in the lysate amounts equivalent to approximately one half of a single cell of *Saccharomyces cerevisiae* (Amantonico et al., 2008, Angew. Chem. Int. Ed. Engl. 47:5382-5385). The median size of a single cell of yeast is 82 µm$^3$ (Jorgensen et al., 2002, Science 297:395-400). The size of a single mammalian COS-7 cell is 2016±208 µm$^3$ (Bohil et al., 2006, Proc. Natl. Acad. Sci. USA 103:12411-12416). Therefore, it would be expected that the amount of single-cell material can be considerably larger in the case of mammalian cells, thus enabling even more extensive metabolite multiplexing.

Additionally, the platform can be used to enable single-cell analysis in solid human tissues. Organotypic cultures of human tumors have been shown to develop normally for one week after biopsy harvesting and slicing (Vaira et al., 2010, Proc. Natl. Acad. Sci. USA 107:8352-8356). The sampling and analytical methods described herein can be used with organotypic cultures of human tumors to define a new category of diagnostic tests, to personalize single-cell pharmacology, and to rapidly identify mechanistic biomarkers and drug targets.

Standard Curves

Experiments can be performed to derive the actual error bars on the standard curves by printing titration series duplicates or triplicates. Titration duplicates were printed in the above experiment but were not acquired within the same LA-ICP-MS run because of the assumption that the noise of printing by the Aushon Arrayer, the noise of pipetting and the noise of the sampling procedure by LA-ICP-MS were negligible. Experiments can be performed to determine how the variance in LA-ICP-MS tuning from day to day operation affects the signals derived from the duplicates of the same titration series. The duplicates or triplicates of the same titration series can be printed on the same nitrocellulose pad and then sampled on different days with LA-ICP-MS.

The four baseline spots (cells 1 to 4) in FIG. 19 encompassed all the procedural sources of noise. As described elsewhere herein, these sources of procedural noise included: HBSS solution, tissue debris, soluble factors in tissue, the printing process, incubation/washing steps, LA-ICP-MS noise. However, these 4 baseline spots might not measure the probabilistic aspects of protein binding to nitrocellulose because these baseline spots did not appear to contain much protein. There may also be some additional noise in antibody binding to the same concentration of protein substrate on nitrocellulose under the same antibody concentration. Experiments can be performed to address these two additional sources of noise. A titration curve of the average tissue lysate can be printed in duplicates or triplicates by the high-precision Aushon Arrayer and the noise within each of 8 recorded dimensions (β-actin, β-catenin, PKCα, PKCδ, PAK1, FAK, GFP2, GFP1) across these duplicates or triplicates can be measured.

Experiments can also be performed to construct better standard curves. Different known amounts of the purified antigen can be titrated into the antigen-depleted average lysate of the tissue of interest. Such a standard can capture the cross-reactive component of the validated antibodies, which may contribute to the non-linearity of standard curves.

Example 4

Data Analysis with Bayes Nets

A test for selecting the optimal Learner (Bayes Net topology+fixed ML subroutine) was run on a related data set. The same procedure is applied in the context of single-cell measurements enabled by Inside-Out Lysis and by Single-Cell Lysate Microarrays.

The materials and methods employed in these experiments are now described.

Materials and Methods

The code was implemented in Python and was run on Python 2.6.

Each dimension of the cancer data set of dimensionality 10 consisting of 112 data points was numerated as follows: 0—Axl, 1—Met.p, 2—Stat3.p, 3—Akt.p, 4—cRaf.p, 5—Src.p, 6—Erk1.2.p, 7—S6.p1, 8—MAPK.p1, 9—Cancer Diagnosis. Each directed acyclical graph was represented as a list of tuples in Python:

NAIVE_BAYES_TUPLES=map(tuple, [[9], [9,0], [9,1], [9,2], [9,3], [9,4], [9,5], [9,6], [9,7], [9,8]])

AXL_MET_AKT_BAYES_TUPLES=map(tuple,[[9], [9,0], [9,0,1], [9,2], [9,3], [9,1,3,4], [9,5], [9,6], [9,7], [9,8]])

Each tuple was used as a key in the first layer of a dictionary of dictionaries. All possible true/false assignment tuples for each key in the first layer were used as keys in the second layer of the dictionary of dictionaries. The second-layer assignment tuples then mapped to a numerical probability value. A Bayes Net class was created to incorporate all the necessary functions, such as a function for data import and a function for parameter estimation by maximum likelihood. Each Bayes Net topology was represented by the above format and could be imported into this class. A cross-validation routine was also implemented in the Bayes Net class. The Bayes Net class was used to evaluate all 15 Bayes Net topologies by 10-fold cross-validation.

The results of the experiments are now described.

Bayes Net Topologies

Figure 23:
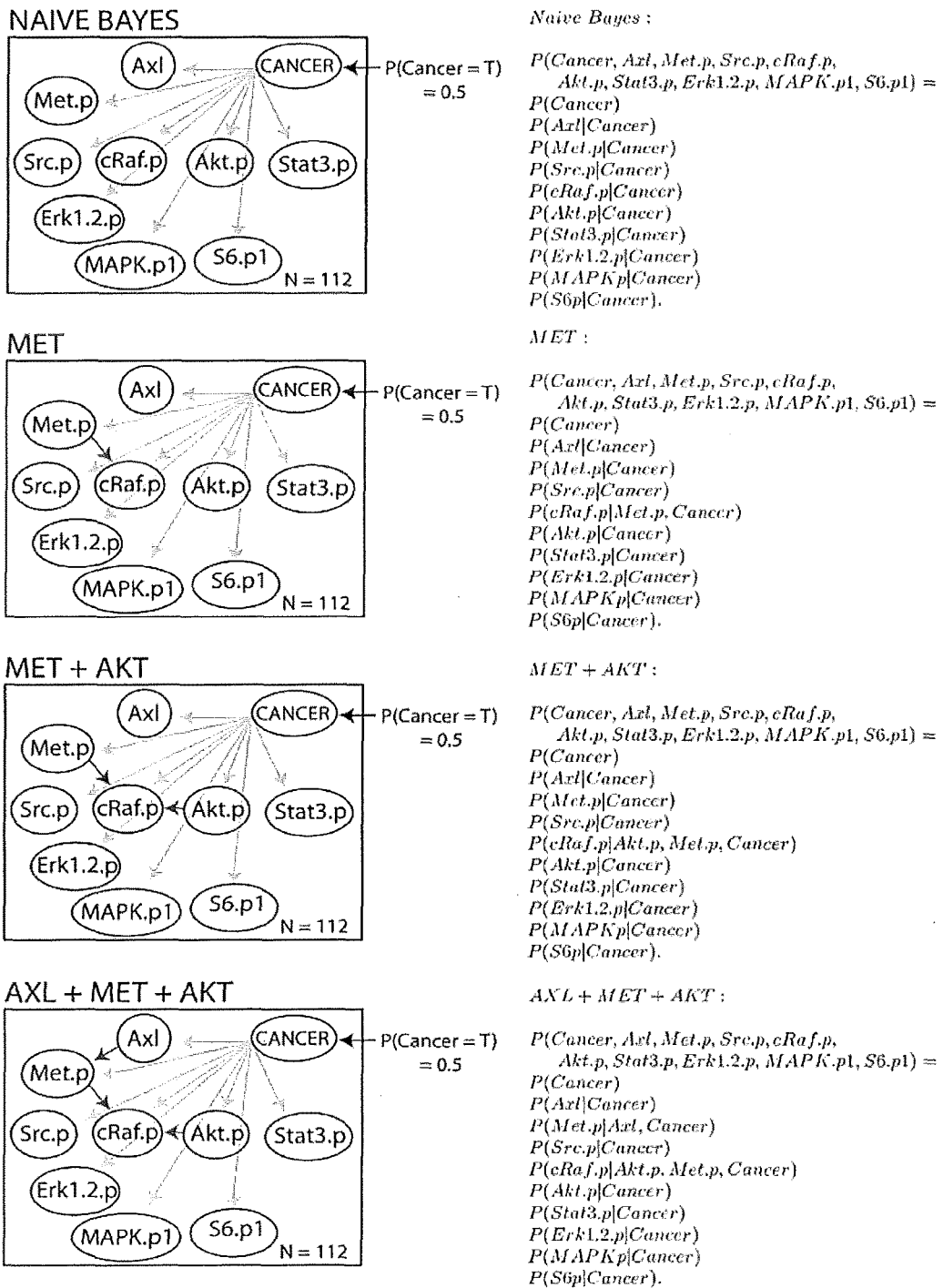
FIG. 23 is a series of illustrations depicting Bayes Net topologies. Eight Bayes Net topologies with increasing complexities and the corresponding formal mathematical representations are depicted.

In a highly dimensional data set, each data point is a long vector of multiplex measurements. For example, by measuring 10 proteins in each of 100 different samples, a data set of dimensionality 10 consisting of 100 data points is obtained. Each dimension in such a data set can be considered as a random variable. The entire data set can then be formally represented by the joint probability distribution of all the random variables. It may be difficult to visualize and to reason about the many possible conditional independence assumptions in the joint probability distribution of a highly dimensional data set without a convenient graphical representation. The idea underlying Bayes Nets is that a joint probability distribution can be represented by a directed acyclical graph (Pearl, 1982, Proceedings, AAAI-82). Such a graph is easy to visualize, analyze, and modify. The direction of the edges in a Bayes Net can be used to write down the formal mathematical representation of the corresponding joint probability distribution (FIG. 23). A random variable in a Bayes Net is conditionally independent from all the non-descendent random variables if it is conditioned on all its parent random variables (Pearl, 1982, Proceedings, AAAI-82). The topology of a Bayes Net incorporates all the conditional independence assumptions. Given a fixed set of random variables (vertices), the same set of conditional independence assumptions can be represented by different Bayes Net topologies (edges) (Pfeffer and Parkes, 2010, CS181 Lecture Notes, Harvard University). Thus, the same set of conditional independence assumptions can be mapped to different Bayes Net topologies.

The graphical representation of the joint probability distribution of a highly dimensional data set is also useful because of the availability of standard graph algorithms in computer science. Many interesting problems related to the joint probability distribution of data can be reduced to the corresponding graph problems and therefore, can be solved efficiently by graph algorithms on large problem instances. Because a Bayes Net represents the corresponding joint probability distribution, it can also be used for data sampling in a generative manner.

There are standard ways to learn the parameter values of a given Bayes Net topology from the data set. Given a topology of a Bayes Net, the corresponding parameter values can be estimated by maximum likelihood (ML). If a prior distribution on parameter values is desirable, the maximum a posteriori method (MAP) can be used. If there are hidden random variables in the Bayes Net, then the expectation maximization (EM) algorithm with either the ML subroutine or the MAP subroutine can be used to learn the parameter values from the given data set. All these methods can fit the topology of a given Bayes Net to the data set by estimating the fitting parameter values. However, the fit of a Bayes Net to the data set is a poor measure of how well the parameter values and the topology of this particular Bayes Net capture the true hidden concept in the data set which is to be learned. A data set is a sample from the distribution of data sets that can be generated by the true hidden concept. In order to avoid over-interpreting the patterns in one particular data set, the optimal Bayes Net with minimal overfitting is found.

It is common to attribute overfitting to the presence of noise in the data set. However, overfitting can also occur in fully deterministic domains without noise. In deterministic domains, the main cause of overfitting is the 'curse of dimensionality' (Pfeffer and Parkes, 2010, CS181 Lecture Notes, Harvard University; Bishop, 2006, Pattern Recognition and Machine Learning, Springer, First Edition). The 'curse of dimensionality' is also a major cause of overfitting in non-deterministic (noisy) domains. For example, in genomics thousands of noisy features (dimensions) are recorded in just a few genomes (data points). Given a highly dimensional data set consisting of just a few data points, it is quite likely that interesting patterns will emerge across some of the many dimensions of the data set simply by chance and solely due to the small number of sampled data points. These patterns are spurious and do not accurately represent the true hidden concept which is to be learned. Such spurious patterns can be eliminated by sampling more data points from the same true hidden concept. However, data is generally more expensive than computation. It is preferably to minimize overfitting caused by the noise of measurements and by the 'curse of dimensionality' without acquiring more data.

The Bayes Net topology, representing the hypothesis space before estimating the parameter values, was distinguished from the final Bayes Net model with fully estimated parameter values that can be used for different inference tasks such as classification. The best way to test the generality of a given Bayes Net model with fully estimated parameter values is to assess the accuracy of its predictions on an independent data set sampled from the same hidden concept. Given an arbitrary data set, it can be subdivided it into two disjoint sets: a training set and a test set. The parameter values of a given Bayes Net topology can be determined by applying the parameter estimation routine (ML, MAP or EM) to the training set. The generality of the learned Bayes Net model can be assessed with the estimated parameter values by testing its prediction accuracy on the test set, which is independently and identically sampled from the same hidden concept. However, this does not solve the problem of overfitting, because the initial Bayes Net topology might represent a hypothesis space that is too large or too small in the context of the true hidden concept and/or in the context of the given data set (Kearns and Vazirani, 1994, An Introduction to Computational Learning Theory, MIT Press). To minimize overfitting the optimal Bayes Net topology that represents the optimal hypothesis space must first be selected (Pfeffer and Parkes, 2010, CS181 Lecture Notes, Harvard University).

A learning algorithm (Learner) is defined as a function that maps a data set to a model with fully estimated parameter values. Clearly, one given Learner will likely produce different models on different data sets. The learning algorithm in the case of a Bayes Net is defined by the parameter estimation method (ML, MAP or EM) and by the topology (conditional independence assumptions) of this particular Bayes Net. Given a fixed parameter estimation method such as ML, different Learners can be generated by modifying Bayes Net topologies. The problem of comparing different Bayes Net topologies thus reduces to the problem of selecting the optimal Learner. The problem of selecting the optimal Learner is at the core of Machine Learning.

One approach is to train each Learner on one training set and to test the learned model, output by each Learner, on one independently and identically sampled test set. Then, the Learner that outputs the model with the best prediction accuracy on the test set is the optimal Learner. However, the data set is a random variable too. Only one training set and one test set will likely result in the selection of a non-optimal Learner. Therefore, the expected performance of each Learner is estimated and the optimal Learner is selected based on its expected performance across many independently and identically (iid) sampled training set and test set pairs. The above process of training and testing is repeated on many pairs of iid sampled training and test sets with each Learner and then the average prediction accuracy of the models output by each Learner is calculated across these training set and test set pairs. This procedure will provide the expected performance estimate of each Learner. The Learner that outputs the models with the best average prediction accuracy across all the test sets is the optimal Learner.

Given a data set of limited size, cross-validation is an appropriate approximation for the selection of the optimal Learner based on its expected performance (Pfeffer and Parkes, 2010, CS181 Lecture Notes, Harvard University). Cross-validation enables selecting the optimal Learner on just one data set. In a k-fold cross-validation, the data set is subdivided into k subsets of equal size. In this way, k iid sampled test sets are obtained, each used in only one of the k runs of the k-fold cross-validation. The training set in each of the k runs of the k-fold cross-validation consists of the other k−1 subsets excluding the current test set. Thus, the training sets overlap across the k runs of the k-fold cross-validation and are not independent (in contrast to the test sets). However, k-fold cross-validation provides a good approximation for selecting the optimal Learner based on its expected performance with limited data. Eventually, after selecting the optimal Learner the final optimal model can be learned with minimal overfitting by applying the selected optimal Learner to the whole data set. Importantly, the average test set accuracy of the models, output by the optimal Learner in the above Learner selection procedure, cannot be considered as the expected prediction accuracy of the final optimal model. This can be done on another independent data set that was not used for Learner selection. In practice, however, it is often enough to know that the selected Learner (Bayes Net topology+ML) is the optimal Learner, before starting to use its final output model in real applications without actually determining the expected prediction accuracy of the final model.

In summary, the minimization of overfitting is achieved by selecting the optimal Learner function with the optimal hypothesis space. The optimal hypothesis space defined by the optimal Learner minimizes the extent of overfitting in the final model. The final model, output by the optimal Learner, is general and captures the true hidden concept with minimal overfitting.

Data Set

A data set of multiplex protein measurements was acquired with Lysate Microarrays. Flash-frozen human tissue samples from 56 human patients were lysed in RIPA buffer. A tumor tissue sample and a sample of the adjacent normal tissue were collected from each patient. In total, 56 samples of tumor tissue and 56 samples of normal tissue were obtained. Most tumors were identified as ductal carcinoma (48 out of 56). Each of the 112 samples was printed on 100 different glass-mounted nitrocellulose pads by an Aushon Arrayer. Each of these pads was then incubated with a different primary antibody, previously validated for Lysate Microarrays from the initial set of several thousands of antibodies. This set of validated antibodies included pan-specific antibodies and phospho-specific antibodies. Each nitrocellulose pad was also incubated with a validated β-actin antibody for normalization purposes. After the subsequent incubation with the corresponding secondary antibodies, all signal intensities were recorded and compiled in one file.

Optimal Bayes Net Topology

The first problem related to the above-described data set was its high dimensionality (101:100 proteins+Cancer/Normal phenotype) and a relatively low number of data points (112). Given such a high dimensionality, it was likely that interesting patterns could emerge simply by chance without properly representing the true hidden concept of cancer. In order to perform the data-driven selection of the optimal Bayes Net topology, the number of dimensions was reduced by focusing on only one particular signaling pathway. Out of 101 dimensions, 10 were selected: Cancer/Normal phenotype, Axl, Met.p, Src.p, cRafp, Akt.p, Stat3.p, Erk1.2.p, MAPK.p1 and S6.p1. This selection was made without any prior inspection of the data set. In this way, the dimensionality of each of the 112 data points was reduced to 10. Empirically, such a ratio between the number of dimensions and the number of data points was expected to yield meaningful results.

Given the data set of dimensionality 10 consisting of 112 data points, it was determined which set of conditional independence assumptions optimized the hypothesis space for capturing the true hidden concept of cancer. The data set was binarized by choosing the median value within each dimension as its binarization threshold. 15 different Bayes Net topologies were empirically chosen. Each Bayes Net topology consisted of the same 10 Bernoulli random variables, but had a different set of directed edges thus presumably representing a different set of conditional independence assumptions (FIG. 23). Each Bernoulli random variable represented one dimension of the data set: Axl, Met.p, Src.p, cRaf.p, Akt.p, Stat3.p, Erk1.2.p, MAPK.p1, S6.p1 and the Cancer/Normal phenotype (FIG. 23). These 15 different Bayes Net topologies also had different complexities determined by counting the number of the free parameters in each topology. Because the data set was balanced, the prior distribution for the Cancer random variable was as follows: P(Cancer=True)=0.5, P(Cancer=False)=0.5 (FIG. 23).

The procedure of Learner selection was performed on the set of 15 Bayes Net topologies by 10-fold cross-validation (ML procedure was the same in all Learners). 8 of these topologies are displayed in FIG. 23. The parameter values of each Bayes Net topology were estimated by the maximum likelihood method on the training set in each run of the 10-fold cross-validation. Because all the random variables of the 15 Bayes Net topologies were Bernoulli random variables, the maximum likelihood method was reduced to a simple counting and normalization procedure of the corresponding instances in the training set (Bishop, 2006, Pattern Recognition and Machine Learning, Springer, First Edition). In order to evaluate how well each learned Bayes Net model with estimated parameter values captured the true hidden concept of cancer, an appropriate measure of prediction accuracy was chosen on the test set. It was decided that the classification accuracy of the cancer phenotype was an appropriate measure of prediction accuracy. In each of the 10 runs of the 10-fold cross-validation, the parameter values of the given Bayes Net topology were estimated on the training set and then the Bayes Net model with estimated parameter values was tested on the test set by comparing the predicted values of the cancer phenotype (True or False) with the actual values of the cancer phenotype. Formally, this classification task can be formulated as follows:

$$\text{argmax}_{c \in \{True, False\}} P(\text{Cancer}=c, \text{Evidence} | \theta_{ML})$$

where Evidence represents all the current assignments of the protein random variables in the currently considered data point of the test set and $\theta_{ML}$ represents the parameters estimated by the maximum likelihood method on the training set in each run of 10-fold cross-validation. If the predicted argmax result is the same as the actual value of the cancer phenotype in the currently considered data point of the test set, then this case was interpreted as a match. Otherwise, it was a mismatch. By counting the number of matches and mismatches in the test set of the current run of the 10-fold cross-validation, the prediction accuracy in this test set was obtained. In total, the prediction accuracy was determined ten times for each Learner in the 10-fold cross-validation. The expected performance of each Learner (Bayes Net topology) was calculated by averaging the accuracy rates of output models across all the 10 test sets. Overall, 15 topologies were evaluated by 10-fold cross-validation and 15 values of expected performance were obtained.

Figure 24:
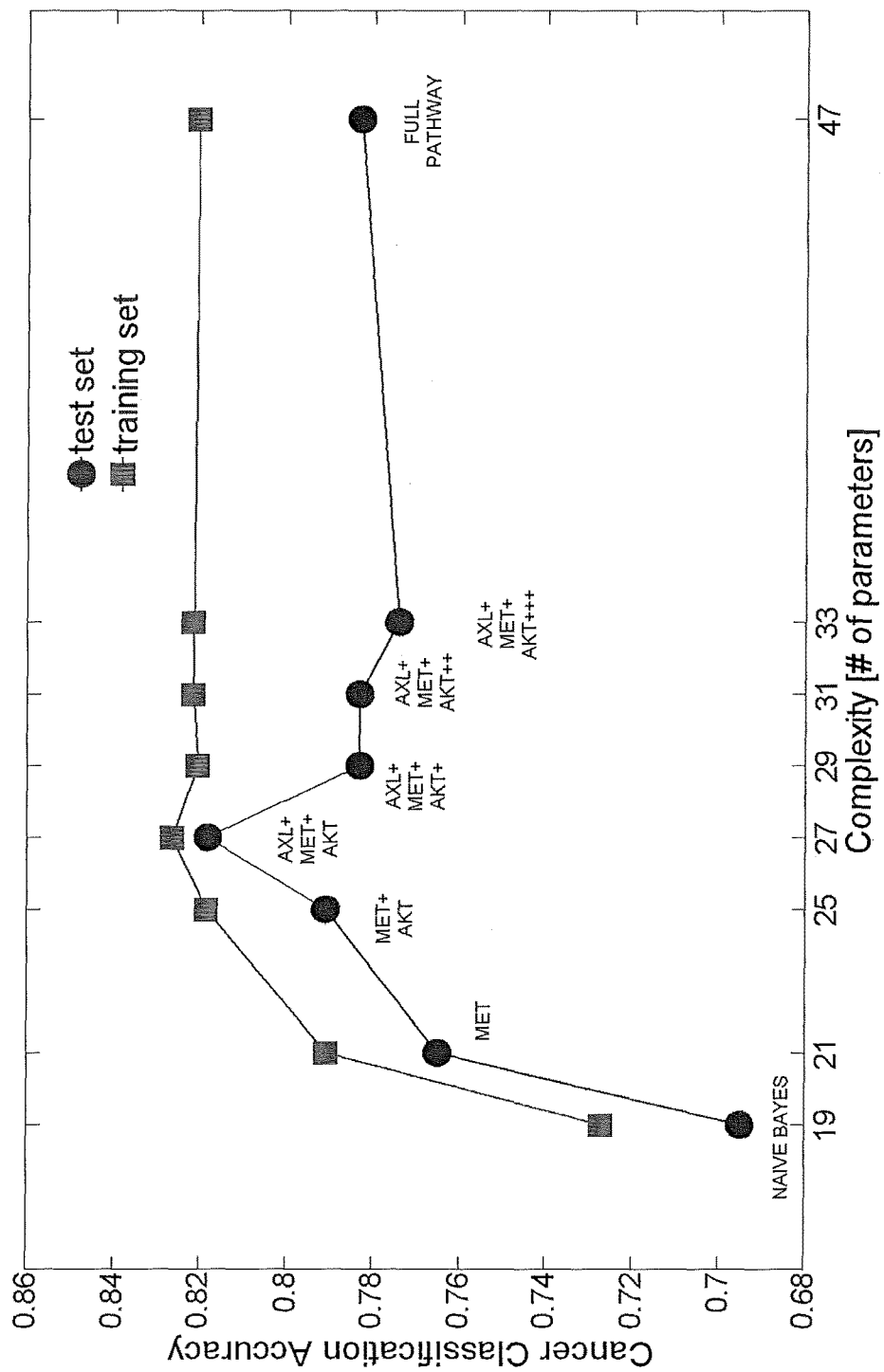
FIG. 24 is a graph depicting the selection of the optimal Learner (Bayes Net topology+ML parameter estimation). The optimal Learner was selected from a set of Learners by running the 10-fold cross-validation with each Learner on the data set of dimensionality 10 and consisting of 112 data points. In each of the 10 runs of the cross-validation, the training set was used as input to the Learner function and the resulting Bayes Net model was used to calculate the classification accuracy in the test set and in the training set. This procedure was performed across all the 10 runs of cross-validation and the average cancer classification accuracies are displayed in the figure. 10-fold cross-validation was performed with each Learner. The optimal Learner is AXL+MET+AKT. The simplest topology of Naïve Bayes performed well but considerably worse than AXL+MET+AKT. Increasing the complexity of the Bayes Net topologies beyond the complexity of AXL+MET+AKT led to the suboptimal expansion of the hypothesis space and thus to overfitting.

FIG. 24 shows the results of running 10-fold cross-validation on the 8 topologies displayed in FIG. 23. These 8 topologies were selected for demonstration because of their logical progression. The average performance on the training set was found to be consistently better than the average performance on the test set for any Learner (Bayes Net topology). This result is consistent with the output models always fitting the data in the training sets better than the data in the unseen independent test sets. Surprisingly, the models based on the Naïve Bayes topology did quite well on average in predicting the correct cancer phenotype. In this data set, higher phosphorylation levels were observed across all the proteins in cancerous samples in contrast to normal samples. Thus, conditioning all the protein random variables on the Cancer random variable was sufficient to capture this general tendency for higher phosphorylation levels in the cancerous samples. AXL+MET+AKT was the topology with the best expected performance. This topology had three additional edges on top of the Naïve Bayes topology. By conditioning the phosphorylation levels of Met.p on Cancer and Axl (AXL+MET+AKT), a better hypothesis space was obtained than by conditioning the phosphorylation levels of Met.p on Cancer alone (MET+AKT), given that cRaf.p was conditioned on Met.p, Akt.p and Cancer in both cases (FIGS. 23 and 24). By conditioning cRaf.p on Met.p, Akt.p and Cancer (MET+AKT), a better hypothesis space was obtained than by conditioning cRaf.p on Cancer alone (NAÏVE BAYES) or by condition cRaf.p on Cancer and Met.p alone (MET) (FIGS. 23 and 24). Importantly, the addition of more complexity to the AXL+MET+AKT topology expanded the hypothesis space of the resulting Learners beyond the optimal level of complexity and did not improve their expected performance because of overfitting.

Figure 25:
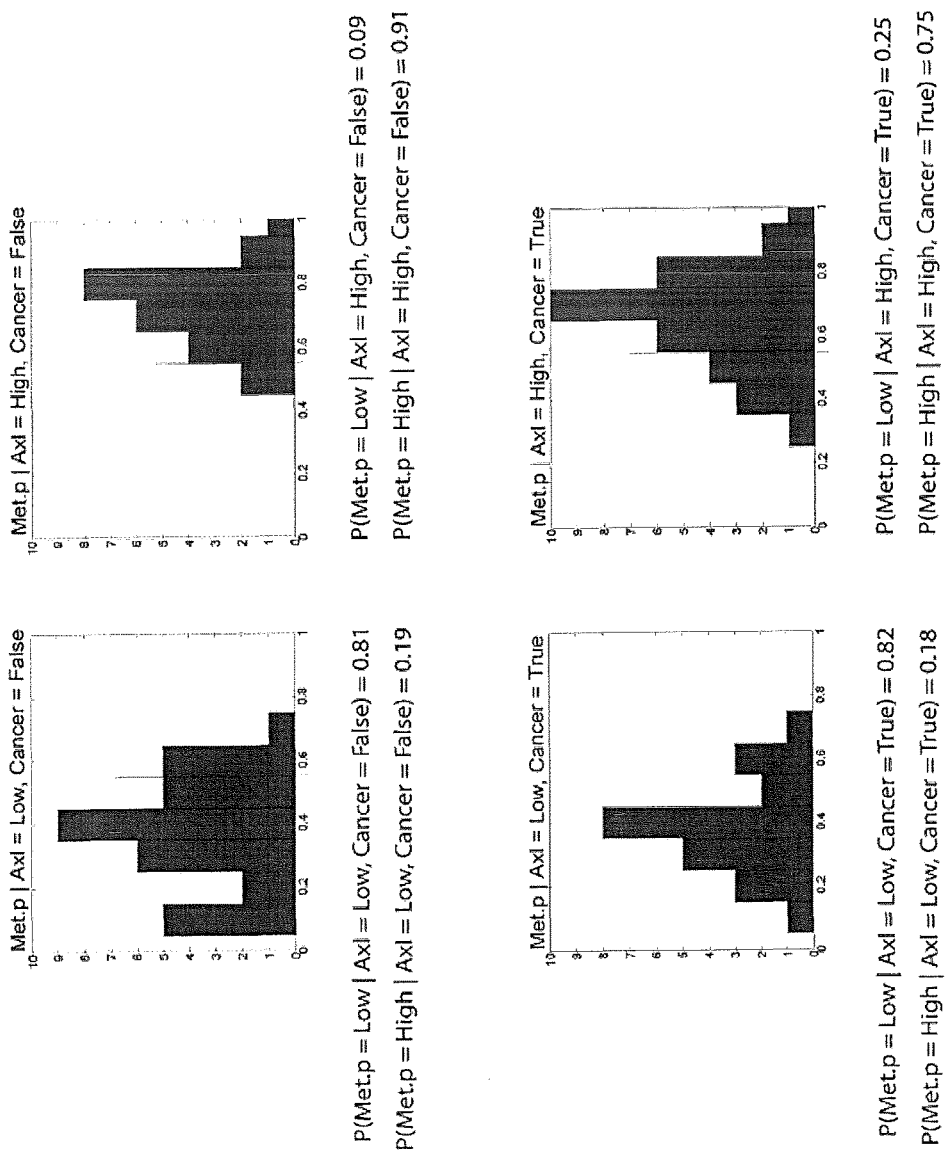
FIG. 25 is a series of graphs depicting how additional conditioning led to better test-set classification. A better separation of Met.p data was achieved by conditioning on Axl and Cancer random variables. Without conditioning on Axl, the distribution of Met.p was similar both for Cancer=True and for Cancer=False. The additional conditioning on Axl led to the different conditional distributions of Met.p when conditioned on Axl=High, Cancer=False and when conditioned on Axl=High, Cancer=True. This distinction enabled for a better average classification accuracy across the AXL+MET+AKT models as compared to the MET+AKT models in FIG. 24. Line is the median used for binarization of data.

An explanation of why the incorporation of additional edges into the Bayes Net topology led to a better classification accuracy of the resulting learned models is shown in FIG. 25. The distribution of Met.p levels in the cancerous samples was similar to the distribution of Met.p in the non-cancerous samples. Thus, after binarization, the probability of Met.p to be highly phosphorylated was approximately equal to the probability of Met.p to be phosphorylated at low levels in both the cancerous and non-cancerous samples. However, by adding an additional conditioning arrow from Axl to Met.p different conditional distributions of Met.p were obtained when conditioned on Axl=High, Cancer=False and when conditioned on Axl=High, Cancer=True (FIG. 25). Effectively, it was observed that in the samples with high Axl levels, the phosphorylation levels of Met.p were more likely to be low in the cancerous samples than in the non-cancerous samples. After adding the Axl-Met.p edge to the MET+AKT topology, such a distinction led to better average classification accuracy when all the conditional probabilities were multiplied in the total joint probability distribution used in the classification task (FIG. 24).

Because Bayes Nets enable the modification of graph topologies with a clear understanding of conditional independence assumptions by humans, the above approach can be used to search for the conditional independence assumptions that optimize the hypothesis space for capturing the true hidden concept of cancer. The edges of the optimal Bayes Net topology can be interpreted causally in the context of protein interactions. At the level of single cells, this approach can allow for searching for the Bayes Net topologies that enable capturing the underlying concepts of cell types. Given a highly dimensional data set sampled from different cell types, the Bayes Nets (topologies and the resulting models) can be identified that accurately capture the concept (molecular mechanism) of each cell type. Such cell-type specific Bayes Nets can be used for data interpolation in order to predict the mechanistic response of each cell type to previously unseen stimulation conditions in response to drugs.

Experiments can be performed to apply the procedure of selecting the optimal Learner (Bayes Net topology+fixed ML subroutine) in the context of single-cell measurements enabled by Inside-Out Lysis and by Single-Cell Lysate Microarrays. Experiments can also be performed on single-cell measurements in animal solid tissues or in human tumor tissues. Experiments can also be performed to look for and identify new cell types based on single cell data by building in hidden random variable(s) and by using EM for parameter estimation.

Example 5

Inside Out Lysis Technology in the Investigation of Psychiatric Diseases

The Inside Out Lysis technology described herein can be used to investigate psychiatric diseases. In recent years, several mice have been engineered to carry genetic modifications found in schizophrenia and autism, and the mice are now commercially available. The mice described elsewhere herein can be bred with these disease models to produce mice harboring disease-relevant genetic mutations that express GFP in defined subsets of interneurons. Slice cultures are particularly relevant for studying questions related to brain development. After generating the appropriate strains of mice, Inside Out Lysis technology can be used to obtain interneuron lysates from several developmental time points in different regions of the brain.

Interestingly, it has been found that TrkB signaling is significantly altered in parvalbumin expressing interneurons of schizophrenic patients (Lewis D, et al. (2005) Nature Rev. Neurosci. 6, 312-324). Using the technology described elesewhere herein, the differences of TrkB signaling in different subsets of interneurons in mouse models of schizophrenia and autism can be investigated over the first two months of development, providing insight into the molecular events underlying these debilitating disorders.

Example 6

Determining Absolute Counts of Measured Proteins in a Single Cell

Experiments can be performed to determine the absolute counts of the measured proteins in each single cell. These counts can be obtained when the signal for the protein, such as GFP, PKCδ and PKCα, is mapped to the absolute quantity. Although it is practically difficult to determine the exact volume deposited by the Aushon Arrayer in each spot of the printed concurrent titration series, this can be resolved by manually printing a well-defined amount of the respective purified proteins of control lysates next to the Aushon-printed titration series. By measuring the antigen amounts in the spots with the known antigen quantities, the spots of the Aushon Arrayer-printed titration series can be mapped to their respective absolute quantities. Consequently, the absolute standard curves can be derived and the absolute levels of proteins in each printed single-cell lysate can be determined.

A somatostatin interneuron can be lysed from a living brain slice culture displayed in and spotted onto nitrocellulose as described elsewhere herein. The nitrocellulose plate can be prepared with an extensive dilution series (1:1.25 resolution) of purified GFP titrated across different levels of actin background (average hippocampus lysate). The high resolution of dilution series can allow for reliable fitting of nonlinear functions without overfitting (titration data constrains the hypothesis within its hypothesis space). Error values can be estimated reliably as well, and cross-reactivities can be filtered out. Nonlinearities of the signal-to-quantity function that are crucial for correct population size estimations can be accounted for with high resolution titration series and with nonlinear fitting. Printing of the titrations of phoshpo-peptides (blocking peptides for phospho-specific antibodies) can be carried out. The absolute phoshporylation levels combined with the absolute total amounts of proteins can also be determined in the above manner.

Example 7

Analytical Chemistry Technology in Neurobiology

According to recent estimates, the amount of ATP in a single neuron is within the sensitivity range of a mass spectrometer. Experiments can be carried out to determine the amount of ATP in a single neuron. Experiments can also be carried out to provide extensive multiplexing with the help of Dynal beads or other methods. Breeding homozygous GFP carriers with non-carriers can create mice with half the amount of GFP in interneurons. The specificity of absolute measurements can then be further assessed. These experiments can determine the current experimental bounds on what type of data can be acquired. Given these bounds, a pathology-related investigation can be accomplished in order to enable the scaling of analytical chemistry technology in neurobiology.

Whereas most human diseases occur in solid tissues (the exception being for example blood-based diseases like leukemia), most molecular profiling studies in neuroscience and systems biology have so far been performed in cell lines and dissociated cultures, grown in petri dishes outside the native tissue context. Native heterogeneity of cell types is not preserved in these samples.

The sampling technology of the present invention uses complex chemistry to solubilize single cells in solid tissues from inside the intracellular space. The "from inside" directionality of the solubilization process enables perfect spatial and high temporal single-cell resolution in complex tissues. The solubilization chemistry enables collection of all molecules of each sample single cell and analysis of these molecules with most sensitive quantitative profiling methods.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of lysing a single cell present in a tissue, the method comprising:
   a) identifying a cell from a live, solid tissue;
   b) contacting a detergent-containing lysis buffer with the intracellular space of the identified cell,
      wherein the concentration of the detergent is above its critical micellar concentration (CMC) value;
   c) allowing the lysis buffer to dilute to a concentration that is below its CMC value and further allowing the lysis buffer to spread within the intracellular space of the identified cell for a period of time until the detergent concentration approaches its CMC value, and wherein the cell is lysed from the inside of the cell; and
   d) collecting the lysate.

2. The method of claim 1, wherein the method occurs in the absence of tissue fixation and tissue disaggregation.

3. The method of claim 1, wherein the identified cell is in an organotypic culture.

4. The method of claim 1, wherein the lysate is collected by suctioning the lysate using a suction channel.

5. The method of claim 4, wherein the suction channel is a bent suction micropipette.

6. The method of claim 1, wherein the collected lysate is further applied to a nitrocellulose pad.

7. The method of claim 6, wherein a standard is also applied to the nitrocellulose pad.

8. The method of claim 7, wherein the collected lysate from a single cell is repeatedly spotted on the same spot of the nitrocellulose pad, thereby enriching proteins in the collected lysate on the nitrocellulose pad.

9. The method of claim 1, wherein the lysate is evaluated using an analytical method.

10. The method of claim 9, wherein the analytical method is selected from the group consisting of mass spectrometry, protein microarray, RT-qPCR, RNA-Seq, and MALDI-MS.

11. The method of claim 1, wherein the detergent is sodium dodecyl sulfate.

12. The method of claim 1, wherein the outer cell membrane of the identified cell is intact or mostly intact prior to lysate collection.

13. A method of analyzing a cell present in a tissue, the method comprising:
   a) identifying a cell from a live, solid tissue;
   b) contacting a detergent-containing lysis buffer to the intracellular space of the identified cell,
      wherein the concentration of the detergent is above its critical micellar concentration (CMC) value;
   c) allowing the lysis buffer to dilute to a concentration that is below its CMC value and further allowing the lysis buffer to spread within the intracellular space of the identified cell for a period of time until the detergent concentration approaches its CMC value, and wherein the cell is lysed from the inside of the cell;
   d) collecting the lysate;
   e) applying the collected lysate to a solid support; and
   f) evaluating the collected lysate using an analytical method.

14. The method of claim 13, wherein the outer cell membrane of the identified cell is intact or mostly intact prior to lysate collection.

15. The method of claim 13, wherein the solid support comprises a nitrocellulose pad.

16. The method of claim 15, wherein the collected lysate from the single cell is repeatedly spotted on the same spot of the nitrocellulose pad, thereby enriching proteins in the collected lysate on the nitrocellulose pad.

* * * * *